United States Patent
Barr et al.

(10) Patent No.: US 9,732,362 B2
(45) Date of Patent: Aug. 15, 2017

(54) PROCESSES AND SYSTEMS FOR ALCOHOL PRODUCTION AND RECOVERY

(71) Applicant: BUTAMAX ADVANCED BIOFUELS LLC, Wilmington, DE (US)

(72) Inventors: Steven Christopher Barr, West Chester, PA (US); Robert W. Sylvester, Newark, DE (US); Joseph J. Zaher, Newark, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 13/887,209

(22) Filed: May 3, 2013

(65) Prior Publication Data

US 2013/0309738 A1    Nov. 21, 2013

Related U.S. Application Data

(60) Provisional application No. 61/642,757, filed on May 4, 2012.

(51) Int. Cl.
*C12P 7/16* (2006.01)
*C12P 7/06* (2006.01)
*C12M 1/00* (2006.01)

(52) U.S. Cl.
CPC .............. *C12P 7/06* (2013.01); *C12M 21/12* (2013.01); *C12M 29/18* (2013.01); *C12P 7/16* (2013.01); *Y02E 50/17* (2013.01); *Y10T 29/49716* (2015.01)

(58) Field of Classification Search
CPC ........... C12P 7/16; C12M 29/18; C12M 21/12
See application file for complete search history.

(56) References Cited

U.S. PATENT DOCUMENTS

| | | | |
|---|---|---|---|
| 419,332 | A | 1/1890 | Horne |
| 4,349,628 | A | 9/1982 | English et al. |
| 4,359,533 | A | 11/1982 | Wilke et al. |
| 5,514,583 | A | 5/1996 | Picataggio et al. |
| 5,712,133 | A | 1/1998 | Picataggio et al. |
| 7,223,575 | B2 | 5/2007 | Zhang et al. |
| 7,297,236 | B1 | 11/2007 | Vander Griend |
| 7,572,353 | B1 | 8/2009 | Vander Griend |

(Continued)

FOREIGN PATENT DOCUMENTS

| | | |
|---|---|---|
| WO | WO 95/28476 | 10/1995 |
| WO | WO 2008/143704 | 11/2008 |

(Continued)

OTHER PUBLICATIONS

Wikipedia, Fusel Alcohol, Accessed Mar. 18, 2014, online at: en.wikipedia.org/wiki/Fusel_alcohol.*

(Continued)

*Primary Examiner* — Karen Cochrane Carlson
*Assistant Examiner* — Jennifer M. H. Tichy

(57) ABSTRACT

The present invention relates to processes for recovering butanol produced in a fermentative process using, for example, an ethanol production plant which has been reversibly-retrofitted for butanol production, that is, the ethanol production plant may be converted for butanol production, but can also revert to an ethanol production. The present invention also relates to processes for recovering butanol produced in a fermentative process in a butanol production plant that may be converted to ethanol production plant.

24 Claims, 19 Drawing Sheets

(56) References Cited

U.S. PATENT DOCUMENTS

| | | |
|---|---|---|
| 7,666,282 B2 | 2/2010 | Sylvester et al. |
| 7,741,119 B2 | 6/2010 | Viitanen et al. |
| 8,101,808 B2 | 1/2012 | Evanko et al. |
| 8,304,588 B2 | 11/2012 | Evanko et al. |
| 8,426,173 B2 | 4/2013 | Bramucci et al. |
| 8,426,174 B2 | 4/2013 | Bramucci et al. |
| 8,460,439 B2 | 6/2013 | Parten |
| 8,476,047 B2 | 7/2013 | Burlew et al. |
| 8,563,788 B2 | 10/2013 | Grady et al. |
| 8,569,552 B2 | 10/2013 | Grady et al. |
| 8,617,861 B2 | 12/2013 | Grady et al. |
| 8,697,404 B2 | 4/2014 | Anton et al. |
| 8,759,044 B2 | 6/2014 | DiCosimo et al. |
| 8,765,425 B2 | 7/2014 | DiCosimo et al. |
| 2007/0031918 A1 | 2/2007 | Dunson, Jr. et al. |
| 2007/0092957 A1 | 4/2007 | Donaldson et al. |
| 2007/0259410 A1 | 11/2007 | Donaldson et al. |
| 2007/0292927 A1 | 12/2007 | Donaldson et al. |
| 2008/0015395 A1 | 1/2008 | D'Amore et al. |
| 2008/0045754 A1 | 2/2008 | D'Amore et al. |
| 2008/0124774 A1 | 5/2008 | Bramucci et al. |
| 2008/0132741 A1 | 6/2008 | D'Amore et al. |
| 2008/0182308 A1 | 7/2008 | Donaldson et al. |
| 2008/0274525 A1 | 11/2008 | Bramucci et al. |
| 2008/0274526 A1 | 11/2008 | Bramucci et al. |
| 2009/0171129 A1 | 7/2009 | Evanko et al. |
| 2009/0203099 A1 | 8/2009 | Caimi et al. |
| 2009/0246846 A1 | 10/2009 | Viitanen et al. |
| 2009/0305363 A1 | 12/2009 | Anthony et al. |
| 2009/0305370 A1 | 12/2009 | Grady et al. |
| 2010/0143992 A1 | 6/2010 | Erdner-Tindall et al. |
| 2010/0143993 A1 | 6/2010 | Erdner-Tindall et al. |
| 2010/0143994 A1 | 6/2010 | Erdner-Tindall et al. |
| 2010/0143995 A1 | 6/2010 | Erdner-Tindall et al. |
| 2010/0205857 A1 | 8/2010 | Dijk et al. |
| 2010/0221802 A1 | 9/2010 | Grady et al. |
| 2010/0248233 A1 | 9/2010 | Muller et al. |
| 2010/0298611 A1* | 11/2010 | Parekh et al. ............... 568/840 |
| 2011/0097773 A1 | 4/2011 | Grady et al. |
| 2011/0136193 A1 | 6/2011 | Grady et al. |
| 2011/0162953 A1 | 7/2011 | Xu et al. |
| 2011/0162954 A1 | 7/2011 | Xu et al. |
| 2011/0288344 A1 | 11/2011 | Grady et al. |
| 2011/0288345 A1 | 11/2011 | Grady et al. |
| 2011/0294179 A1 | 12/2011 | Grady et al. |
| 2011/0312043 A1 | 12/2011 | Burlew et al. |
| 2011/0312044 A1 | 12/2011 | Anton et al. |
| 2011/0312053 A1 | 12/2011 | Burlew et al. |
| 2011/0315541 A1 | 12/2011 | Xu |
| 2012/0035398 A1 | 2/2012 | Grady et al. |
| 2012/0156738 A1 | 6/2012 | Anton et al. |
| 2012/0164302 A1 | 6/2012 | Roesch et al. |
| 2012/0208246 A1 | 8/2012 | Anton et al. |
| 2012/0211348 A1 | 8/2012 | Grady et al. |
| 2012/0323047 A1 | 12/2012 | Dauner et al. |
| 2013/0164795 A1 | 6/2013 | Lowe et al. |
| 2013/0217060 A1 | 8/2013 | Bramucci et al. |
| 2013/0224728 A1 | 8/2013 | Bramucci et al. |
| 2013/0236935 A1 | 9/2013 | Burlew et al. |
| 2013/0252297 A1 | 9/2013 | Parten |
| 2013/0295661 A1 | 11/2013 | Roesch et al. |
| 2014/0018581 A1 | 1/2014 | Grady et al. |
| 2014/0024064 A1 | 1/2014 | Burlew et al. |
| 2014/0073021 A1 | 3/2014 | Bazzana et al. |
| 2014/0073820 A1 | 3/2014 | Bazzana et al. |
| 2014/0080189 A1 | 3/2014 | Grady et al. |
| 2014/0093931 A1 | 4/2014 | Dauner et al. |
| 2014/0094630 A1 | 4/2014 | Anton et al. |
| 2014/0099688 A1 | 4/2014 | Grady et al. |
| 2014/0106419 A1 | 4/2014 | Bazzana et al. |
| 2014/0142352 A1 | 5/2014 | Dauner et al. |
| 2014/0162344 A1 | 6/2014 | DiCosimo et al. |
| 2014/0178529 A1 | 6/2014 | Anton et al. |
| 2014/0234929 A1 | 8/2014 | Barr et al. |

FOREIGN PATENT DOCUMENTS

| | | | |
|---|---|---|---|
| WO | WO 2010/075241 | 7/2010 | |
| WO | WO 2010/151832 | 12/2010 | |
| WO | WO 2011/003962 | 1/2011 | |
| WO | WO 2011/063391 | 5/2011 | |
| WO | WO 2011/159967 | * 12/2011 | ............... C12P 7/16 |
| WO | WO 2013/086222 | 6/2013 | |

OTHER PUBLICATIONS

Greer, Digesters Help Fuel Ethanol Facilities, BioCycle Energy, Feb. 2011, Available online at: www.eisenmann.us.com/portals/133998/docs/biocycle_feb2011.pdf.*

ICM, Bio-Methanation: Waste to Energy, 2009, Available online at: www.icminc.com/ images/pdfs/product_sheet/bio-methanation_waste_to_energy_lores.pdf.*

Green, Fermentative production of butanol—the industrial perspective, Curr. Opin. Biotechnol. 22:337-343, 2011.

Larsson, et al., A feasibility study on conversion of an ethanol plant to a butanol plant, Statoil Hydro, Oslo, Norway, May 16, 2008.

Young, et al., Oil-water separation using hydrocyclones: An experimental search for optimum dimensions, J. Petroleum Sci. Eng. 11:37-50, 1994.

Roffler, Extractive fermentation—lactic acid and acetone/butanol production, Dissertation, University of California, Berkeley, 1986.

Zhang, et al., Metabolic Engineering of a Pentose Metabolism Pathway in Ethanologenic Zymomonas mobili, Science 267:240-243, 1995.

Ohta, et al., Genetic Improvement of *Escherichia coli* for Ethanol Production: Chromosomal Integration of Zymomonas mobilis Genes Encoding Pyruvate Decarboxylase . . . Appl. Environ. Microbial. 57:893-900, 1991.

Underwood, et al., Flux through Citrate Synthase Limits the Growth of Ethanologenic *Escherichia coli* KO11 during Xylose Fermentation, Appl. Environ. Microbiol. 68:1071-1081, 2002.

Shen, et al., Metabolic engineering of *Escherichia coli* for 1-butanol and 1-propanol production via the keto-acid pathways, Metab. Eng. 10:312-320, 2008.

Hanai, et al., Engineered Synthetic Pathway for Isopropanol Production in *Escherichia coli*, Appl. Environ. Microbiol. 73:7814-7818, 2007.

Feldmann, et al., Pentose metabolism in Zymomonas mobilis wild-type and recombinant strains, Appl. Microbiol. Biotechnol. 38:354-361, 1992.

Lynd, et al., Microbial Cellulose Utilization: Fundamentals and Biotechnology, Microbiol. Mol. Biol. Rev. 66:506-577, 2002.

Gabriel, Butanol Fermentation Process, Ind. Eng. Chem. 20:1063-1067, 1928.

Hess, BP and DuPont Plan 'Biobutanol' C&E News, Jun. 26, 2006, p. 9.

Maiorella, et al., Biotechnology Report, Economic Evaluation of Alternative Ethanol Fermentation Processes, Biotech. Bioeng. 26:1003-1025, 1984.

Ramey, Butanol: The Other Alternative Fuel, National Agricultural Biotechnology Council Report, NABC Report 19, Proceedings of the Nineteenth Annual Conference of the National Agricultural Biotechnology Council, hosted7by South Dakota State University, Brookings, SD, May 22-24 2007, pp. 137-147.

International Search Report and Written Opinion of corresponding PCT/US2013/039572 mailed Jul. 16, 2013.

U.S. Appl. No. 14/363,360, filed Jun. 6, 2014.
U.S. Appl. No. 13/162,868, filed Jun. 17, 2011.
U.S. Appl. No. 13/326,511, filed Dec. 15, 2011.
U.S. Appl. No. 14/203,809, filed Mar. 11, 2014.
U.S. Appl. No. 14/211,342, filed Mar. 14, 2014.
U.S. Appl. No. 14/213,274, filed Mar. 14, 2014.
U.S. Appl. No. 14/275,432, filed May 12, 2014.
U.S. Appl. No. 14/317,249, filed Jun. 27, 2014.
U.S. Appl. No. 14/320,681, filed Jul. 1, 2014.

* cited by examiner

PROCESSES AND SYSTEMS FOR ALCOHOL PRODUCTION AND RECOVERY

This application claims the benefit of U.S. Provisional Application No. 61/642,757, filed on May 4, 2012; the entire contents of which are herein incorporated by reference.

FIELD OF THE INVENTION

The present invention relates to processes for recovering butanol produced in a fermentative process using, for example, an ethanol production plant which has been reversibly-retrofitted for butanol production, that is, the ethanol production plant may be converted for butanol production, but can also revert to an ethanol production. The present invention also relates to processes for recovering butanol produced in a fermentative process in a butanol production plant that may be converted to ethanol production plant.

BACKGROUND OF THE INVENTION

In the United States, bioethanol is produced by fermentation from sources such as corn at over 100 commercial facilities, and these facilities may also be utilized to commercialize biobutanol technology that involves similar fermentation and distillation operations. Butanol is an alcohol with a variety of applications, such as a fuel additive, a blend component to diesel fuel, a chemical reagent in the plastics industry, and a food grade extractant in the food and flavor industry. Butanol is favored as a fuel or fuel additive because it has a higher energy density than ethanol and yields only $CO_2$ and little or no $SO_X$ or $NO_X$ when burned in the standard internal combustion engine. Additionally, butanol is less corrosive than ethanol. Each year ten to twelve billion pounds of butanol are produced by petrochemical means. As the projected demand for butanol increases, interest in producing butanol from renewable resources such as corn, sugar cane, or cellulosic feeds by fermentation is expanding.

Converting a facility from bioethanol to biobutanol production may involve, for example, retrofitting the equipment and configuration to enable fermentation and purification of butanol; and an objective of this conversion may be minimal use of capital. Retrofitting the equipment may include both modification of existing equipment and installation of new equipment. To minimize loss of operational flexibility, the conversion to a biobutanol plant may be reversible. For example, if there are fluctuations in the biofuel market, the ability to restore the facility to a bioethanol production plant would be advantageous. Depending on circumstances, the facility may revert to its original state prior to the conversion to a biobutanol plant or improvements may also be incorporated in the reversion to a bioethanol production plant. It would also be beneficial to have the ability to convert the reverted bioethanol production plant to a biobutanol production plant, for example, if the demand for bioethanol changes. That is, the retrofit of the bioethanol production plant may be reversible, allowing the facility to be easily converted between a bioethanol production plant and a biobutanol production plant, for example, with little or no loss of operations. Furthermore, in the construction of a biobutanol production plant, it would be advantageous to also incorporate the ability to convert the biobutanol production plant to a bioethanol production plant. If the demand for a biofuel changes, a biofuel production plant that could easily be converted to produce biobutanol, bioethanol, or other biofuel would be valued.

Thus, there is a need for processes and systems for producing butanol using a retrofit of a bioethanol production plant or a newly constructed biobutanol production plant, and a need for processes and systems that may be easily converted to either a bioethanol production plant or a biobutanol production plant. The present application satisfies these and other needs, and provides further related advantages, as will be made apparent by the description of the embodiments herein.

SUMMARY OF THE INVENTION

The present invention is directed to a method for improving the product profile of an ethanol production plant comprising modifying the plant to produce one or more biofuel products other than ethanol wherein the modifications allow the plant to be reverted to ethanol production. In some embodiments, modifying the plant may comprise adding one or more solids separation units, adding one or more extractant columns and/or extractant separation units, repurposing an ethanol beer column for distillation of an alcohol other than ethanol, and reconfiguring an evaporation train. In some embodiments, modifying the plant may comprise adding one or more solids separation units, adding one or more extractant columns and/or extractant separation units, adding one or more condensation units, adding one or more decantation units, repurposing an ethanol beer column for distillation of an alcohol other than ethanol, and reconfiguring an evaporation train. In some embodiments, modifying the plant may comprise adding one or more solids separation units, adding one or more flash units and/or condensation units, repurposing an ethanol beer column for distillation of an alcohol other than ethanol, and reconfiguring an evaporation train. In some embodiments, modifying the plant may comprise adding one or more solids separation units, adding one or more flash units and/or condensation units, adding one or more preflash units and/or compress units, repurposing an ethanol beer column for distillation of an alcohol other than ethanol, and reconfiguring an evaporation train. In some embodiments, modifying the plant may comprise adding one or more solids separation units, adding one or more extractant columns and/or extractant separation, adding one or more hydrolyzers, repurposing an ethanol beer column for distillation of an alcohol other than ethanol, and reconfiguring an evaporation train. In some embodiments, the one or more biofuel products may comprise butanol. In some embodiments, the one or more biofuel products may comprise butanol and fusel oils. In some embodiments, the one or more biofuel product may comprise butanol and oil recovered from a feedstock after the feedstock has been subjected to liquefaction. In some embodiments, the improved product profile may comprise the removal of undissolved solids prior to fermentation. In some embodiments, the removal of undissolved solids provides improved product profiles of the plant including one or more of improved animal feed co-product production and increased biofuel production productivity. In some embodiments, the removal of undissolved solids may be applied before and/or after retrofit of the ethanol plant to produce one or more biofuel products. In some embodiments, the removal of undissolved solids may remain upon reversion of the plant to ethanol production.

The present invention is also directed to a process for producing butanol using a reversibly-retrofitted ethanol production plant comprising providing an ethanol production plant comprising a fermentor, a rectification column, a beer column, and a side stripper, and the fermentor may comprise an external cooling loop for removing a fermentation broth from the fermentor via an exit line, circulating the removed fermentation broth through a heat exchanging device and returning the removed fermentation broth to the fermentor at a lower temperature via a return line; providing an aqueous feedstream obtained from biomass, the aqueous feedstream comprising water and fermentable sugar; contacting the aqueous feedstream with a fermentation broth in the fermentor, the fermentation broth comprising a recombinant microorganism capable of producing butanol; fermenting the fermentable sugar in the fermentor; removing a portion of the fermentation broth including the butanol from the fermentor via an exit line of the external cooling loop; separating the portion of the fermentation broth including the butanol to produce a butanol-rich stream and a butanol-lean stream; returning the butanol-lean stream to the fermentor via a return line of the external cooling loop; distilling at least a portion of the butanol-rich stream in a dehydration column to produce a bottoms stream comprising butanol; discharging a beer stream from the fermentor; and distilling the beer stream in the beer column retrofitted to produce: a butanol-rich vapor stream and a butanol-lean beer bottoms stream. In some embodiments, the recombinant microorganism may produce butanol, and the fermentation broth may comprise butanol. In some embodiments, the rectification column may be retrofitted to serve as a dehydration column. In some embodiments, the process may further comprise reversing the retrofits of the rectification column and the beer column without structural modification to the rectification and beer columns so as to operate the rectification and beer columns for the production of ethanol after operating the rectification and beer columns for the production of butanol. In some embodiments, the step of separating the portion of the fermentation broth including the butanol to produce a butanol-rich stream and a butanol-lean stream may comprise contacting the portion of the fermentation broth with an extractant to form a biphasic mixture comprising an aqueous phase and an organic phase; separating the butanol-containing organic phase and the aqueous phase, the aqueous phase comprising the butanol-lean stream; distilling the butanol-containing organic phase in an extractant column to produce a butanol-rich vapor stream and an extractant-rich bottoms stream; and condensing the butanol-rich vapor stream produced in the extractant column to produce the butanol-rich stream. In some embodiments, the butanol preferentially partitions into the organic phase to form a butanol-containing organic phase. In some embodiments, the contacting the portion of the fermentation broth with an extractant may comprise combining the portion of the fermentation broth with the extractant in a mixing device to form the biphasic mixture, the mixing device being fluidly connected to the return line of the external cooling loop. In some embodiments, the mixing device receives the portion of the fermentation broth via the return line. In some embodiments, the mixing device may comprise inline mixer, a piping tee, or an agitated vessel. In some embodiments, the separating the butanol-containing organic phase and the aqueous phase may comprise adding the biphasic mixture to a separation device in fluid connection with the mixing device and the return line. In some embodiments, the separation device may discharge a first stream comprising the butanol-containing organic phase and a second stream comprising the aqueous phase. In some embodiments, the second stream may be discharged to the return line downstream of the mixing device, whereby the aqueous phase comprising the butanol-lean stream is returned to the fermentor via the return line. In some embodiments, the separation device may comprise a hydrocyclone, an inline vortex separator, a centrifuge, a decanter, or combinations thereof. In some embodiments, the process may further comprise condensing the butanol-rich vapor stream produced in the beer column to produce a butanol-rich liquid stream; and adding the butanol-rich liquid stream to the butanol-rich stream. In some embodiments, the process may further comprise separating the butanol-rich stream into a first stream that is added to the extractant column and a second stream that is added to the dehydration column. In some embodiments, the side stripper may be retrofitted to serve as a dealcoholization column. In some embodiments, the ethanol production plant may further comprise an evaporation system, and the process may further comprise separating the solids and the thin stillage; and evaporating water from the thin stillage to produce a syrup using the evaporation system that has been retrofitted for the production of butanol. In some embodiments, the evaporation system of the ethanol production plant may be configured as a four train, double effect evaporation system having four first effect evaporators and four second effect evaporators and in some embodiments, the evaporation system may be retrofitted to include an additional evaporator and to be reconfigured as a three train, triple effect evaporation system. In some embodiments, the evaporation system of the ethanol production plant may be configured as a four train, double effect evaporation system having four first effect evaporators and four second effect evaporators, and in some embodiments, the evaporation system may be retrofitted to include one or more additional evaporators and to be reconfigured as a triple effect evaporation system having four evaporators in a first effect, four evaporators in a second effect, and the one or more additional evaporators in a third effect. In some embodiments, the process may further comprises drying the separated solids and the syrup to produce DDGS.

The present invention is directed to a process for producing butanol using a reversibly-retrofitted ethanol production plant comprising providing an ethanol production plant comprising a fermentor, a side stripper, a rectification column, and a beer column; providing an aqueous feedstream obtained from biomass, the aqueous feedstream comprising water and fermentable sugar; contacting the aqueous feedstream with a fermentation broth in the fermentor, the fermentation broth comprising a recombinant microorganism capable of producing butanol; batch fermenting the fermentable sugar in the fermentor; separating the fermentation broth including the butanol to produce a butanol-rich stream and butanol-lean stream; distilling at least a portion of the butanol-rich stream in a dehydration column to produce a bottoms stream comprising butanol; and distilling the beer stream in the beer column retrofitted to produce: a butanol-rich vapor stream and a butanol-lean beer bottoms stream. In some embodiments, the recombinant microorganism produces butanol, and the fermentation broth comprises butanol. In some embodiments, the rectification column may be retrofitted to serve as the dehydration column and/or the side stripper may be retrofitted to serve as a dealcoholization column. In some embodiments, the step of separating the fermentation broth including the butanol to produce an butanol-rich stream and a beer stream may comprise contacting the fermentation broth with an extractant to form a biphasic mixture comprising an aqueous phase and an organic phase; separating the butanol-containing organic phase and the aqueous phase, the aqueous phase comprising the butanol-lean stream; distilling the butanol-containing organic phase in an extractant column to produce a butanol-rich vapor stream and an extractant-rich bottoms stream; and condensing the butanol-rich vapor stream to produce the butanol-rich stream. In some embodiments, the butanol preferentially partitions into the organic phase to form a butanol-containing organic phase. In some embodiments, the ethanol production plant may further comprise an external cooling loop for removing the fermentation broth from the fermentor via an exit line, circulating the removed fermentation broth through a heat exchanging device and returning the removed fermentation broth to the fermentor at a lower temperature via a return line. In some embodiments, the contacting the fermentation broth with an extractant may comprise adding the extractant to the fermentor via the return line of the cooling loop. In some embodiments, the extractant enters the return line via a line that is joined to one of the exit line and the return line of the cooling loop. In some embodiments, the contacting the fermentation broth with an extractant further may comprise mixing the extractant with the fermentation broth. In some embodiments, the mixing may be at least partially achieved by evolution and release of carbon dioxide gas in the fermentor. In some embodiments, the mixing may be entirely achieved by the evolution and release of carbon dioxide gas in the fermentor. In some embodiments, the mixing may be partially achieved by agitating the biphasic mixture using a mechanical agitation device. In some embodiments, the separating the butanol-containing organic phase and the aqueous phase may comprise adding the biphasic mixture to a separation device. In some embodiments, the separation device may discharge a first stream comprising the butanol-containing organic phase and a second stream comprising the aqueous phase, the aqueous phase comprising the butanol-lean stream. In some embodiments, the separation device may comprise a hydrocyclone, an inline vortex separator, a centrifuge, a decanter, or combinations thereof. In some embodiments, the ethanol production plant may further comprise a beer well fluidly interposed between the fermentor and the beer column, a first line connecting the fermentor to the beer well, and a second line connecting the beer well to the beer column. In some embodiments, the separation device may be disposed on the first line so as to be fluidly interposed between the fermentor and the beer well and the process may further comprise adding the second stream comprising the butanol-lean stream from the separation device to the beer well via the first line and from the beer well to the beer column via the second line. In some embodiments, the ethanol production plant may further comprise a beer well fluidly interposed between the fermentor and the beer column, a first line connecting the fermentor to the beer well, and a second line connecting the beer well to the beer column. In some embodiments, a heat exchanger may be disposed on the second line and/or the separation device may be disposed on the second line so as to be fluidly interposed between the beer well and the beer column downstream of the heat exchanger. In some embodiments, the process may further comprise adding the biphasic mixture to the beer well via the first line. In some embodiments, the adding the biphasic mixture to a separation device may comprise adding the biphasic mixture from the beer well to the separation device via the second line. In some embodiments, the adding the biphasic mixture may pass through the heat exchanger and may be heated prior to being fed to the separation device. In some embodiments, the process may further comprise condensing the butanol-rich vapor stream produced in the beer column to produce a butanol-rich liquid stream; and adding the butanol-rich liquid stream to the butanol-rich stream. In some embodiments, the process may further comprises separating the butanol-rich stream into a first stream that is added to the extractant column and a second stream that is added to the dehydration column. In some embodiments, the beer bottoms may comprise solids and thin stillage, and the ethanol production plant may further comprise an evaporation system; the process further comprising separating the solids and the thin stillage and evaporating water from the thin stillage to produce a syrup using the evaporation system that has been retrofitted for the production of butanol. In some embodiments, the evaporation system of the ethanol production plant may be configured as a four train, double effect evaporation system having four first effect evaporators and four second effect evaporators, and the evaporation system may be retrofitted to include an additional evaporator and to be reconfigured as a three train, triple effect evaporation system. In some embodiments, the evaporation system of the ethanol production plant may be configured as a four train, double effect evaporation system having four first effect evaporators and four second effect evaporators, and the evaporation system may be retrofitted to include one or more additional evaporators and to be reconfigured as a triple effect evaporation system having four evaporators in a first effect, four evaporators in a second effect, and the one or more additional evaporators in a third effect. In some embodiments, the process may further comprise drying the separated solids and the syrup to produce DDGS.

The present invention is also directed to a process for producing butanol using a reversibly-retrofitted ethanol production plant comprising providing an ethanol production plant comprising a fermentor, a side stripper, a rectification column, and a beer column; providing an aqueous feedstream obtained from biomass, the aqueous feedstream comprising water and fermentable sugar; contacting the aqueous feedstream with a fermentation broth in the fermentor, the fermentation broth comprising a recombinant microorganism capable of producing butanol; batch fermenting the fermentable sugar in the fermentor; contacting the fermentation broth with an extractant to form a biphasic mixture comprising an aqueous phase and an organic phase; distilling at least a portion of the biphasic mixture in the beer column retrofitted to produce a butanol-rich vapor stream and an butanol-lean beer bottoms stream, and the butanol-lean beer bottoms stream may comprise extractant, thin stillage, and solids; condensing the butanol-rich vapor stream produced in the beer column to produce a butanol-rich liquid stream; separating the butanol-rich liquid stream into a second butanol-rich liquid stream and a butanol-lean liquid stream; distilling the second butanol-rich liquid stream in a dehydration column to produce a bottoms stream comprising butanol; and separating the butanol-lean beer bottoms stream to produce thin stillage, solids, and recovered extractant. In some embodiments, the recombinant microorganism produces butanol, and the fermentation broth comprises butanol. In some embodiments, the butanol preferentially partitions into the organic phase to form a butanol-containing organic phase. In some embodiments, the rectification column may be retrofitted to serve as the dehydration column and/or the side stripper may be retrofitted to serve as a dealcoholization column. In some embodiments, the separating the butanol-lean beer bottoms stream may comprise separating the butanol-lean beer bottoms stream in a first separation device to produce an extractant stream, and a thin stillage and solids stream and separating the thin stillage and solids stream in a second separation device to produce thin stillage and solids. In some embodiments, the first separation device may comprise a hydrocyclone, an inline vortex separator, a centrifuge, a decanter, or combination thereof. In some embodiments, the ethanol production plant may comprise a centrifuge, and the second separation device may be a centrifuge. In some embodiments, separating the butanol-lean beer bottoms stream may comprise separating the butanol-lean beer bottoms stream in a first separation device to produce solids, and a thin stillage and extractant stream and separating the thin stillage and extractant stream in a second separation device to produce thin stillage and extractant. In some embodiments, the second separation device may comprise a hydrocyclone, an inline vortex separator, a centrifuge, a decanter, or combinations thereof. In some embodiments, the second separation device may be a decanter. In some embodiments, the ethanol production plant may comprise a centrifuge and the first separation device may be a centrifuge. In some embodiments, the separating the butanol-lean beer bottoms stream may comprises separating the solids, the thin stillage, and the extractant in a three-phase centrifuge. In some embodiments, the process may further comprise distilling a first portion of the biphasic mixture formed in the beer column; distilling a second portion of the biphasic mixture in an extractant column to produce a second butanol-rich vapor stream and a second butanol-lean beer bottoms stream; and combining the second butanol-lean beer bottoms stream with the butanol-lean beer bottoms stream. In some embodiments, the second butanol-lean beer bottoms stream may comprise extractant, thin stillage, and solids. In some embodiments, the ethanol production plant may further comprise an evaporation system and the process may further comprise after separating the butanol-lean beer bottoms stream to produce solids, extractant, and thin stillage, evaporating water from the thin stillage to produce a syrup using the evaporation system that has been retrofitted for the production of butanol. In some embodiments, the evaporation system of the ethanol production plant may be configured as a four train, double effect evaporation system having four first effect evaporators and four second effect evaporators, and the evaporation system may be retrofitted to include an additional evaporator and to be reconfigured as a three train, triple effect evaporation system. In some embodiments, the evaporation system of the ethanol production plant may be configured as a four train, double effect evaporation system having four first effect evaporators and four second effect evaporators, and the evaporation system may be retrofitted to include one or more additional evaporators and to be reconfigured as a triple effect evaporation system having four evaporators in a first effect, four evaporators in a second effect, and the one or more additional evaporators in a third effect. In some embodiments, the process may further comprise drying the solids and the syrup to produce DDGS. In some embodiments, the ethanol production plant may further comprise an external cooling loop for removing a fermentation broth from the fermentor via an exit line, circulating the removed fermentation broth through a heat exchanging device and returning the removed fermentation broth to the fermentor at a lower temperature via a return line, and the contacting the fermentation broth with an extractant may comprise adding the extractant to the fermentor via a line fluidly connected to one of the exit line and the return line of the external cooling loop.

The present invention is directed to a process for producing butanol using a reversibly-retrofitted ethanol production plant comprising providing an ethanol production plant comprising a fermentor, a side stripper, a rectification column, and a beer column; providing an aqueous feedstream obtained from biomass, the aqueous feedstream comprising water and fermentable sugar; contacting the aqueous feedstream with a fermentation broth in the fermentor, the fermentation broth comprising a recombinant microorganism capable of producing butanol; fermenting the fermentable sugar in the fermentor; contacting the fermentation broth including the butanol with fatty acids and a catalyst which catalyzes the esterification of the fatty acids and the butanol in the fermentor to produce butyl esters, whereby the fermentation broth comprises butyl esters; removing the fermentation broth including the butyl esters from the fermentor; separating the fermentation broth including the butyl esters to produce a fatty ester stream and thin stillage; reacting the fatty ester stream to produce a composition comprising butanol and fatty acids; distilling the composition to produce a butanol-rich vapor stream and a fatty acid stream; condensing the butanol-rich vapor stream to produce a butanol-rich stream; separating the butanol-rich stream to produce a second butanol-rich stream and a butanol-lean stream; distilling the second butanol-rich stream in a dehydration column to produce a bottoms stream comprising butanol; reacting the thin stillage to produce a reaction composition comprising butanol and fatty acids; and distilling the reaction composition in the beer column retrofitted to produce: a butanol-rich vapor stream and a butanol-lean beer bottoms stream. In some embodiments, the recombinant microorganism produces butanol, whereby the fermentation broth comprises butanol. In some embodiments, the fermentable sugar may be batch fermented in the fermentor. In some embodiments, the rectification column may be retrofitted to serve as the dehydration column and/or the side stripper may be retrofitted to serve as a dealcoholization column. In some embodiments, the process may further comprise recovering the fatty acids from the fatty acid stream. In some embodiments, the process may further comprise repeating the steps of the process, a second aqueous feedstream may be provided as an aqueous feedstream, and/or recovered fatty acids may be contacted with the fermentation broth. In some embodiments, the separating the fermentation broth including the butyl esters may comprise adding the fermentation broth including the butyl esters to a separation device which discharges a first stream comprising the fatty esters and a second stream comprising thin stillage. In some embodiments, the separation device may comprise a hydrocyclone, an inline vortex separator, a centrifuge, a decanter, or combinations thereof.

The present invention is also directed to a system for producing butanol using a reversibly-retrofitted ethanol production plant comprising an ethanol production plant comprising a fermentor, a side stripper, a rectification column, and a beer column, and the fermentor may comprise an external cooling loop for removing a fermentation broth from the fermentor via an exit line, circulating the removed fermentation broth through a heat exchanging device and returning the removed fermentation broth to the fermentor at a lower temperature via a return line, and the beer column may be retrofitted for stripping butanol from a beer stream discharged from the fermentor, the beer column having an outlet for discharging a butanol-rich vapor stream and an outlet for discharging a butanol-lean beer bottoms stream; a mixing device having a first inlet connected to the return line of the external cooling loop for receiving the removed fermentation broth from the fermentor, a second inlet connected to an extractant line configured to contain an extractant stream, and an outlet connected to a mixed stream line configured to contain a mixed stream of the removed fermentation broth and the extractant; an extractant line for discharging an organic stream; an extractant column having an inlet connected to the second extractant line for receiving the organic stream, an outlet for discharging an extractant-lean, butanol-rich vapor stream, and an outlet for discharging an extractant-rich, butanol-lean stream; a condenser fluidly connected to an outlet of the beer column and an outlet of the extractant column, the condenser configured to condense the butanol-rich vapor stream to produce a stream comprising butanol; a decanter fluidly connected to the condenser that separates the stream comprising butanol to produce a butanol-rich stream and a butanol-lean stream; and a dehydration column fluidly connected to the decanter that is configured to distill the butanol-rich stream to produce butanol, the dehydration column having an outlet that discharges butanol. In some embodiments, the rectification column may be retrofitted to serve as the dehydration column and/or the side stripper may be retrofitted to serve as a dealcoholization column. In some embodiments, the mixing device may comprise an inline mixer, a piping tee, or an agitated vessel. In some embodiments, the separation device may comprise a hydrocyclone, an inline vortex separator, a centrifuge, a decanter, or combination thereof. In some embodiments, the extractant column may be operated in parallel with the beer column.

The present invention is also directed to a system for producing butanol using a reversibly-retrofitted ethanol production plant comprising an ethanol production plant comprising a fermentor, a side stripper, a rectification column, and a beer column, and the fermentor may comprise an external cooling loop for removing a fermentation broth from the fermentor via an exit line, circulating the removed fermentation broth through a heat exchanging device and returning the removed fermentation broth to the fermentor at a lower temperature via a return line, and the external cooling loop may be retrofitted to conduct an extractant to the fermentor for contacting with the fermentation broth, and the beer column may be retrofitted for stripping butanol from a beer stream discharged from the fermentor, the beer column having an outlet for discharging a butanol-rich vapor stream and an outlet for discharging a butanol-lean beer bottoms stream; an extractant column fluidly connected to the fermentor for receiving an organic stream, the extractant column having an outlet for discharging an extractant-lean, butanol-rich vapor stream, and an outlet for discharging an extractant-rich, butanol-lean stream; a condenser fluidly connected to an outlet of the beer column and an outlet of the extractant column, the condenser configured to condense the butanol-rich vapor stream to produce a stream comprising butanol; a decanter fluidly connected to the condenser that separates the stream comprising butanol to produce a butanol-rich stream and a butanol-lean stream; and a dehydration column fluidly connected to the decanter that is configured to distill the butanol-rich stream to produce butanol, the dehydration column having an outlet that discharges butanol. In some embodiments, the rectification column may be retrofitted to serve as the dehydration column and/or the side stripper may be retrofitted to serve as a dealcoholization column. In some embodiments, the system may further comprise a separation device fluidly interposed between the fermentor, the extractant column, and the beer column, the separation device having an inlet fluidly connected to the fermentor for receiving a biphasic mixture from the fermentor, a first outlet fluidly connected to the beer column for discharging the beer stream to the beer column, and a second outlet fluidly connected to the extractant column for discharging the organic stream to the extractant column. In some embodiments, the ethanol production plant may further comprise a beer well fluidly interposed between the fermentor and the beer column, a first line connecting the fermentor to the beer well, and a second line connecting the beer well to the beer column, and the separation device may be disposed on the first line so as to be fluidly interposed between the fermentor and the beer well, and the first outlet of the separation device is connected to the beer well for discharging the beer stream to the beer well. In some embodiments, the beer well may comprise an outlet connected to the second line for discharging the beer stream to the beer column. In some embodiments, the ethanol production plant may further comprise a beer well fluidly interposed between the fermentor and the beer column, a first line connecting the fermentor to the beer well, the beer well receiving the biphasic mixture from the fermentor via the first line, and a second line connecting the beer well to the beer column. In some embodiments, a heat exchanger may be disposed on the second line. In some embodiments, the separation device may be disposed on the second line so as to be fluidly interposed between the beer well and the beer column downstream of the heat exchanger. In some embodiments, the inlet of the separation device may be connected to the second line for receiving the biphasic mixture from the beer well, and the first outlet may be connected to the second line downstream of the inlet of the separation device for discharging the beer stream to the beer column. In some embodiments, the separation device may comprise a hydrocyclone, an inline vortex separator, a centrifuge, a decanter, or combinations thereof. In some embodiments, the organic stream may comprise butyl esters, and the system may further comprise a reactor fluidly interposed between the extractant column and the fermentor, the reactor having an inlet for receiving the organic stream. In some embodiments, the reactor may be configured to react the butyl esters in the organic stream to produce a reaction composition comprising butanol and extractant. In some embodiments, the extractant column may be a regeneration column configured to separate the reaction composition into a butanol-rich vapor stream and an extractant-rich stream. In some embodiments, the extractant column is operated in parallel with the beer column.

The present invention is directed to a system for producing butanol using a reversibly-retrofitted ethanol production plant comprising an ethanol production plant comprising a fermentor, side stripper, a rectification column, and a beer column, and the fermentor may comprise an external cooling loop for removing a fermentation broth from the fermentor via an exit line, circulating the removed fermentation broth through a heat exchanging device and returning the removed fermentation broth to the fermentor at a lower temperature via a return line, and the external cooling loop may be retrofitted to conduct an extractant to the fermentor for contacting with the fermentation broth, and the beer column may be retrofitted for stripping butanol from a biphasic mixture discharged from the fermentor, the beer column having an outlet for discharging a butanol-rich vapor stream and an outlet for discharging a butanol-lean beer bottoms stream; an extractant column having an inlet for receiving the butanol-lean beer bottoms stream, an outlet for discharging recovered extractant, and an outlet for discharging an extractant-lean beer bottoms; a condenser fluidly connected to the outlet of the beer column, the condenser configured to condense the butanol-rich vapor stream to produce a butanol-rich stream; a decanter fluidly connected to the condenser that separates the butanol-rich stream to produce a second butanol-rich stream and a butanol-lean stream; and a dehydration column fluidly connected to the decanter that is configured to distill the second butanol-rich stream to produce butanol, the dehydration column having an outlet that discharges butanol. In some embodiments, the rectification column may be retrofitted to serve as the dehydration column and/or the side stripper is retrofitted to serve as a dealcoholization column. In some embodiments, the separation device comprises a hydrocyclone, an inline vortex separator, a centrifuge, a decanter, or combinations thereof. In some embodiments, the separation device may be a three-phase centrifuge. In some embodiments, the system may further comprise a second separation device fluidly interposed between the first separation device and the beer column. In some embodiments, the second separation device may comprise an inlet connected to the beer column outlet for discharging a butanol-lean beer bottoms stream, a first outlet for discharging solids removed from the beer bottoms, and a second outlet for discharging the remaining beer bottoms comprising a mixture of extractant and thin stillage. In some embodiments, the inlet of the first separation device may be connected to the second outlet of the second separation device for receiving the mixture of extractant and thin stillage, and in some embodiments, the first outlet of the first separation device may discharge the extractant, and the second outlet of the first separation device may discharge the thin stillage. In some embodiments, the second separation device may comprise a hydrocyclone, a centrifuge, or a decanter. In some embodiments, the second separation device is the centrifuge of the ethanol production plant. In some embodiments, the first separation device is a decanter. In some embodiments, the system may further comprise a second separation device having an inlet connected to the second outlet of the first separation device for receiving the extractant-lean beer bottoms, a first outlet for discharging thin stillage, and a second outlet for discharging solids removed from the beer bottoms.

DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

DESCRIPTION OF THE INVENTION

Figure 1:
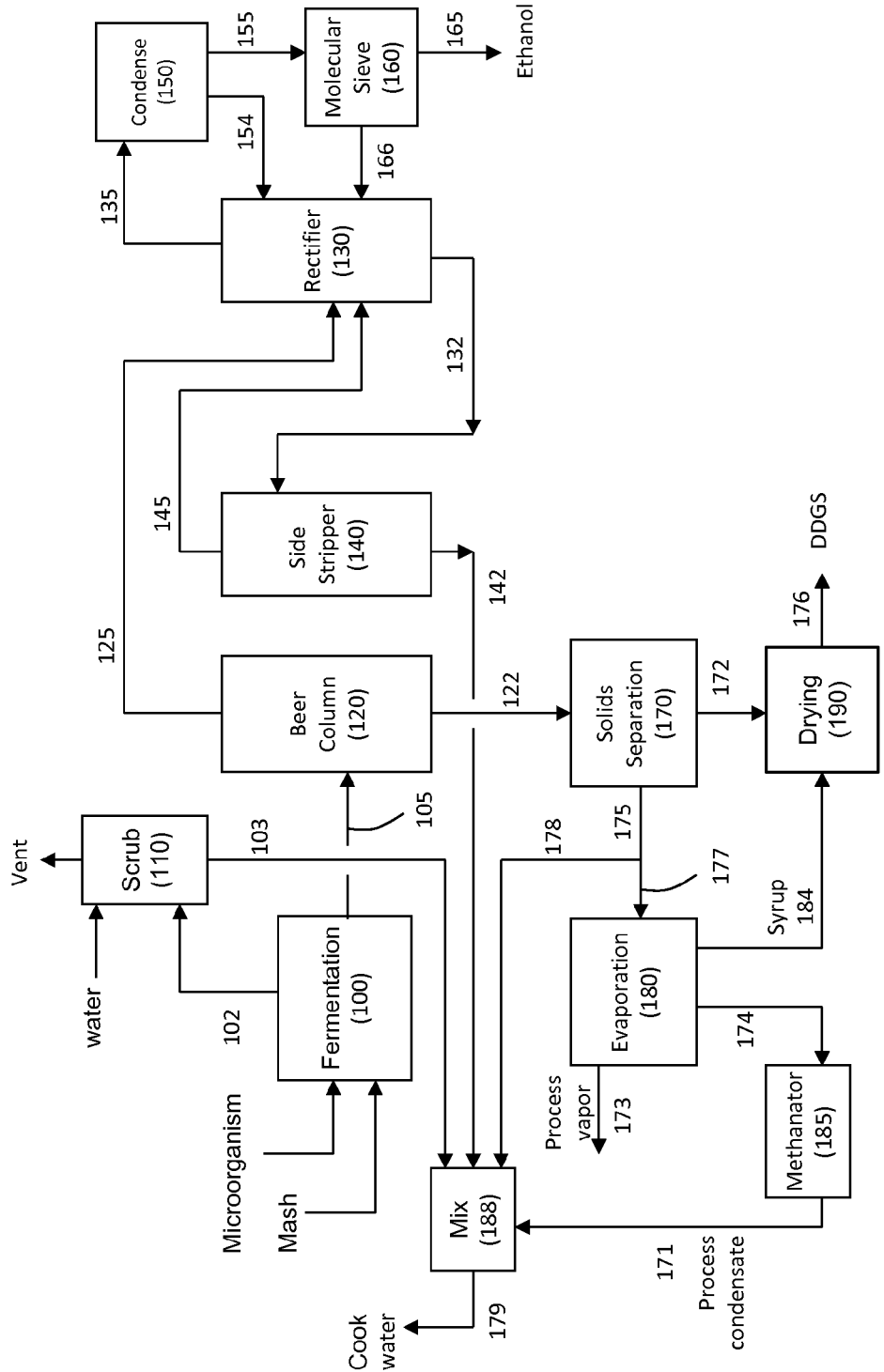
FIG. 1 illustrates an example of a bioethanol production plant.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents, and other references mentioned herein are incorporated by reference in their entireties for all purposes.

In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product comprising hydrolysable polysaccharides that provide fermentable sugars, including any sugars and starch derived from natural resources such as corn, sugar cane, wheat, cellulosic or lignocellulosic material, and materials comprising cellulose, hemicellulose, lignin, starch, oligosaccharides, disaccharides, monosaccharides, and mixtures thereof. Biomass may also comprise additional components, such as protein and/or lipids. Biomass may be derived from a single source or biomass may comprise a mixture derived from more than one source, for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacturing, yard waste, waste sugars, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, soy, whey, whey permeate, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing biomass for purposes of fermentation, such as by milling, treating, and/or liquefying. For example, corn may be processed by wet milling or dry milling and subsequently liquefied to produce mash. Cellulosic and/or lignocellulosic biomass may be processed to obtain a hydrolysate containing fermentable sugars by any method known to one skilled in the art (see, e.g., U.S. Patent Application Publication No. 2007/0031918; the entire contents of which are herein incorporated by reference). Enzymatic saccharification of cellulosic and/or lignocellulosic biomass makes use of an enzyme consortium (e.g., cellulases, xylanases, glucosidases, glucanases, lyases) for breaking down cellulose and hemicellulose to produce a hydrolysate containing sugars including glucose, xylose, and arabinose. Saccharification enzymes suitable for cellulosic and/or lignocellulosic biomass are reviewed in Lynd, et al., (Microbiol. Mol. Biol. Rev. 66:506-577, 2002).

"Biomass yield" as used herein refers to the ratio of biomass produced (i.e., cell biomass production) to carbon substrate consumed.

"Biofuel" or "biofuel product" as used herein refers to a fuel derived from a biological process, for example, but not limited to, fermentation.

"Butanol" as used herein refers to the butanol isomers 1-butanol (1-BuOH), 2-butanol (2-BuOH), tert-butanol (t-BuOH), and/or isobutanol (iBuOH or i-BuOH, also known as 2-methyl-1-propanol), either individually or as mixtures thereof. From time to time, as used herein the term "biobutanol" may be used synonymously with "butanol."

"Product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, and pentanol. Likewise $C_2$ to $C_8$ alkyl alcohols include, but are not limited to, ethanol, propanol, butanol, and pentanol. In some embodiments, product alcohol may also include fusel alcohols (or fusel oils). "Alcohol" is also used herein with reference to a product alcohol.

"In situ Product Removal" (ISPR) as used herein refers to the selective removal of a specific product from a biological process such as fermentation to control the product concentration in the biological process as the product is produced.

"Fermentable carbon source" or "fermentable carbon substrate" as used herein refers to a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; one carbon substrates including methane; and mixtures thereof.

"Feedstock" as used herein means a feed in a fermentation process, the feed containing a fermentable carbon source with or without undissolved solids, and where applicable, the feed containing the fermentable carbon source before or after the fermentable carbon source has been liberated from starch or obtained from the hydrolysis of complex sugars by further processing such as by liquefaction, saccharification, or other process. Feedstock includes or is derived from a biomass. Suitable feedstocks include, but are not limited to, rye, wheat, corn, corn mash, cane, cane mash, barley, cellulosic material, lignocellulosic material, or mixtures thereof. Where reference is made to "feedstock oil," it will be appreciated that the term encompasses the oil produced from a given feedstock.

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

"Fermentable sugar" as used herein refers to one or more sugars capable of being metabolized by the microorganisms disclosed herein for the production of fermentative alcohol.

"Undissolved solids" as used herein means non-fermentable portions of feedstock, for example, germ, fiber, and gluten and any additional components that do not dissolve in aqueous media. For example, the non-fermentable portions of feedstock include the portion of feedstock that remains as solids and can absorb liquid from the fermentation broth.

"Oil" as used herein refers to lipids obtained from plants (e.g., biomass) or animals. Examples of oils include, but are not limited to, tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, and vegetable oil blends.

"Dried Distillers' Grains with Solubles" (DDGS) as used herein refers to a co-product or byproduct from a fermentation of a feedstock or biomass (e.g., fermentation of grain or grain mixture that produces a product alcohol). In some embodiments, DDGS may also refer to an animal feed product produced from a process of making a product alcohol (e.g., ethanol, butanol, isobutanol, etc.).

"Fermentation broth" as used herein means a mixture of water, sugars, dissolved solids, optionally microorganisms producing alcohol, optionally product alcohol, and other constituents. In some embodiments, fermentation broth refers to the material held in the fermentor in which product alcohol is being made by the reaction of sugars to alcohol, water, and carbon dioxide ($CO_2$) by the microorganisms present. From time to time, as used herein the term "fermentation medium" and "fermented mixture" can be used synonymously with "fermentation broth."

"Fermentor" or "fermentation vessel" as used herein refers to a unit in which the fermentation reaction is carried out whereby product alcohol such as butanol is made from sugars.

"Saccharification unit" as used herein refers to a unit in which saccharification (i.e., the hydrolysis of oligosaccharides into monosaccharides) is carried out. Where fermentation and saccharification occur simultaneously, the saccharification unit and the fermentor may be one in the same unit.

"Liquefaction unit" as used herein refers to a unit in which liquefaction is carried out. Liquefaction is the process in which oligosaccharides are released from the feedstock. In some embodiments where the feedstock is corn, oligosaccharides are released from the corn starch content during liquefaction.

"Separation" as used herein refers to removing a chemical compound from an initial mixture to obtain the compound in greater purity or at a higher concentration than the purity or concentration of the compound in the initial mixture. In some embodiments, separation may be synonymous with "recovery."

"Water-immiscible" as used herein refers to a chemical component, such as an extractant, which is incapable of mixing with an aqueous solution, such as a fermentation broth, in such a manner as to form one liquid phase.

"Extractant" as used herein refers to a solvent used to remove or separate a product alcohol such as butanol. From time to time, as used herein the term "solvent" may be used synonymously with "extractant."

"Aqueous phase" as used herein refers to the aqueous phase of a biphasic mixture obtained by contacting a fermentation broth with a water-immiscible organic extractant. In an embodiment of a process described herein that includes fermentative extraction, the term "fermentation broth" then refers to the aqueous phase in biphasic fermentative extraction, and the term "solvent-poor phase" may be used synonymously with "aqueous phase" and "fermentation broth." Also, from time to time, as used herein the term "aqueous stream" may be used synonymously with "aqueous phase." In addition, undissolved solids (e.g., grain solids) may be present in the fermentation broth, such that the biphasic mixture includes the undissolved solids which are primarily dispersed in the aqueous phase.

"Organic phase" as used herein refers to the non-aqueous phase of a biphasic mixture obtained by contacting a fermentation broth with a water-immiscible organic extractant. From time to time, as used herein the term "solvent-rich phase" may be used synonymously with "organic phase." Also, from time to time, as used herein the term "organic stream" may be used synonymously with "organic phase."

"Fatty acid" as used herein refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid may also encompasses free fatty acids.

"Fatty alcohol" as used herein refers to an alcohol having an aliphatic chain of $C_4$ to $C_{22}$ carbon atoms, which is either saturated or unsaturated.

"Fatty aldehyde" as used herein refers to an aldehyde having an aliphatic chain of $C_4$ to $C_{22}$ carbon atoms, which is either saturated or unsaturated.

"Fatty amide" as used herein refers to an amide having a long, aliphatic chain of $C_4$ to $C_{22}$ carbon atoms, which is either saturated or unsaturated.

"Fatty ester" as used herein refers to an ester having a long aliphatic chain of $C_4$ to $C_{22}$ carbon atoms, which is either saturated or unsaturated.

"Carboxylic acid" as used herein refers to any organic compound with the general chemical formula —COOH in which a carbon atom is bonded to an oxygen atom by a double bond to make a carbonyl group (—C=O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

"Stripping" as used herein refers to the action of transferring all or part of a volatile component from a liquid stream into a gaseous stream.

"Vacuum flash" or "flash" as used herein refers to a process step whereby a liquid stream is subjected to a reduction in pressure (e.g., held under vacuum). The liquid stream may be from a fermentor or separate unit such as a pre-flash tank. The reduction in pressure causes a fraction of the liquid stream to vaporize into a vapor phase. A liquid stream subjected to this step may be referred to as "flashed," "partially vaporized," or "vaporized." In some embodiments, the liquid stream from a fermentor may be passed to a separate unit (which can be a multi-stage distillation column or a single-stage tank) which may be held under vacuum. In some embodiments, the liquid stream may be fermentation broth in a fermentor. In some embodiments, the flash may be conducted in a fermentor. In some embodiments where the "flash" is carried out in a multi-stage distillation column, the flash may also be referred to as "distillation" or "flash distillation."

"Flash tank" or "flash unit" as used herein refers to the physical location in which at least a fraction of a liquid stream flashes into the vapor phase.

"Pre-flash" as used herein refers to a process step, prior to a flash step, whereby a liquid stream is subjected to a reduction in pressure (e.g., held under vacuum). The reduction in pressure causes a fraction of the liquid stream to vaporize into a vapor phase. The liquid stream may be from a fermentor or separate unit. A liquid stream subjected to this step may be referred to as "pre-flashed." In some embodiments, there may be two or more pre-flash steps.

"Pre-flash tank" or "pre-flash unit" as used herein refers to the physical location in which at least a fraction of a liquid stream vaporizes into a vapor phase.

"Non-condensable gas" as used herein refers to a gas that is not condensed at an operating temperature of the process described herein. Such gases may be selected from gases in the group consisting of, for example, carbon dioxide, nitrogen, hydrogen, Noble gases such as argon, or mixtures of any of these.

"Revertible retrofit" as used herein refers to conversion of a facility or production plant to its original state, that is, the facility is restored to its original state prior to a retrofit. In some embodiments, improvements to the facility may also be incorporated in a revertible retrofit.

"Reversible retrofit" as used herein refers to conversion of a revertible retrofit to its retrofit state. As an example, a retrofit of a bioethanol production plant may be reversible, allowing the facility to be converted between a bioethanol production plant and a biobutanol production plant.

"Portion" or "portion thereof" as used herein includes a part of a whole or the whole. For example, a portion of fermentation broth includes a part of the fermentation broth as well as the whole (or all) the fermentation broth.

"Substantially" as used herein with reference to a process stream or a component thereof, refers to at least about 50% of the indicated process stream or indicated component thereof.

"Substantial portion" as used herein with reference to a process stream or a component thereof, refers to at least about 50% of the indicated process stream or indicated component thereof. In some embodiments, a substantial portion may comprise at least about 60%, at least about 70%, at least about 80%, at least about 90%, or at least about 95% or the indicated process stream or indicated component thereof. In some embodiments, a substantial portion may comprise at least about 60%, at least about 70%, at least about 80%, at least about 90%, or at least about 95% or the indicated process stream or indicated component thereof.

"Partition coefficient" as used herein refers to the ratio of the concentration of a compound in the two phases of a mixture of two immiscible solvents at equilibrium. A partition coefficient is a measure of the differential solubility of a compound between two immiscible solvents. Partition coefficient, as used herein, may be synonymous with the term "distribution coefficient."

In some embodiments, the present invention provides processes and systems for recovering a product alcohol produced in a fermentative process using a reversibly-retrofitted alcohol (e.g., ethanol) production plant. FIG. 1 illustrates an example of a bioethanol production plant (also, see, e.g., U.S. Pat. No. 7,297,236). Ethanol may be produced by fermentation of sugars in fermentation 100. These fermentable sugars may be derived from any biomass source including corn, cane, cellulosic, or lignocellulosic material. This biomass may be processed, for example, by liquefaction and/or saccharification to form a mash that is fermented by a microorganism such as yeast. In some embodiments, the biomass may be subjected to simultaneous saccharification and fermentation (SSF). Gases 102 generated during the fermentation may be vented to scrub system 110. Water may be contacted with gases 102 in scrub system 110 and bottoms stream 103 results which may be recycled as scrubber water for mashing biomass. Fermentation stream 105 may be transferred to beer column 120. Ethanol and water may be vaporized within beer column 120, and ethanol-rich vaporized stream 125 may be sent overhead to rectifier 130 to concentrate the ethanol. Bottoms stream 122 of beer column 120 is whole stillage, which contains mostly solids (e.g., undissolved solids) and water. Bottoms stream 132 of rectifier 130 may be circulated to side stripper column 140 to recover additional ethanol in overhead vapor product stream 145 which may then be returned to rectifier 130. Bottoms 142 of side stripper column 140 may be recycled as lutter water for processing biomass. Ethanol-rich vaporized stream 135 from rectifier 130 may be directed to condense 150 and a portion 154 of the condensed vapors may be returned to rectifier 130 as reflux. Liquid stream 155 from condense 150 may be transferred to molecular sieve system 160 to adsorb water and yield high grade ethanol vapor product 165 which may be cooled and condensed to produce ethanol. Molecular sieve 160 may be regenerated by removing the adsorbed water via regeneration stream 166 which can include some ethanol. Regeneration stream 166 may be cooled and/or condensed and returned to rectifier 130. If non-condensable gases are present in the rectifier column, these gases may be recovered from condense 150 and sent to a scrubber or thermal oxidizer.

Bottoms stream 122 of beer column 120 may be processed in solids separation 170 by a number of means including, but not limited to, centrifugation, filtration, screen separation, hydrocyclone, or any other means for separating liquids from solids. In some embodiments, solids separation 170 may also comprise one or more conveyors. Separation of bottoms stream 122 produces liquid stream 175 known as thin stillage and solids 172 (e.g., wet cake). A portion 177 of thin stillage 175 may be conducted to evaporation 180 (e.g., four (4) effect by two (2) body system) for water removal and a portion 178 may be recycled as backset for mashing biomass. The evaporators incrementally evaporate water from stream 177 to produce syrup 184 which with wet cake 172 may be further processed in drying system 190 to yield DDGS 176. A portion of the water evaporated in evaporation 180 may be removed as process vapor 173 and may be used to provide boilup in a stripping column. Another portion of the water evaporated in evaporation 180 may be removed as process condensate 174 and may be further processed in methanator 185 to reduce the level of organics. The resulting stream 171 may be recycled as process condensate for mashing biomass. Sources of liquid for mashing biomass including streams 103, 142, 171, and 178 may be combined by mixing 188 with additional water streams to form cook water stream 179 that may be used to mash biomass.

Converting a bioethanol production plant to a biobutanol production plant may involve retrofitting the existing equipment (e.g., fermentors, distillation, evaporation, etc.) as well as reconfiguring the equipment. Processes and systems are described herein that may be utilized to retrofit a bioethanol production plant. These processes and systems will be described with reference to the figures. Some processes and systems may appear in FIGS. 2-9 with the same name and numbering as used in FIG. 1 for the purpose of identifying these processes and systems as being reused or repurposed in a retrofitted bioethanol production plant. That is, equipment in a bioethanol production plant may be reused for a different purpose such as the production of a different product alcohol. For example, a distillation column that was designed, constructed, installed, and/or used for the distillation of ethanol in a bioethanol production plant may be repurposed and used for the distillation of butanol. In some instances, the equipment may be reused or repurposed with little or no modifications to the equipment.

As an example of an embodiment of the methods described herein, fermentation may be initiated by introducing feedstock directly into a fermentor. Suitable feedstocks include, but are not limited to, rye, wheat, corn, corn mash, cane, cane mash, barley, cellulosic material, lignocellulosic material, or mixtures thereof. In some embodiments, the feedstock may be dry milled or wet milled. In some embodiments, prior to the introduction to the fermentor, the feedstock may be liquefied to create feedstock slurry which may comprise undissolved solids and sugar (e.g., a fermentable carbon source). Liquefaction of feedstock may be accomplished by any known liquefying processes including, but not limited to, an acid process, an enzyme process (e.g., alpha-amylase), or an acid-enzyme process. Liquefaction may take place in a liquefaction unit.

Undissolved solids and/or oil may be separated from the feedstock slurry by a number of means including, but not limited to, decanter bowl centrifugation, three-phase centrifugation, disk stack centrifugation, filtering centrifugation, decanter centrifugation, filtration, vacuum filtration, beltfilter, pressure filtration, filtration using a screen, screen separation, grating, porous grating, flotation, hydrocyclone, filter press, screwpress, gravity settler, vortex separator, or combinations thereof. In some embodiments, the equipment for separation or removal of undissolved solids and oil may be installed between a liquefaction unit and a fermentor. In some embodiments, the equipment for separation or removal of undissolved solids and oil may be taken off-line or out of service as needed. This may be accomplished, for example, by installing valves and/or blinds in the piping that enters and/or exits the equipment. In addition, valves may be installed in the piping as a means to bypass the equipment for separation or removal of undissolved solids and oil. In some embodiments, the equipment for separation or removal of undissolved solids and oil may include additional piping for processing the undissolved solids, oil, or other byproducts.

In some embodiments, separation of the feedstock slurry produces a liquid phase and a solid phase (e.g., undissolved solids). Liquid phase may be added to the fermentor, and the solid phase (or "wet cake") may be further processed. Wet cake may include a portion of the sugar and water. As an example of processing the wet cake, wet cake may be washed with water to recover the sugar (e.g., oligosaccharides) present in the wet cake, and the recovered sugar and water may be recycled to the liquefaction unit. After washing, wet cake may be further processed, for example, to form animal feed. In some embodiments, separation of feedstock slurry may also produce an oil stream or phase. For example, if corn is the feedstock, corn oil may also be produced during the preparation of the feedstock. For a description of methods and systems for separating undissolved solids and oil from feedstock slurry see, for example, U.S. Patent Application Publication No. 2012/0164302 and PCT International Publication No. WO 2012/173660; the entire contents of each are herein incorporated by reference.

Removal of undissolved solids from the feedstock slurry has several benefits. For example, since the undissolved solids are not sent to the fermentor, microorganisms do not contact the undissolved solids. In addition, extractant and/or product alcohol such as butanol do not get trapped in the undissolved solids. Since the undissolved solids are not exposed to microorganisms, extractant, product alcohol, or other byproducts of the fermentation, processing of these solids for animal feed may be improved.

In some embodiments, removal of undissolved solids and oil prior to fermentation may allow separation and recycle of microorganisms. The ability to recycle the microorganisms may reduce or eliminate the need to grow additional microorganisms for the fermentation process and the need for additional equipment for microbial growth (e.g., propagation tanks). Removing undissolved solids and oil from the fermentation feed slurry may facilitate the removal of product alcohol through in situ product removal (ISPR) and may also allow for recycle of the microorganism.

In some embodiments, oil may not be discharged separately from the undissolved solids, and may ultimately be present in the wet cake. When the wet cake is removed via centrifugation or other separation means as described herein, a portion of oil from the feedstock (e.g., corn oil from corn feedstock) may remain with the wet cake. In some embodiments, the wet cake may be washed with, for example, additional water by centrifugation or other separation device. In some embodiments, oil may be separated from the wet cake and, for example, converted to an extractant for subsequent use in the same or different fermentation process.

In addition, oil may hydrolyze forming glycerin and fatty acids during the fermentation process. Glycerin may accumulate in water resulting in a reduction in the amount of water available for recycling throughout the production process. Thus, removal of oil from the undissolved solids may increase the efficiency of production process by increasing the amount of water that can be recycled throughout the production process.

In some embodiments, if corn is the feedstock, corn oil may also be produced during the preparation of the feedstock. Corn oil, which contains triglycerides, free fatty acids, diglycerides, monoglycerides, and phospholipids, may be added to other co-products or byproducts of the fermentation process (e.g., animal feed) and creating the ability to vary the amounts of these components in the resulting co-product. The ability to vary and customize the content of an animal feed co-product would be advantageous. For example, the fat content of the resulting co-product may be controlled to yield a low fat, high protein animal feed that would better suit the needs of dairy cows compared to a high fat product. It may be desired to operate the undissolved solids, oil, and fermentable sugar separation equipment during production of a product alcohol. Utilizing a series of valves and blinds, bypassing the separation equipment may be accomplished to return to the standard ethanol process operation.

In some embodiments, feedstock and/or liquid phase may be added to a fermentor at a pre-determined level. For example, feedstock and/or liquid phase may be added until it reaches the agitator blade of the fermentor. The agitator may then be activated, for example, following the addition of the microorganism. In some embodiments, the agitator may be activated following the addition of the contents of a propagation tank. In some embodiments, feedstock and/or liquid phase may be fed to the fermentor until a steady state is reached. In some embodiments, feedstock and/or liquid phase may be circulated through an external cooling loop in order to maintain a temperature below, for example, 35° C. or any other control point.

In some embodiments, simultaneous saccharification and fermentation may occur in a fermentor. Any known saccharification process utilized by the industry may be used including, but not limited to, an acid process, an enzyme process, or an acid-enzyme process. In some embodiments, an enzyme such as glucoamylase, may be introduced to fermentor in order to hydrolyze sugars (e.g., oligosaccharides) present in feedstock or liquid phase to monosaccharides. In some embodiments, saccharification may occur in a separate saccharification unit. In some embodiments, saccharification may occur prior to separation of the feedstock slurry or after separation of the feedstock slurry. For a description of methods and systems for processing biomass for fermentation see, for example, PCT International Publication No. WO 2011/160030; the entire contents of which are herein incorporated by reference.

FIGS. 2A to 2D illustrate embodiments of a retrofit bioethanol production plant to produce a product alcohol, for example, butanol. Some processes and systems may appear in these figures with the same name and numbering as used in FIG. 1 for the purpose of identifying these processes and systems as being reused in a retrofitted bioethanol production plant. Butanol may be produced by fermentation of sugars, and these fermentable sugars may be derived from any biomass source including corn, cane, cellulosic, or lignocellulosic material. This biomass may be processed, for example, by liquefaction and/or saccharification to form a mash that is fermented by a microorganism such as yeast. In some embodiments, the biomass may be subjected to simultaneous saccharification and fermentation (SSF). FIGS. 2A to 2D illustrate various embodiments of a retrofitted bioethanol production plant that features the removal of butanol from fermentation broth using liquid-liquid extraction. The processes described in FIGS. 2A to 2D may be used to produce other product alcohols.

Figure 2A:
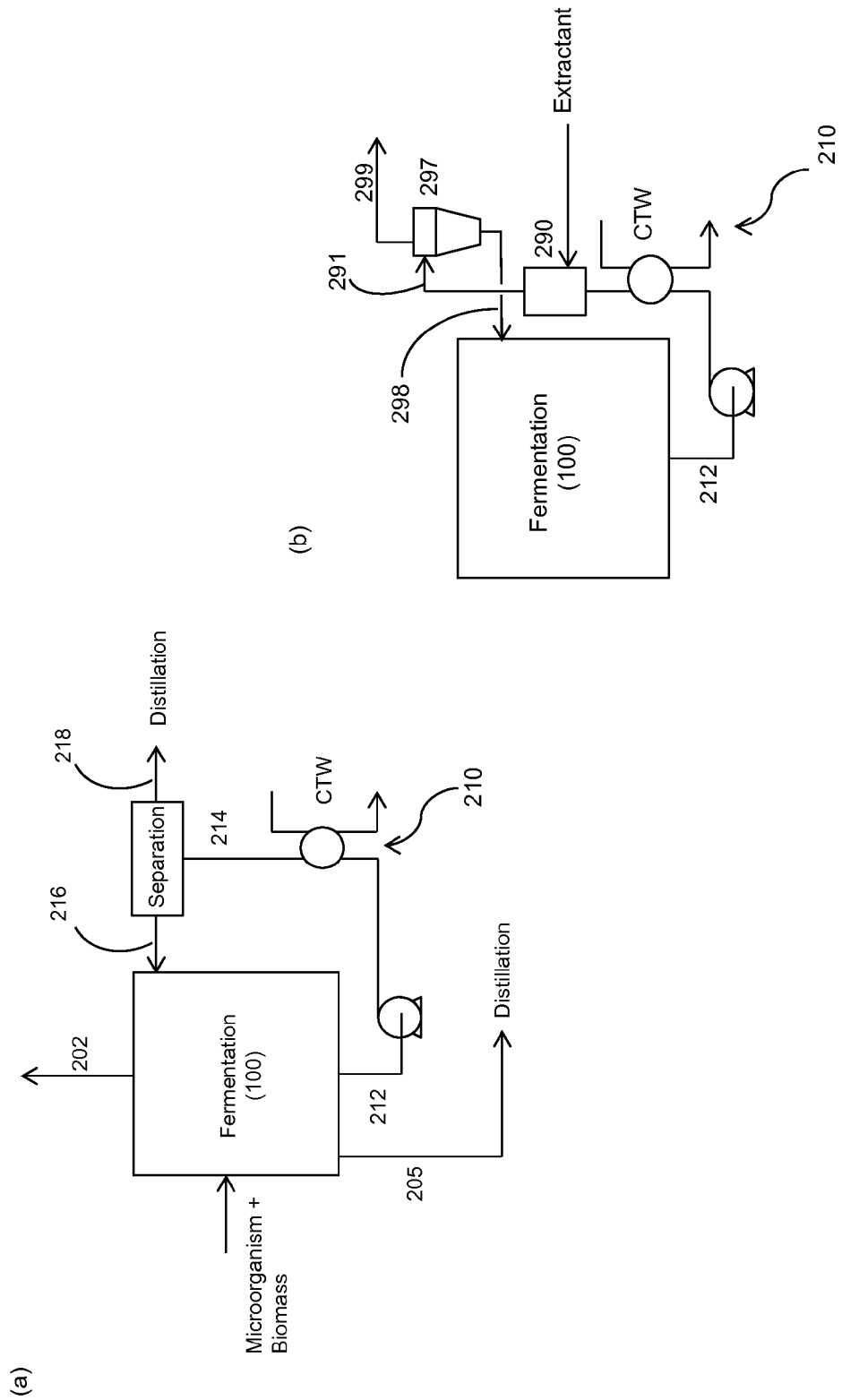
FIGS. 2A to 2D illustrate various embodiments of a retrofit bioethanol production plant.

FIGS. 2A(a) and 2A(b) illustrate an embodiment of a retrofit bioethanol production plant. As described herein, extraction of a product alcohol such as butanol may occur external or downstream of the fermentor. FIG. 2A(b) illustrates a modification to an existing external cooling loop of a fermentor in a bioethanol production plant. This modification allows for the continuous external extraction of butanol. The external cooling loop cools fermentation broth from the fermentor by removing fermentation broth from the fermentor, passing the fermentation broth to a heat transfer device (e.g., heat exchanger), and returning the cooled fermentation broth to the fermentor. For a retrofitted bioethanol production plant, the external cooling loop may be adapted to remove butanol from the fermentation broth by continuous external extraction as well as cooling the fermentation broth.

Referring to FIG. 2A(a), the temperature of fermentation broth may increase during fermentation and the fermentation broth may be cooled by cycling through external cooling loop 210. For example, fermentation broth 212 may exit fermentation 100 via an exit line and pass through a heat exchanger ("CTW" refers to cooling tower water) where fermentation broth 212 is cooled to a lower temperature. Cooled fermentation broth 214 may be conducted to a separation unit and may be separated forming a butanol-rich stream 218 and a butanol-lean stream 216. Butanol-rich stream 218 may be further processed for recovery of butanol, for example, butanol-rich stream 218 may be conducted to distillation for recovery of butanol. Butanol-lean stream 216 may be returned to fermentation 100 via a return line for continued production of a product alcohol such as butanol. When fermentation is complete, the fermentor contents may be discharged as aqueous stream 205 (or beer stream 205) and may be further processed for recovery of butanol. For example, aqueous stream 205 may be conducted to a beer column for recovery of any remaining butanol. Non-condensable gases 202 (e.g., carbon dioxide) produced during fermentation may be vented, for example, to a scrubber system.

Referring to FIG. 2A(b), fermentation 100 may be modified for continuous external extraction of a product alcohol such as butanol. External cooling loop 210 may be modified to include a mixing device 290 and separation system 297. Fermentation broth 212 exiting the heat exchanger may be conducted to mixing device 290. Extractant may be added to mixing device 290 and combined with fermentation broth 212 to produce biphasic mixture 291 (or two-phase mixture). Biphasic mixture 291 may be introduced to separation system 297, in which separation of biphasic mixture 291 produces butanol-containing organic phase 299 and aqueous phase 298. Organic phase 299 may be discharged from separation system 297 for further processing as described herein, and aqueous phase 298 or a portion thereof may be returned to fermentation 100 via a return line. In another embodiment, aqueous phase 298 may be cooled by the heat exchanger prior to return to fermentation 100. In some embodiments, a portion of aqueous phase 298 may be sent to a beer column. Butanol-containing organic phase 299 may be discharged from separation system 297 and, for example, may be conducted to an extractant column.

Circulation of fermentation broth may include a pathway through a heat transfer device (e.g., heat exchanger) and mass transfer device (e.g., separation system 297) enabling the removal of heat and butanol per pass through a modified external cooling loop. Moreover, in some embodiments, the rate of heat and butanol removal may be balanced with the rate of heat and butanol production during fermentation by adjusting the circulation flow through the external cooling loop, cooling fluid flow through the heat exchanger, and flow of extraction.

Mixing device 290 may be any device capable of mixing liquid substances. In some embodiments, mixing device 290 may comprise an inline mixer such as an inline static mixer. In some embodiments, mixing device 290 may comprise a piping tee such as a piping T-connector or an agitated vessel. Separation system 297 may be any device capable of liquid-liquid separation. In some embodiments, separation system 297 may comprise one or more of the following: hydrocyclone, centrifuge, inline vortex separator, decanter (e.g., extractant decanter), or filter. As an example of separation system 297, separation system 297 may comprise one or more individual hydrocyclones and each individual hydrocyclone may be a vessel that includes one or more hydrocyclone liners packaged together inside the vessel, whereby each vessel can treat a large flow while maintaining phase separation ability. A biphasic mixture may enter the hydrocyclone liners via, for example, a tangential inlet nozzle. In some embodiments, the largest diameter of the hydrocyclone liner may be at the inlet nozzle and the hydrocyclone liners may be tapered. Separation by hydrocyclones may be advantageous compared to other separation mechanisms because hydrocyclones have a relatively compact size and are less expensive.

As another example of separation system 297, separation system 297 may comprise one or more inline vortex separators or in some embodiments, separation system 297 may comprise a single, large capacity inline vortex separator. In some embodiments, separation system 297 may comprise one or more centrifuges.

In some embodiments, mixing device 290 and separation system 297 may each be fluidly connected to the return line and to each other. In some embodiments, mixing device 290 and separation system 297 may be fluidly interposed between the heat exchanger and the return line. For example, mixing device 290 may be fluidly interposed between the heat exchanger and separation system 297; and separation system 297 may be fluidly interposed between mixing device 290 and the return line. In another embodiment, mixing device 290 and separation system 297 may each be fluidly connected to the exit line from fermentation 100.

Figure 2B:
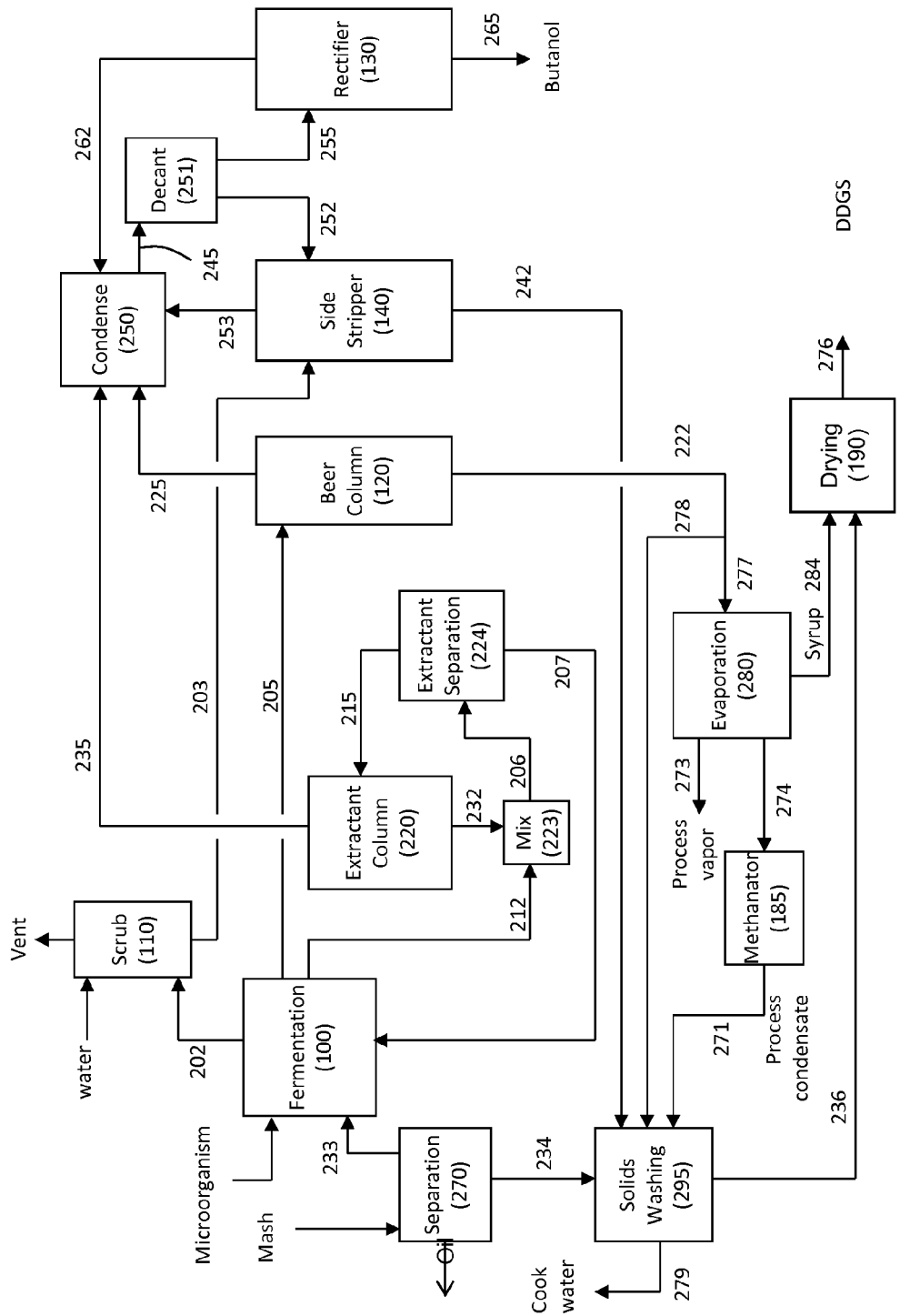

FIG. 2B illustrates an embodiment of a retrofitted bioethanol production plant that features the removal of product alcohol (e.g., butanol) from fermentation broth by extraction. Referring to FIG. 2B, liquefied mash may enter separation 270 to form wet cake 234 comprising undissolved solids and a clarified solution of dissolved fermentable sugars 233 (or thin mash 233). In some embodiments, liquefied mash may enter separation 270 to form wet cake 234, an aqueous solution of dissolved fermentable sugars 233, and an oil stream. The terms thin mash and aqueous solution may also be referred to as aqueous feedstream. Thin mash 233 and microorganisms may be added to fermentation 100. In some embodiments, the process may include one or more fermentors; and in another embodiment, this plurality of fermentors may be operated in parallel. The mash is fermented by the microorganisms to produce butanol. Gases 202 generated during the fermentation may be vented through scrub system 110.

Scrub stream 203 may be conducted to side stripper column 140 to recover butanol and other volatile components into vapor overhead stream 253 and to form liquid bottoms stream 242 that may sometimes be referred to as lutter water. This recovery of butanol may also be referred to as dealcoholization, and the side stripper column may be referred to as a dealcoholization column. In some embodiments, side stripper column 140 may be a retrofit of the side stripper column used in ethanol production and a vapor inlet may be provided at the bottom of side stripper column 140 as a heating means. In some embodiments, the vapor inlet to side stripper column 140 may be sourced in part from a vapor liquid flash device such as a unit used in lowering the pressure of hydrothermally cooked mash. In some embodiments, the vapor inlet to side stripper column 140 may be sourced in part from the partial reboil of side stripper bottoms 242.

A fermentation that produces butanol using the same mash composition as a fermentation that produces ethanol may require the removal of butanol, for example, to minimize the toxicity effects of butanol on the microorganism. In some embodiments, throughout the fermentation, at least one flow circulation is maintained outside each fermentor to affect both heat transfer (cooling of fermentation broth) and mass transfer (removing butanol from fermentation broth). Butanol may be removed from an externally circulated fermentation broth using various methods known in the art such as low temperature flashing, liquid-liquid extraction, and gas stripping among others.

In this example, butanol may be removed from fermentation broth utilizing extractive fermentation. Fermentation broth 212 comprising butanol may be contacted with extractant 232 by mixing 223 to form stream 206. "Contacted" or "contacting" means the fermentation broth and extractant are brought into physical contact at any time during the fermentation process. As illustrated in FIG. 2B, fermentation broth 212 may be removed from fermentation 100 prior to the step of contacting with the extractant. That is, extraction of butanol occurs downstream (i.e., external) of fermentation 100. In some embodiments, the fermentation broth comprising butanol may be removed continuously from fermentation 100 or may be removed in batches from fermentation 100. Extraction of butanol from the fermentation broth may be performed with or without the removal of the microorganism from the fermentation broth. The microorganism may be removed from the fermentation broth by any means known in the art including, but not limited to, filtration or centrifugation; and may be returned to fermentation 100. In some embodiments, stream 206 may be a heterogeneous mixture comprising more than one liquid phase (e.g., a biphasic mixture).

In some embodiments, an extractant may be water-immiscible. In some embodiments, the extractant may be one or more organic solvents. In some embodiments, the extractant may be nontoxic to the microorganism. In some embodiments, the extractant may have a high partition coefficient for a product alcohol (e.g., butanol). In some embodiments, the extractant may be one or more of the following: fatty alcohols, fatty acids, fatty esters, fatty aldehydes, fatty amides, triglycerides, monoalkyl phosphates, dialkyl phosphates, trialkyl phosphates or mixtures thereof. Methods for producing and recovering butanol from a fermentation broth using extractive fermentation are described in U.S. Patent Application Publication No. 2009/0305370; U.S. Patent Application Publication No. 2010/0221802; U.S. Patent Application Publication No. 2011/0097773; U.S. Patent Application Publication No. 2011/0312044; and U.S. Patent Application Publication No. 2011/0312043; the entire contents of each are herein incorporated by reference. In some embodiments, the extractant may be one or more ionic liquids (see, e.g., U.S. Patent Application Publication No. 2010/0143992; U.S. Patent Application Publication No. 2010/0143993; U.S. Patent Application Publication No. 2010/0143994; and U.S. Patent Application Publication No. 2010/0143995; the entire contents of each are herein incorporated by reference).

Mixing device 223 may be any device capable of mixing liquid substances. In some embodiments, mixing device 223 may comprise an inline mixer such as an inline static mixer. In some embodiments, mixing device 223 may comprise a piping tee such as a piping T-connector or an agitated vessel. Extractant separation 224 may be any device capable of liquid-liquid separation. In some embodiments, extractant separation 224 may comprise one or more of the following: a hydrocyclone, a centrifuge, an inline vortex separator, a decanter (e.g., an extractant decanter), or a filter. As an example, extractant separation 224 may comprise one or more individual hydrocyclones and each individual hydrocyclone may be a unit that includes one or more hydrocyclone liners packaged together inside the unit, whereby each unit can treat a large flow while maintaining phase separation ability. A biphasic mixture may enter the hydrocyclone liners via, for example, a tangential inlet nozzle. In some embodiments, the largest diameter of the hydrocyclone liner may be at the inlet nozzle and the hydrocyclone liners may be tapered. Separation by hydrocyclones may be advantageous compared to other separation mechanisms because hydrocyclones have a relatively compact size and are less expensive.

As another example, extractant separation 224 may comprise one or more inline vortex separators or in another embodiment, extractant separation 224 may comprise a single, large capacity inline vortex separator. In some embodiments, extractant separation 224 may comprise one or more centrifuges.

Referring to FIG. 2B, stream 206 may be introduced to an extractant separation system 224 forming aqueous phase 207 and organic phase 215 (e.g., a butanol-containing phase). Butanol-containing organic phase 215 may be separated from the aqueous phase 207 using methods known in the art, including but not limited to, siphoning, decantation, centrifugation, mixer-settler, gravity settler, membrane-assisted phase splitting, and the like. Aqueous phase 207 may be at least partially depleted of butanol relative to stream 212 (e.g., butanol-lean) and may be recycled to fermentation 100.

Extraction of butanol from the fermentation broth may be performed with or without the removal of the microorganism from the fermentation broth. The microorganism may be removed from the fermentation broth by any means known in the art including, but not limited to, filtration or centrifugation; and may be returned to fermentation 100. Extraction of butanol from the fermentation broth may be performed with or without the removal of undissolved solids from the fermentation broth. Undissolved solids may be removed from the fermentation broth by any means known in the art including, but not limited to, filtration or centrifugation; and may be returned to fermentation 100. In some embodiments, an automatic self-cleaning water filter may be used to trap solids from stream 212.

Figure 2C:
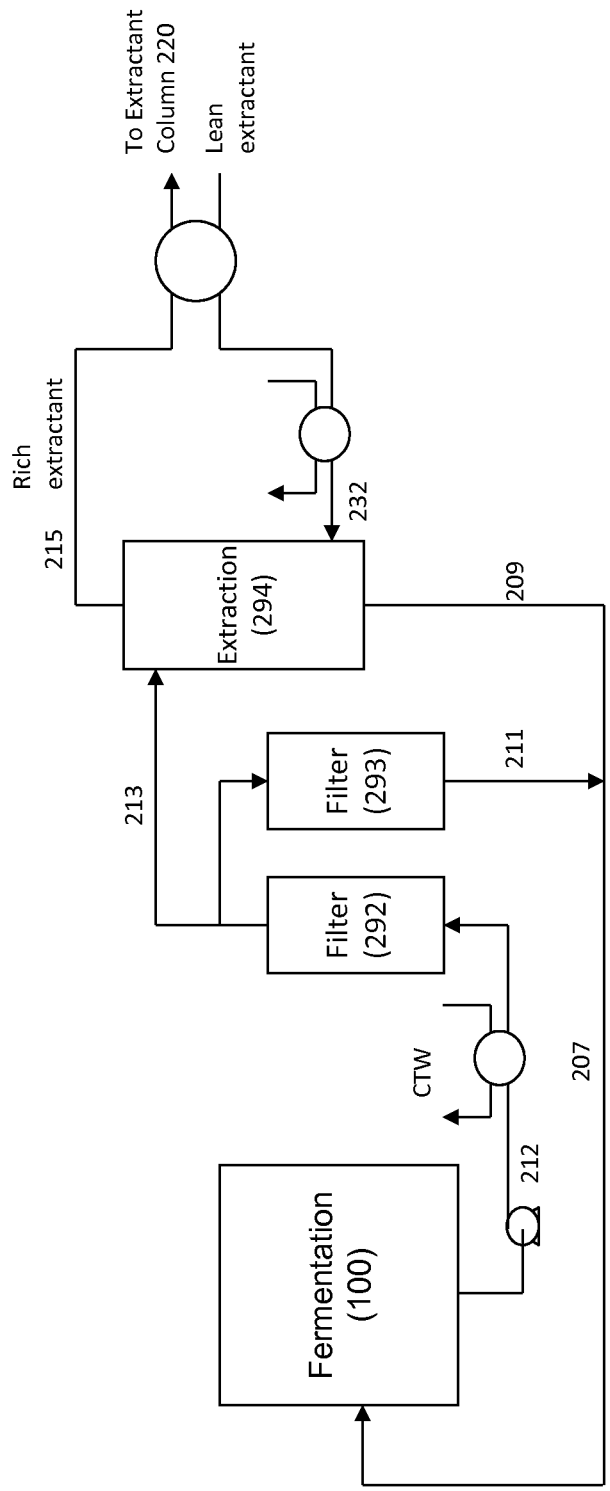

FIG. 2C illustrates some embodiments of the use of an automatic self-cleaning filtration. Fermentation broth 212 may be removed from fermentation 100 and may be cooled using an existing fermentor cooler before entering automatic self-cleaning filter 292. Some particulates may be retained on the screen medium of the filter as clarified mash passes through. A second filter, filter 293, may be simultaneously undergoing backflush where a portion of the clarified mash flows back through the screen carrying the particulates with it to discharge concentrated solids stream 211. Another portion 213 of the clarified mash may enter the top of extraction 294 while extractant stream 232 is fed in the bottom of the column. The liquids may be brought into contact either passively by density differences or with the aid of mechanical motion (e.g., a Karr® column) by any means known in the art. Butanol-containing organic phase 215 emerges from the top of extraction 294 and aqueous phase 209 containing fermentation broth that has been at least partially depleted of butanol relative to stream 213 emerges from the bottom of extraction 294. Streams 209 and 211 may be combined to form stream 207 that is returned to fermentation 100. Extractant stream 215 that is rich in butanol may be heated in a heat exchanger that transfers heat from an extractant stream that is lean in butanol and that originates from the bottoms of extractant column 220. After releasing some heat, the lean extractant may be further cooled with water in a heat exchanger to reach a temperature that is suitable for fermentation. Circulation of fermentation broth may include a pathway through a heat transfer device and mass transfer device enabling the removal of heat and butanol per pass through a modified external cooling loop. Moreover, in some embodiments, the rate of heat and butanol removal may be balanced with the rate of heat and butanol production during fermentation by adjusting at least the circulation flow through the external cooling loop, adjusting the flow of cooling fluid in a heat exchanger, adjusting the flow of extractant, or combinations thereof.

Referring to FIG. 2B, when fermentation is complete, the fermentor contents may be discharged as aqueous stream 205 (or beer stream 205) and may be conducted to beer column 120 for recovery of any remaining butanol. Beer stream 205 may be introduced to beer column 120 to produce vapor overhead stream 225 comprising butanol, water, and optionally non-condensable gases and butanol-lean bottoms stream 222 (or beer bottoms stream 222). In some embodiments, the vapor overhead stream from the beer column may be referred to as a butanol-rich vapor stream. Prior to entering beer column 120, beer stream 205 may be degassed to remove at least a portion of non-condensable gases (e.g., carbon dioxide), and the non-condensable gases may be sent to a scrubber or a thermal oxidizer. In some embodiments, at least a portion of beer stream 205 may be recycled to fermentation 100.

Beer column 120 may be any conventional distillation column having, for example, a feed inlet, an overhead vapor outlet, a bottoms stream outlet, a heating means (e.g., heated vapor), and a sufficient number of stages to effect the separation of butanol from beer bottoms stream 222. For example, in some embodiments, beer column 120 may include a reboiler. In some embodiments, beer column 120 may be maintained at a pressure below atmospheric pressure. In some embodiments, a pressure drop across beer column 120 may be maintained from about 1.0 psi to about 5.0 psi, from about 1.0 psi to about 4.5 psi, from about 1.5 psi to about 4.0 psi, from about 1.5 psi to about 3.5 psi, from about 1.5 psi to about 3.0 psi, or from about 2.0 psi to about 2.5 psi. In some embodiments, pressure in beer column 120 at a vapor inlet may be below atmospheric pressure. In some embodiments, the vapor inlet may be at the bottom of beer column 120 and the overhead vapor outlet may be at the top of beer column 120.

In some embodiments, beer column 120 may be a retrofit of the beer column used in ethanol production. In some embodiments, the vapor inlet to beer column 120 may be sourced in part from a vapor liquid flash device such as a unit used in lowering the pressure of hydrothermally cooked mash. In some embodiments, the vapor inlet to beer column 120 may be sourced in part from the reboil of beer column bottoms 222 or the partial vaporization of process water (e.g., lutter water). In some embodiments, the vapor inlet to beer column 120 may be sourced in part from an evaporation train such as the evaporation train used in concentrating thin stillage. In some embodiments, the vapor inlet to beer column 120 may be from the same source when operating in either ethanol or butanol production.

Butanol-containing organic phase 215 may comprise butanol, water, extractant, non-condensable gases as well as byproducts of the fermentation process that have sufficient solubility to partition into the extractant. In some embodiments, butanol-containing organic phase 215 may have a butanol concentration, for example, from about 0.1 wt % to about 50 wt %, about 0.5 wt % to about 40 wt %, from about 1 wt % to about 35 wt %, from about 2 wt % to about 30 wt %, from about 3 wt % to about 25 wt %, from about 5 wt % to about 20 wt % based on the weight of butanol-containing organic phase 215.

Butanol may be recovered from butanol-containing organic phase 215 using methods known in the art including, but not limited to, distillation, adsorption (e.g., by resins), separation by molecular sieves, pervaporation, and the like. As exemplified in FIG. 2B, a combination of distillation and decantation may be utilized to recover butanol from butanol-containing organic phase 215. In some embodiments, distillation may be accomplished using at least two distillation columns: for example, extractant column 220 and retrofitted rectifier column 130.

Extractant column 220 may be any conventional distillation column having, for example, a feed inlet, an overhead vapor outlet, a bottoms stream outlet, a heating means, and a sufficient number of stages to effect the separation of butanol from extractant. In some embodiments, extractant column 220 may have at least five stages and may include a reboiler. In some embodiments, extractant column 220 may have ten or fifteen stages. Extractant column 220 may include a rectification section to minimize loss of extractant. Heat for extractant column 220 may be provided by a heated vapor such as steam that may be supplied to extractant column 220 via a vapor inlet. The heated vapor may have a pressure corresponding to the column pressure at the vapor inlet. In some embodiments, a vapor inlet may be at the bottom of extractant column 220 and an overhead vapor outlet may be at the top of extractant column 220. In some embodiments, extractant column 220 may be maintained at a pressure below atmospheric pressure. This may be achieved, for example, by operation of a condenser (or condensation unit) for condensing overhead vapor from extractant column 220 at below atmospheric pressure. In some embodiments, extractant column 220 may be a new installation in a retrofitted bioethanol production plant.

In some embodiments, extractant column 220 may be a duplicate installation of beer column 120. In some embodiments, the vapor inlet to extractant column 220 may be sourced in part from a vapor liquid flash device such as a unit used in lowering the pressure of hydrothermally cooked mash. In some embodiments, the vapor inlet to extractant column 220 may be sourced in part from the reboil of extractant column bottoms 232 or the partial vaporization of process water (e.g., lutter water). In some embodiments, the vapor inlet to extractant column 220 may be sourced in part from an evaporation train such as the evaporation train used in concentrating thin stillage.

Extraction in combination with decantation effects a separation of butanol and non-condensable gases from extractant and water. For example, butanol-containing organic phase 215 may be distilled via extractant column 220 to provide butanol-rich vapor overhead stream 235 comprising butanol, water, and non-condensable gases (e.g., extractant-lean) and an extractant-rich bottoms stream 232 comprising extractant and water. The extractant-rich bottoms stream 232 may be substantially free of butanol. In some embodiments, the term "substantially free of butanol" means butanol comprises about 0 wt % to about 0.5 wt % of the bottoms stream 232. The extractant-rich bottoms stream 232 may be recycled to the extractive fermentation process. For example, extractant-rich bottoms stream 232 may be used as extractant that is contacted by mixing 223 with fermentation broth 212 to form stream 206.

Vapor overhead stream 235 may comprise about 20 wt % butanol and about 80 wt % water. In some embodiments, vapor overhead stream 235 may comprise about 25 wt % butanol and about 75 wt % water, about 30 wt % butanol and about 70 wt % water, or about 35 wt % butanol and about 65 wt % water. In some embodiments, vapor overhead stream 235 may comprise about 20 wt % to about 50 wt % butanol and about 50 wt % to about 80 wt % water. In some embodiments, the amount of extractant in vapor overhead stream 235 is about 0 wt % to about 1 wt %. In some embodiments, the amount of extractant in vapor overhead stream 235 is about 0 wt % to about 2 wt %.

Vapor overhead stream 225 from beer column 120, stream 235 from extractant column 220, and stream 253 from side stripper column 140 may be conducted to condense 250 (or condenser or condensation unit) to form liquid stream 245. In some embodiments, the condensed liquid stream may be referred to as a butanol-rich liquid stream. Liquid stream 245 may be separated in decant 251 (or decanter or decantation unit) into aqueous phase 252 and organic phase 255. If a non-condensable gas is present in streams 225 or 235, at least a portion of the non-condensable gas may be purged from condense 250 and/or decant 251 and sent to a thermal oxidizer or scrubber. Organic phase 255 may be conducted to rectifier column 130 that has been repurposed to dehydrate butanol and form a bottoms stream 265 which is substantially butanol (e.g., about 98 wt % to about 100 wt %) and vapor overhead stream 262. Bottoms stream 265 may be substantially free of water (e.g., about 0 wt % to about 1 wt % water may be present). Vapor overhead stream 262 may be recycled to condense 250. In some embodiments, the composition of vapor overhead stream 235 may be controlled by introducing a portion of aqueous phase 252 and/or a portion of organic phase 255 as reflux to extractant column 220 at any favorable feed location. For example, aqueous reflux may be introduced at the top of extractant column 220 while organic reflux may be introduced along with feed stream 215 at some location below the top of the column. In some embodiments, organic reflux may be combined with feed stream 215 before entering extractant column 220. The amount of extractant in vapor overhead stream 235 may be minimized by the controlled use of reflux streams.

Rectifier 130 may be any conventional distillation column having, for example, a feed inlet, an overhead vapor outlet, a bottoms stream outlet, a heating means (e.g., heated vapor), and a sufficient number of stages to effect the separation of butanol and water. For example, in some embodiments, rectifier 130 may include a reboiler. In some embodiments, rectifier 130 may be maintained at a pressure below atmospheric pressure.

In some embodiments, rectifier column 130 may be a rectifier column from a retrofitted bioethanol production plant that has been repurposed as a dehydration column. In some embodiments, an existing rectifier column may be retrofitted to operate at an elevated pressure that is below the maximum allowable working pressure of rectifier column 130. In some embodiments, rectifier column 130 may be a new dehydration column, for example, of minimal size. In some embodiments, an existing rectifier column in a retrofitted bioethanol production plant may be taken off-line during butanol production, for example, via valving and lockout procedures or line breaking procedures; and may be returned on-line for bioethanol production in a reversible-retrofitted bioethanol production plant.

In some embodiments, beer bottoms stream 222 may be thin stillage, with undissolved solids or a portion of undissolved solids having been removed prior to distillation and the microorganism optionally removed after fermentation. If undissolved solids have been removed, then solids separation may not be required for beer bottoms stream 222, and beer bottoms stream 222 may bypass any existing solids separation equipment with a series of valves, pipe blinds, and pipe segments. This allows for quick reversibility, depending on the equipment configuration desired for production of different product alcohols.

In some embodiments where separation 270 is not used to remove undissolved solids from liquefied mash, separation 270 may be used to remove undissolved solids from beer bottoms stream 222. In some embodiments, separation may be accomplished using a mechanical separator such as a centrifuge or filter press. In some embodiments, separation 270 may include one or more centrifuge units. For example, two, three, four, five, or six centrifuge units may be utilized to separate beer bottoms stream 222. In some embodiments, the centrifuge units may be the existing centrifuge units in an ethanol production plant. In some embodiments, beer bottoms stream 222 may be further processed to produce DDGS. For a description of methods and systems for byproduct and co-product processing see, for example, U.S. Patent Application Publication No. 2012/0164302 and PCT International Publication No. 2012/173660; the entire contents of each are herein incorporated by reference.

A portion 277 of thin stillage 222 may be concentrated by evaporation 280 (e.g., four (4) effect by two (2) body train) to form syrup 284. In some embodiments, evaporation 280 may be a multi-effect evaporation system that is reconfigured (e.g., installing one new body to form a three (3) effect by three (3) body train) as described in U.S. Patent Application Publication No. 2011/0315541; the entire contents of which are herein incorporated by reference. The evaporators incrementally evaporate water from thin stream 277 and a portion of the water evaporated may be removed as process vapor 273. In some embodiments, multiple process vapor streams may be removed from multi-effect evaporation 280 and each vapor stream may be sourced at a different pressure from a different evaporation effect. These process vapor streams may be used to provide boilup to multiple stripping columns such as beer column 120 and extractant column 220. In some embodiments, beer column 120 and extractant column 220 may be operated at different pressures. Another portion of water evaporated in evaporation 280 may be removed as process condensate 274 and may be further processed in methanator 185 to reduce the level of organics in process condensate 271. In some embodiments, evaporation 280 evaporates water from thin stillage portion 277 such that the weight concentration of water in syrup 284 is from about 40% to about 80%, from about 50% to about 70%, or from about 55% to about 65%. In some embodiments, the weight concentration of water in thin stillage portion 277 is about 90%. In some embodiments, a portion 278 of thin stillage 222 may be recycled as backset with process condensate 271 and lutter water 242 to recover dissolved fermentables from wet cake 234 in solids washing 295. Washed cake 236 is formed and the total wash liquids generated in solids washing 295 may be removed as cook water 279 that may be recycled for mashing biomass such as corn. In some embodiments, syrup 284 may be combined with washed cake 236 in dryer system 190 to produce DDGS.

For a multi-effect evaporation 280, clean plant steam and/or reused plant steam may be utilized as a heat source to effect evaporation of water from thin stillage to produce mid stillage. The resulting steam constituted by the evaporated water from the thin stillage may be then be used in evaporators of subsequent effects to incrementally evaporate water from mid stillage to produce syrup 284. Steam constituted by the evaporated water from the mid stillage may be collected and discharged via steam line 273 and integrated into the fermentation system as a heating means for beer column 120 and/or extractant column 220 or as the heating means of other unit operations, such as rectifier column 130. Steam condensate from evaporation 280 may be discharged through condensate line 274 and may be treated in methanator 185 to reduce the level of dissolved organics in process condensate 271. Process condensate 271 may be used in conjunction with other process water sources to recover starch from wet cake 234 in solids washing 295. Examples of evaporation systems and additional methods for recovering alcohols are described, for example, in U.S. Patent Application Publication No. 2011/084784; the entire contents of which are herein incorporated by reference.

In one embodiment of the invention, one or more of the following: beer column, rectifier, centrifuge, mixer, and dryer may be utilized in a retrofitted bioethanol production plant. That is, this equipment which may be currently used in a bioethanol production plant may also be used in a retrofitted bioethanol production plant to produce biobutanol.

Figure 2D:
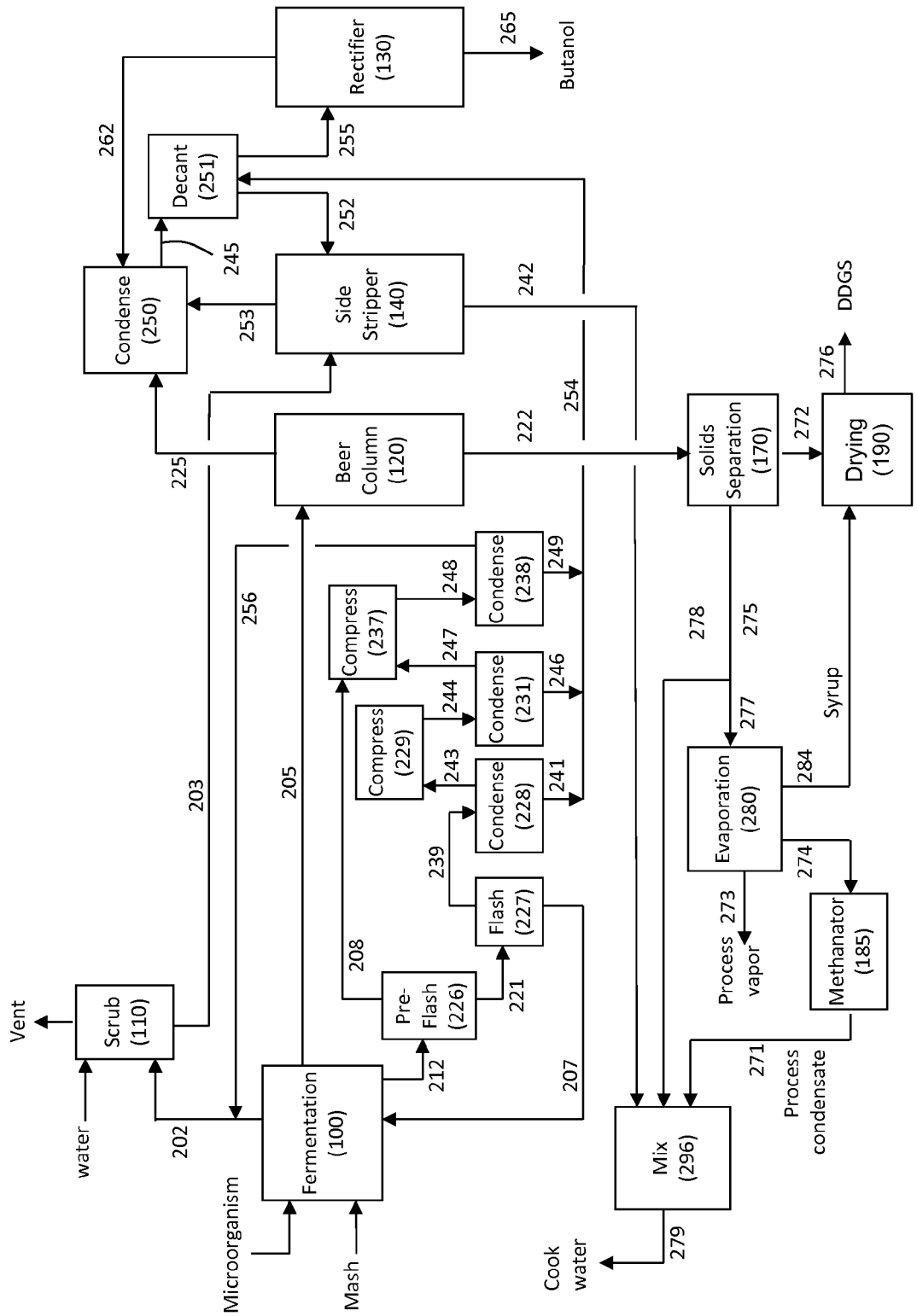

FIG. 2D illustrates an embodiment of a retrofitted bioethanol production plant that features the removal of product alcohol (e.g., butanol) from fermentation broth by vaporization under vacuum. Liquefied mash and microorganisms may be added to fermentation 100. The mash may be fermented by the microorganisms in a fermentation broth to produce butanol. Methods for producing and recovering product alcohols from a fermentation broth using vaporization under vacuum are described in U.S. Patent Application Publication No. 2012/0035398; U.S. Patent Application Publication No. 2012/0211348; and International Patent Application No. PCT/US2012/068288; the entire contents of each are herein incorporated by reference.

Referring to FIG. 2D, butanol may be removed from a single flow circulation of fermentation broth utilizing vaporization under vacuum to effect both heat transfer (cooling of fermentation broth) and mass transfer (removing butanol from fermentation broth) simultaneously. Fermentation broth 212 comprising butanol may be conducted to pre-flash 226 operating at a reduced pressure to degas much of the carbon dioxide dissolved in fermentation broth 212 and form vapor stream 208. The degassed fermentation broth 221 may then be conducted to flash 227 (or flash unit) operating at a further reduced pressure to volatilize a portion of the dissolved butanol forming vapor stream 239. Stream 207 that has been evaporatively cooled and at least partially depleted of butanol relative to fermentation broth 212 may be recycled back to fermentation 100. Vapor stream 239 comprising butanol and water may be cooled in condense 228 (or condenser or condensation unit) to form liquid stream 241 and residual vapor stream 243. The pressure of vapor stream 243 may be increased in compress 229 (or compressor unit) to form vapor stream 244. Vapor stream 244 comprising butanol and water may be cooled in condense 231 (or condenser or condensation unit) to form liquid stream 246 and residual vapor stream 247. Vapor streams 208 and 247 may be combined and conducted to compress 237 (or compressor unit) to form compressed vapor stream 248. Vapor stream 248 may then be cooled in condense 238 (or condenser or condensation unit) to form liquid stream 249 and residual vapor stream 256. Vapor stream 256 may be combined with the gases exiting fermentation 100 to form vapor stream 202 that may be vented through scrub system 110.

When fermentation is complete, the fermentor contents may be discharged as aqueous stream 205 (or beer stream 205) and may be conducted to beer column 120 for recovery of any remaining butanol. Beer stream 205 may be introduced to beer column 120 to produce a vapor overhead stream 225 comprising butanol, water, and optionally non-condensable gases and a butanol-lean bottoms stream 222 (or beer bottoms stream 222). Prior to entering beer column 120, beer stream 205 may be degassed to remove at least a portion of non-condensable gases (e.g., carbon dioxide), and the non-condensable gases may be sent to a scrubber or a thermal oxidizer. In some embodiments, at least a portion of beer stream 205 may be recycled to fermentation 100.

Beer column 120 may be any conventional distillation column having, for example, a feed inlet, an overhead vapor outlet, a bottoms stream outlet, a heating means (e.g., heated vapor), and a sufficient number of stages to effect the separation of the butanol from the beer bottoms stream 222. For example, in some embodiments, beer column 120 may include a reboiler. In some embodiments, beer column 120 may be maintained at a pressure below atmospheric pressure. In some embodiments, a pressure in beer column 120 at a vapor inlet may be below atmospheric pressure. In some embodiments, the vapor inlet may be at the bottom of beer column 120 and the overhead vapor outlet may be at the top of beer column 120. In some embodiments, beer column 120 may be a retrofit of the beer column used in ethanol production. In some embodiments, the vapor inlet to beer column 120 may be sourced in part from a vapor liquid flash device such as a unit used in lowering the pressure of hydrothermally cooked mash. In some embodiments, the vapor inlet to beer column 120 may be sourced in part from the reboil of beer column bottoms 222 or the partial vaporization of process water (e.g., lutter water). In some embodiments, the vapor inlet to beer column 120 may be sourced in part from an evaporation train such as the evaporation train used in concentrating thin stillage. In some embodiments, the vapor inlet to beer column 120 may be from the same source when operating in either ethanol or butanol production.

Liquid streams 241, 246, and 249 may be combined to form liquid stream 254. Liquid stream 254 may be separated in decant 251 into aqueous phase 252 and organic phase 255. Aqueous phase 252 and scrubber bottoms stream 203 may be conducted to retrofitted side stripper column 140 to recover butanol and other volatile compounds forming vapor overhead stream 253 and liquid bottoms stream 242 that may sometimes be referred to as lutter water. Organic phase 255 may be conducted to retrofitted rectifier column 130 to dehydrate butanol and to form bottoms stream 265 and vapor overhead stream 262. Overhead vapor streams 225, 253, and 262 may be cooled in condense 250 (or condenser or condensation unit) to form liquid stream 245 and liquid stream 245 may be conducted to decant 251 for phase separation.

Bottoms stream 222 of beer column 120 may be processed in retrofitted solids separation 170. Separation of bottoms stream 222 produces liquid stream 275 known as thin stillage and solids 272 (e.g., wet cake). A portion 277 of thin stillage 275 may be conducted to retrofitted evaporation 280 (e.g., two (2) effect by four (4) body system) for water removal and a portion 278 may be recycled as backset for mashing biomass (e.g., corn). The evaporators may be reconfigured (e.g., four (4) effect by two (2) body system) as described in U.S. Patent Application Publication No. 2011/0315541; the entire contents of which are herein incorporated by reference. The evaporators incrementally evaporate water from stream 277 to produce syrup 284 which with wet cake 272, may be further processed in drying system 190 to yield DDGS 276. A portion of the water evaporated in evaporation 280 may be removed as process vapor 273 and may be used to provide boilup in a stripping column. Process vapor 273 may also be used to provide heat of vaporization to flash 227 either directly or indirectly. Another portion of the water evaporated in evaporation 280 may be removed as process condensate 274 and may be further processed in methanator 185 to reduce the level of organics. Resulting stream 271 may be recycled as process condensate for mashing biomass (e.g., corn). In some embodiments, more than one process condensate streams may be generated by a retrofitted evaporation system, and each condensate stream may be sourced from a different evaporation effect and comprise a different level of organics. For example, some late effect process condensate streams may comprise low levels of organics and in some cases may bypass methanator 185 to free up capacity for early effect process condensate streams that comprise high levels of organics. Major sources of liquid for mashing biomass including streams 242, 278, and 271 may be combined in mixing step 296 along with additional water streams to form cook water stream 279 that can be used to mash biomass.

FIGS. 3A to 3E illustrate various embodiments of a retrofitted bioethanol production plant that features the removal of butanol from fermentation broth using extraction methods, for example, using batch internal liquid-liquid extraction. Alternative to removing butanol from an externally circulated fermentation broth as described herein, liquid-liquid extraction may also take place internal to the fermentor. In some embodiments, a portion of mash inside fermentation 100 may be displaced by a volume of extractant to create a biphasic mixture that becomes well mixed by the evolution of carbon dioxide that accompanies fermentation. In some embodiments, as fermentable sugars are converted to butanol, butanol may passively transfer to the extractant phase, removing butanol from the aqueous broth phase where microorganisms are located.

Figure 3A:
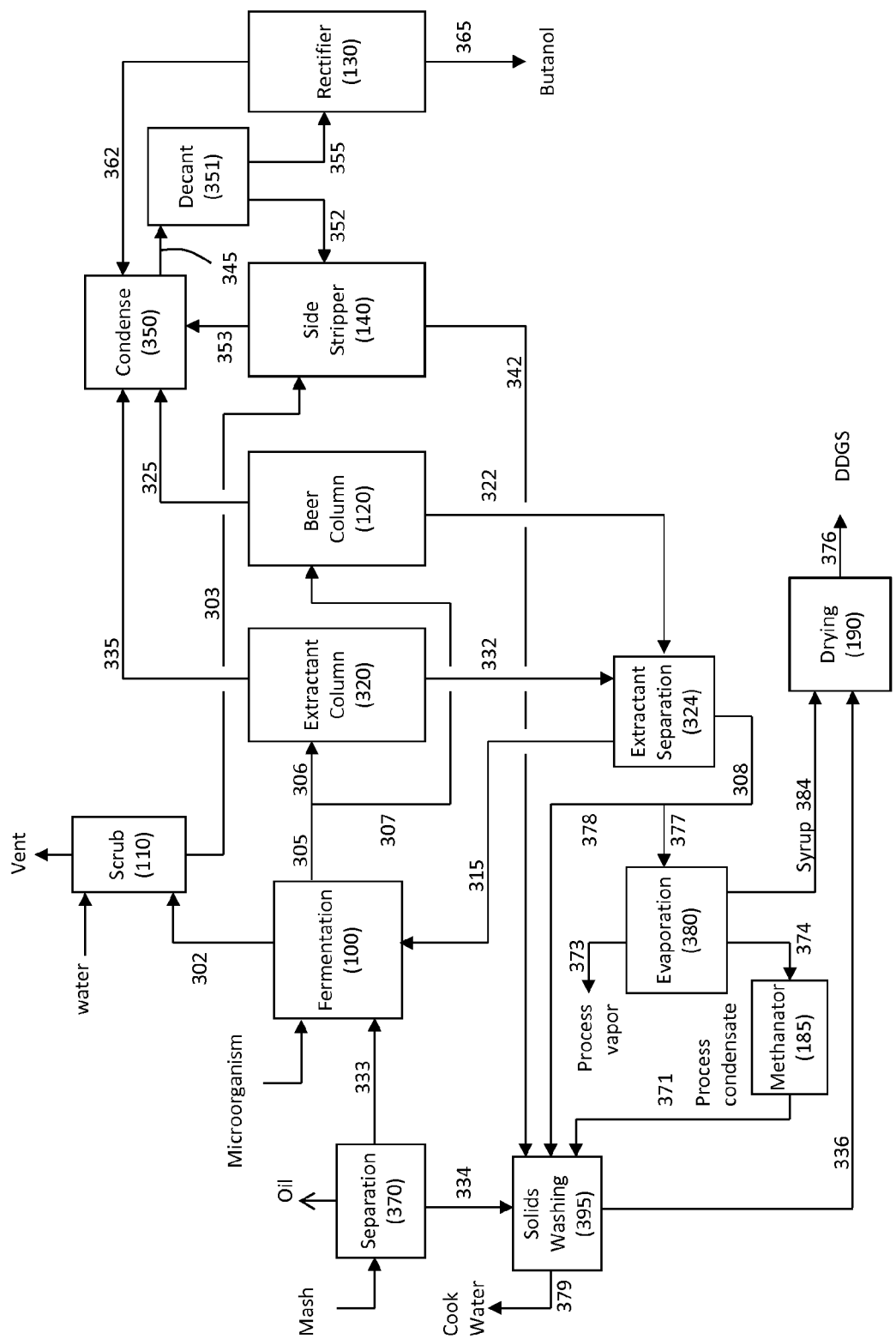
FIGS. 3A to 3E illustrate various embodiments of a retrofitted bioethanol production plant that features the removal of a product alcohol from fermentation broth using extraction methods.

Referring to FIG. 3A, liquefied mash may enter separation 370 to form wet cake 334 comprising undissolved solids and a clarified solution of dissolved fermentable sugars 333 (or thin mash 333). In some embodiments, liquefied mash may enter separation 370 to form wet cake 334, an aqueous solution of dissolved fermentable sugars 333, and an oil stream. Thin mash 333 and microorganisms may be added to fermentation 100 with extractant 315. In some embodiments, the process may include one or more fermentors. In some embodiments, this plurality of fermentors may be operated in parallel. The mash may be fermented by the microorganisms to produce butanol. Gases 302 generated during the fermentation may be vented through scrub system 110.

Scrub stream 303 may be conducted to side stripper column 140 forming vapor overhead stream 353 and liquid bottoms stream 342 that, in some embodiments, may be referred to as lutter water. Butanol and other volatile components may be recovered from vapor overhead stream 353. In some embodiments, side stripper column 140 may be a retrofit of the side stripper column used in an ethanol production and a vapor inlet may be provided at the bottom of side stripper column 140 as a heating means. In some embodiments, the vapor inlet to side stripper column 140 may be sourced in part from a vapor liquid flash device such as a unit used in lowering the pressure of hydrothermally cooked mash. In some embodiments, the vapor inlet to side stripper column 140 may be sourced in part from the partial reboil of side stripper bottoms 342.

When fermentation is complete, the vessel contents may be discharged as biphasic stream 305 and split into portions 306 and 307 that may be distributed to beer column 120 and extractant column 320 for recovery of butanol. Vapor overhead stream 325 and biphasic bottoms 322 may be removed from beer column 120 and vapor overhead stream 335 and biphasic bottoms 332 may be removed from extractant column 320. In some embodiments, beer column 120 may be a retrofit of the beer column used in ethanol production. In some embodiments, heat may be supplied to beer column 120 via a vapor inlet that may be sourced in part from a vapor liquid flash device such as a unit used in lowering the pressure of hydrothermally cooked mash. In some embodiments, the vapor inlet to beer column 120 may be sourced in part from the partial reboil of beer column bottoms 322 or the partial vaporization of process water 342 (e.g., lutter water). In some embodiments, the vapor inlet to beer column 120 may be sourced in part from an evaporation train such as the evaporation train used in concentrating thin stillage. In some embodiments, the vapor inlet to beer column 120 may be from the same source when operating in either ethanol or butanol production.

In some embodiments, extractant column 320 may be a duplicate installation of beer column 120, but operating at a different pressure. In some embodiments, heat may be supplied to extractant column 320 via a vapor inlet that may be sourced in part from a vapor liquid flash device such as a unit used in lowering the pressure of hydrothermally cooked mash. In some embodiments, the vapor inlet to extractant column 320 may be sourced in part from the partial reboil of extractant column bottoms 332 or the partial vaporization of process water (e.g., lutter water). In some embodiments, the vapor inlet to extractant column 320 may be sourced in part from an evaporation train such as the evaporation train used in concentrating thin stillage.

Vapor overhead stream 325 from beer column 120, vapor overhead stream 335 from extractant column 320, and vapor overhead stream 353 from side stripper column 140 may be conducted to condense 350 (or condenser or condensation unit) to form liquid stream 345. Liquid stream 345 may be separated in decant 351 (or decanter or decantation unit) into aqueous phase 352 and organic phase 355. If a non-condensable gas is present in streams 325 or 335, at least a portion of the non-condensable gas may be purged from condense 350 and/or decant 351 and sent to a thermal oxidizer or scrubber. Organic stream 355 may be conducted to rectifier column 130 that has been repurposed to dehydrate butanol and form bottoms stream 365 which is substantially butanol (e.g., about 98 wt % to about 100 wt %) and vapor overhead stream 362. Bottoms stream 365 may be substantially free of water (e.g., about 0 wt % to about 1 wt % water may be present). Vapor overhead stream 362 may be recycled to condense 350. In some embodiments, the composition of vapor overhead streams 325 and 335 may be controlled by introducing a portion of aqueous phase 352 and/or a portion of organic phase 355 as reflux to beer column 120 and/or extraction 320 at any favorable feed location. For example, aqueous reflux may be introduced at the top of beer column 120 and extraction 320 while organic reflux may be introduced along with feed streams 306 and 307 at some location below the top of the columns or units. In some embodiments, organic reflux may be combined with feed streams 306 and 307. The amount of extractant in vapor overhead streams 325 and 335 may be minimized by the controlled use of reflux streams.

Beer column bottoms 322 and extraction bottoms 332 may be conducted to extractant separation 324 to separate the biphasic mixtures into aqueous thin stillage 308 and organic extractant 315. Lean extractant 315 may be recycled to fermentation 100 and a portion 377 of thin stillage 308 may be concentrated by evaporation via evaporation 380 (e.g., two (2) effect by four (4) body train) to form syrup 384. In some embodiments, evaporation 380 may be a multi-effect evaporation system that is reconfigured (e.g., a two (2) effect by three (3) body plus a one (1) effect by two (2) body train) as described in U.S. Patent Application Publication No. 2011/0315541; the entire contents of which are herein incorporated by reference. The evaporators incrementally evaporate water from stream 377 and a portion of the water evaporated may be removed as process vapor 373. In some embodiments, multiple process vapor streams may be removed from multi-effect evaporation 380 and each vapor stream may be sourced at a different pressure from a different evaporation effect. These process vapor streams may be used to provide boilup to multiple stripping columns such as beer columns and extraction columns. In some embodiments, beer column 120 and extraction 320 may be operated at different pressures. Another portion of water evaporated in evaporation 380 may be removed as process condensate 374 and may be further processed in methanator 185 to reduce the level of organics in process condensate 371. In some embodiments, a portion 378 of thin stillage 308 may be recycled as backset with process condensate 371 and lutter water 342 to recover dissolved fermentables from wet cake 334 in solids washing 395. Washed cake 336 is formed and the total wash liquids generated in solids washing 395 may be recycled as cook water 379 for mashing biomass. In some embodiments, syrup 384 may be combined with washed cake 336 in dryer 190 to produce DDGS 376.

In some embodiments, non-condensable gases such as carbon dioxide may be sparged into the fermentor to promote at least partial mixing of fermentation broth and extractant and forming a biphasic mixture. At the end of a fermentation batch, the resulting mixture comprising fermentation broth, extractant, and undissolved solids may statically phase separate after the evolution of $CO_2$ gas has subsided. The biphasic mixture may be allowed to settle and separate into butanol-containing organic phase and aqueous phase. Each of the phases may be separately discharged from the fermentor. For example, the organic phase may be discharged and conducted to an extractant column and the aqueous phase may be discharged and sent to a beer well. In some embodiments, a conductivity probe may be used to detect the discharged phase from the fermentor and to appropriately direct the discharge to either a beer well or an extractant column.

Figure 3B:
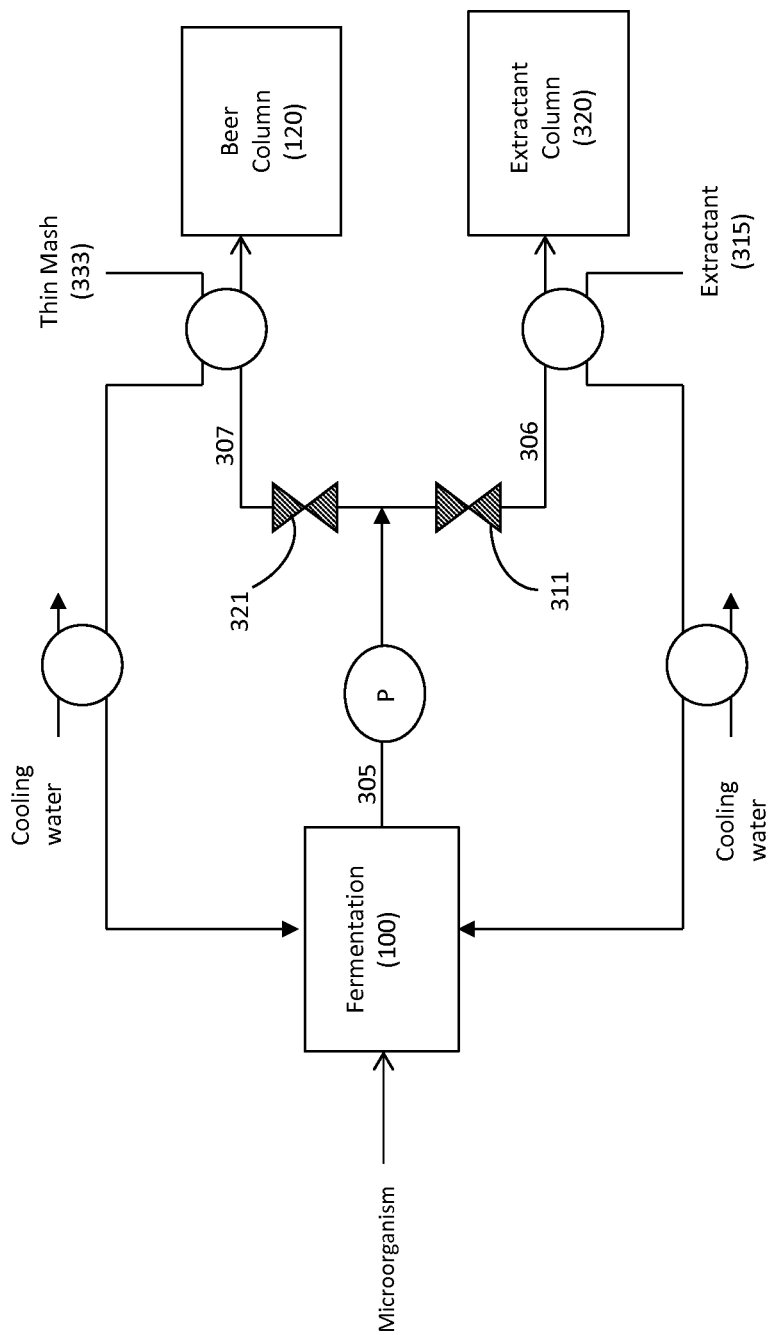

As shown in FIG. 3B, discharge 305 from fermentation 100 passes conductivity probe P and may be conducted to either line 306 (e.g., line for the organic phase) or to line 307 (e.g., line for the aqueous phase). Line 306 connects fermentation 100 to extraction 320, and line 307 connects fermentation 100 to beer column 120. Control valves 311 and 321 are provided on respective lines 306 and 307. Control valves 311 and 321 are in communication with conductivity probe P and open when a signal from conductivity probe P indicates the conductivity of discharge 305. For example, at the end of fermentation, discharge 305 from fermentation 100 may be transferred to conductivity probe P. The conductivity of discharge 305 detected by probe P may be electrically communicated to valves 311 and 321, and the appropriate valve will open so that discharge 305 may be conducted to the correct line. That is, if probe P detects the aqueous phase, valve 321 will open and valve 311 will close so that the aqueous phase may be conducted to line 307.

In some embodiments, aqueous stream 307 may be heated prior to entering beer column 120. For example, heat may be transferred from thin mash 333 to aqueous stream 307 in a heat exchanger. Thin mash 333 may be further cooled, for example, by cooling water, to a temperature that is suitable for fermentation.

In some embodiments, organic stream 306 may be heated prior to entering extraction 320. For example, heat may be transferred from extractant 315 to organic stream 306 in a heat exchanger. Extractant 315 may be further cooled, for example, by cooling water, to a temperature that is suitable for fermentation.

In some embodiments, the aqueous phase may be degassed to form degassed aqueous phase which may be conducted to beer column 120. In some embodiments, a heat transfer device (e.g., a heat exchanger) may be disposed on line 307 heating the aqueous phase prior to its introduction to beer column 120. In some embodiments, the heat exchanger may heat the aqueous phase to a temperature greater than about 70° C. prior to being fed to beer column 120. In some embodiments, the temperature may be about 70° C. to about 120° C. In some embodiments, the aqueous phase may be degassed again after the heat exchange. The organic phase and aqueous phase may be further processed as described herein.

Figure 3C:
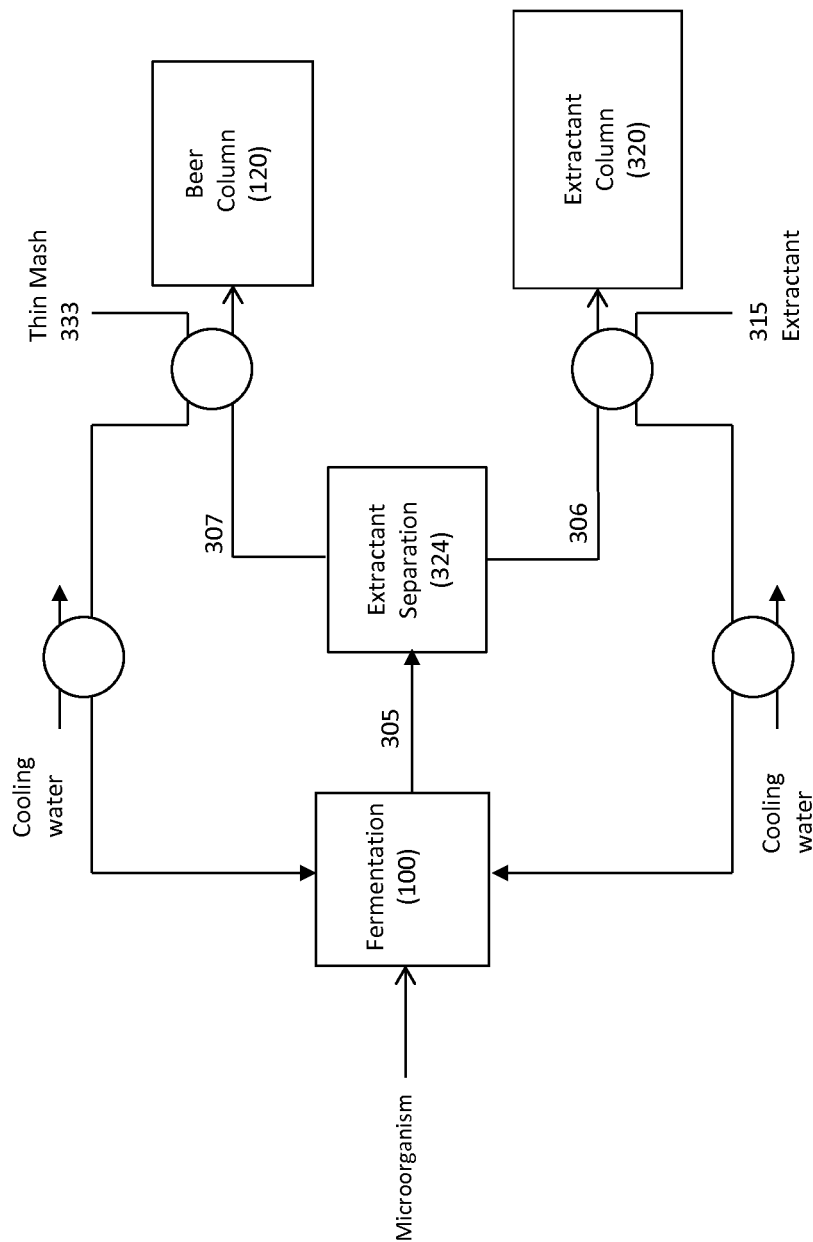

In some embodiments, a separation system as described herein may be used to facilitate the separation of the resulting mixture to form an organic phase and an aqueous phase. Another embodiment of the present invention is illustrated in FIG. 3C. Extraction separation 324 may be disposed on a line that connects fermentation 100 to beer column 120 and extraction 320. Extraction separation 324 may receive a biphasic mixture 305 from fermentation 100 and discharges (i) organic phase 306 which may be conducted to extraction 320 and (ii) aqueous phase 307 which may be conducted to beer column 120. Aqueous phase 307 may be heated by a heat exchanger (e.g., heated to about 70° C. to about 120° C.) and then conducted to beer column 120. In some embodiments, aqueous phase 307 may be degassed to form degassed aqueous phase which may be conducted to beer column 120. In some embodiments, the temperature of biphasic mixture 305 may be from about 20° C. to about 60° C. and phase separation may occur at these temperatures. In some embodiments, the temperature of the biphasic mixture 305 may be adjusted by steam injection or deactivation heater. Organic phase 306 and aqueous phase 307 may be further processed as described herein. As described in FIG. 3B, the organic phase 306 and the aqueous phase 307 may be heated prior to entry to the extraction 320 or beer column 120, respectively.

Figure 3D:
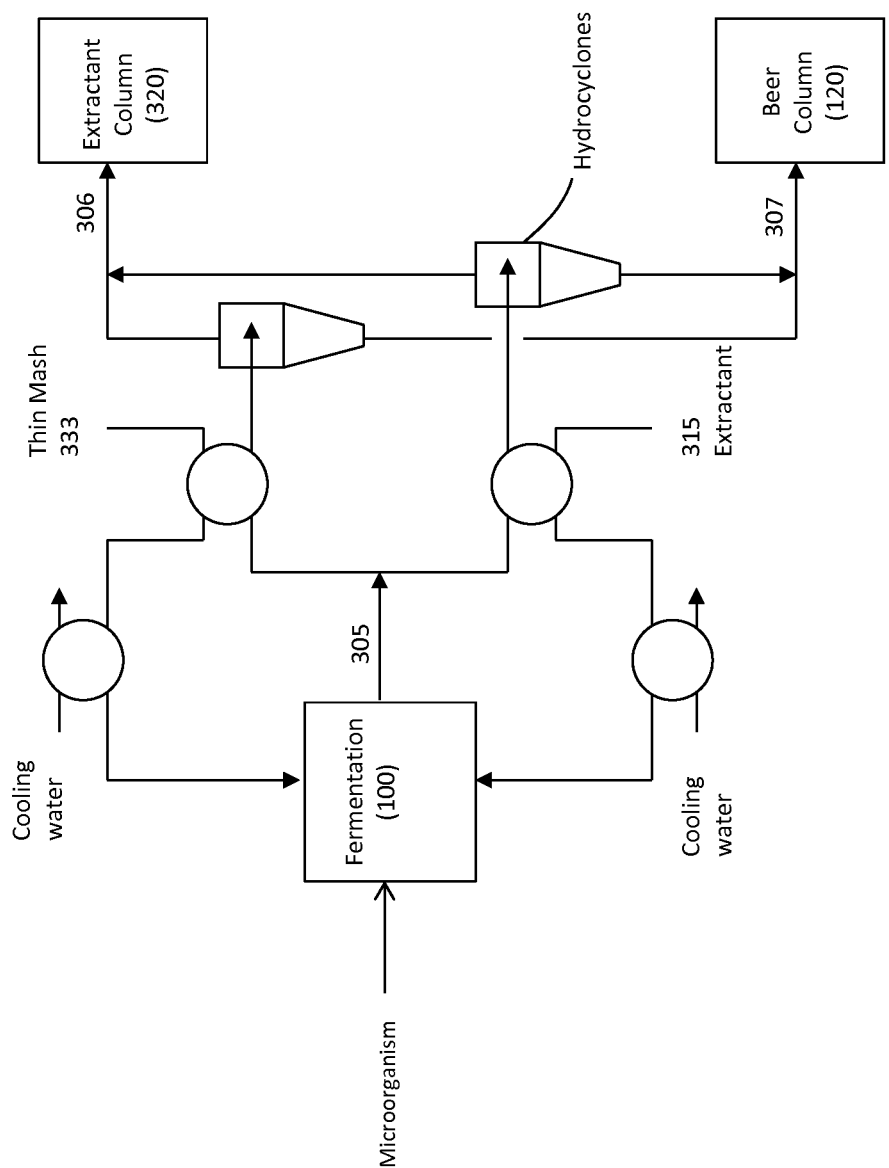

In some embodiments, it may be advantageous to increase the temperature of the biphasic mixture in order to achieve phase separation. As the biphasic mixture exits the fermentor, it may be too cold to achieve separation. As shown in FIG. 3D, biphasic mixture 305 may be divided and each portion heated separately to a temperature of about 70° C. to about 120° C. by transferring heat from thin mash 333 to a portion of biphasic mixture 305 using a heat exchanger and transferring heat from extractant 315 to another portion of biphasic mixture 305 using another heat exchanger. After absorbing heat, the two portions of biphasic mixture 305 may be conducted through a battery of hydrocyclones to effect separation of immiscible phases. One advantage to separating heated motive fluid phases in hydrocyclones may be the avoidance of a potential conflict with using other motor driven phase separation equipment (e.g., three-phase centrifuge) to process a stream containing flammable components (e.g., butanol). The overflows of the hydrocyclones may be collected to form organic phase 306 and the underflows of the hydrocyclones may be collected to form aqueous phase 307. Organic phase 306 may be conducted to extraction 320 and aqueous phase 307 may be conducted to beer column 120 for further processing as described herein. In some embodiments, aqueous phase 307 may be degassed in a beer well.

Figure 3E:
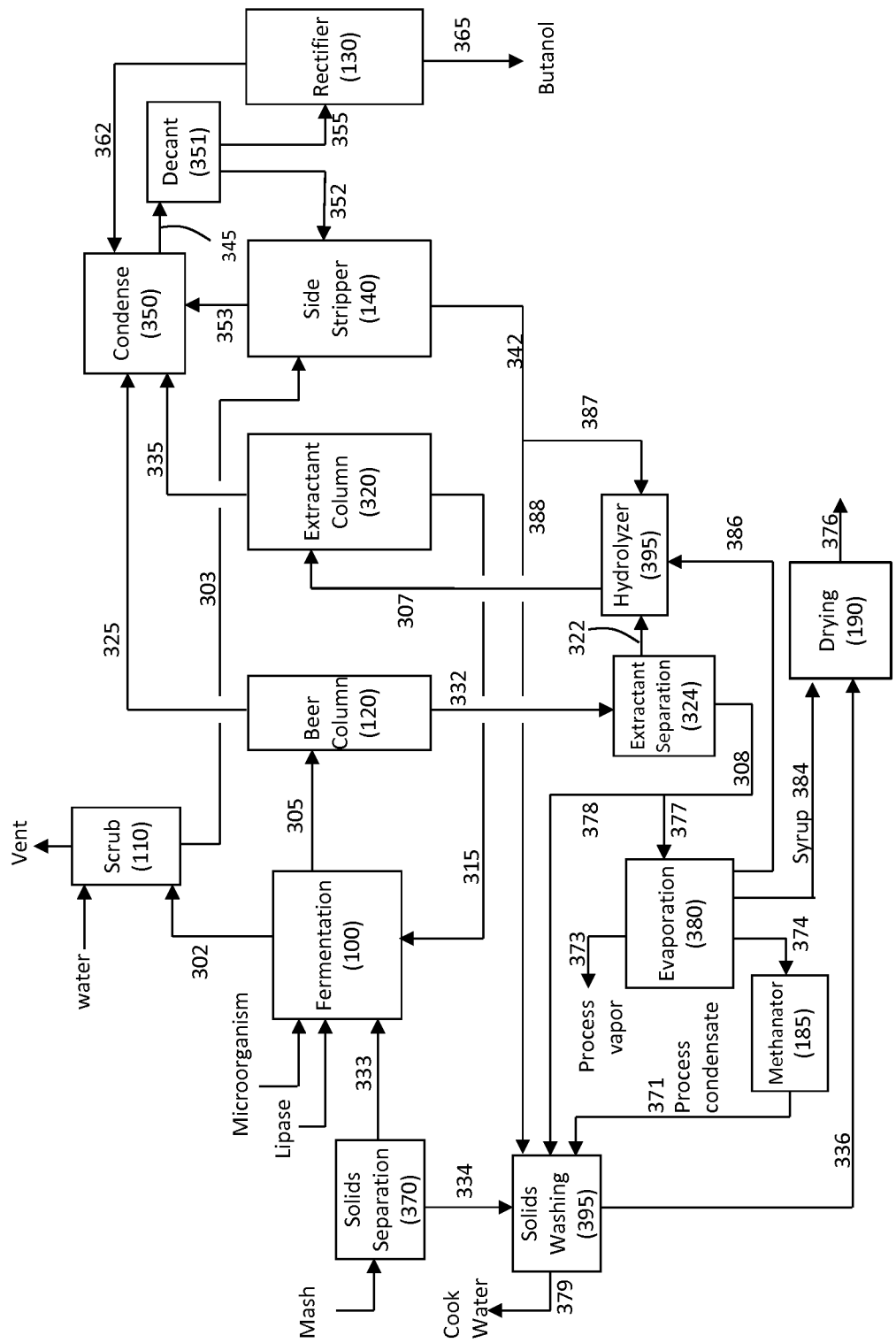

FIG. 3E illustrates a modification of the process shown in FIG. 3A where the extractant is a fatty acid derived from corn oil. An esterification catalyst may be provided to promote chemical reaction between fatty acid and butanol to form fatty ester. An enzyme (e.g., lipase) may be added with the microorganism, thin mash 333, and extractant 315 in fermentation 100 so that a portion of butanol produced during fermentation may be chemically sequestered as fatty acid butyl ester. Fermentation discharge 312 may contain some butanol which may be recovered in beer column 120. Biphasic bottoms stream 332 may contain the ester product and can be separated in extractant separation 324 to form fatty ester stream 322 and thin stillage 308. In some embodiments, thin stillage 308 may comprise the ester and when a portion 377 is evaporated in evaporation 380, the ester may be recovered as stream 386. The combined fatty ester contained in streams 322 and 386 may be chemically treated in hydrolyzer 395 with a portion 387 of lutter water 342 to convert a portion of fatty ester to fatty acid and butanol. The product of hydrolyzer 395 may be biphasic stream 307 and butanol may be recovered in extraction 320. The bottoms of extraction 320 is stream 315 and may comprise fatty acid for recycle to fermentation 100.

In another embodiment of the present invention, a retrofitted bioethanol production plant may be modified to incorporate batch internal extraction. For example, extractant may be added directly to a fermentor comprising feedstock and microorganism. At the end of fermentation, the resulting mixture comprising fermentation broth, extractant, and undissolved solids may statically phase separate. In some embodiments, a separation system as described herein may be used to facilitate the separation of the resulting mixture to form an organic phase and an aqueous phase. In another embodiment, the resulting mixture may be discharged in its entirety to distillation for recovery of product alcohol such as butanol.

As another example of batch internal extraction in a retrofitted bioethanol production plant, an external cooling loop may be retrofitted to supply extractant to a fermentor. In some embodiments, an exit line or return line of an external cooling loop may be modified to include an extractant supply port that supplies extractant to the external cooling loop. In a retrofitted bioethanol production plant, the modified external cooling loop may include valve switches and/or line breaks allowing the production plant to be easily converted between a bioethanol production plant and a biobutanol production plant. That is, the extractant supply port could be easily taken off-line during bioethanol production and easily returned on-line for butanol production. In addition, by modifying the external cooling loop, it may not be necessary to modify the fermentor to incorporate an extractant supply port allowing the production plant to be easily converted between a bioethanol production plant and a biobutanol production plan. In some embodiments, the return line may be modified to include an extractant supply port and this configuration can reduce fouling of the heat exchanger of the external cooling loop.

In another embodiment of the present invention, at the end of fermentation, the biphasic mixture may be discharged from the fermentor and may be conducted to distillation, whereby the biphasic mixture may be stripped of its butanol. The resulting post-distillation biphasic mixture may then be separated. In some embodiments, the post-distillation phase separation may occur before, after, or simultaneously with solids removal from the post-distillation biphasic mixture. In some embodiments, post-distillation phase separation may be conducted on whole stillage (i.e., prior to solids removal), and in some embodiments, post-distillation phase separation may be conducted on thin stillage (i.e., after solids removal but before evaporation of stillage into syrup).

Figure 4:
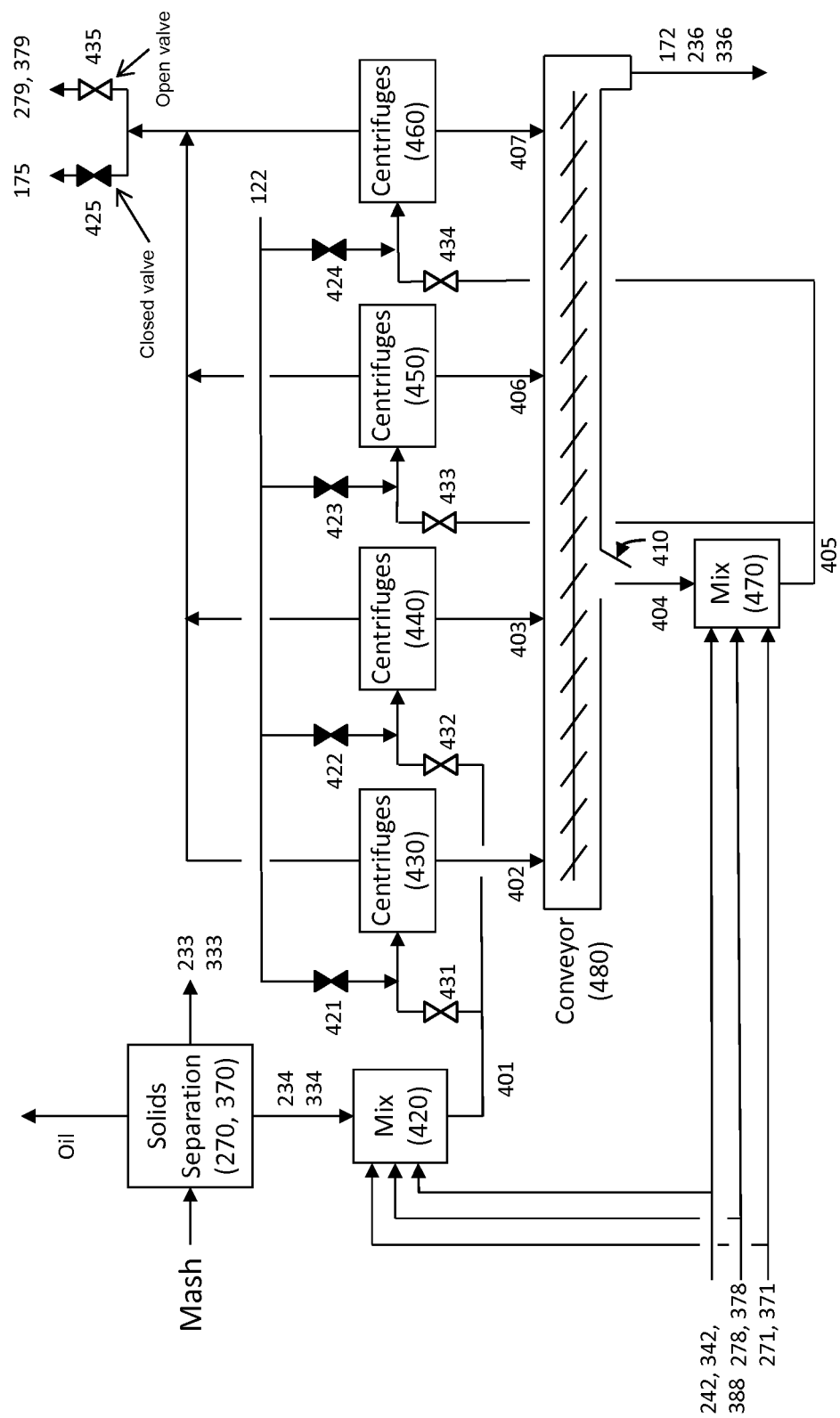
FIG. 4 illustrates an embodiment for solids separation and further processing of the solids.

In some embodiments of the present invention, feedstock may be processed as shown in FIG. 4. FIG. 4 illustrates an embodiment of a retrofitted bioethanol production plant including means to process undissolved solids. Some processes and streams appear in FIG. 4 with the same name and numbering as used in FIGS. 1, 2B, 3A, and 3E for the purpose of identifying these processes and systems as being the same or similar as described in FIGS. 1, 2B, 3A, and 3E. For example, separation (270, 370) as described herein may be used to separate liquefied mash to form wet cake (234, 334) and thin mash (233, 333). The wet cake (or solids) may be further processed in solids washing (295, 395) to produce a liquid stream (279, 379) and a washed wet cake (236, 336). The equipment used in solids washing (295, 395) may include repurposed centrifuges 430, 440, 450, and 460 connected to conveyor 480. That is, the existing centrifuges and conveyor used in a bioethanol production plant as represented by solids separation 170 in FIG. 1 to separate whole stillage 122 forming wet cake 172 and thin stillage 175 may be repurposed for solids washing (295, 395). Piping may be changed and valves may be added for the configuration shown in FIG. 4 that allows mash slurry to be processed through centrifuges 430, 440, 450, and 460 with no modification to the equipment. Open valves are indicated in white and closed valves are indicated in black. Wet cake 234 or 334 may be combined in mixing 420 with at least a portion of any of the aqueous streams 242, 342, 388, 278, 378, 271, 371, or mixtures thereof as described herein to form slurry stream 401. Slurry stream 401 may be transferred to centrifuges 430 and 440 via valves 431 and 432 to form wet cakes 402 and 403. Wet cakes 402 and 403 may be combined in conveyor 480. In some embodiments, conveyor 480 includes a trough that guides movement of the wet cake. Wet cake may be moved along the trough by various methods known commercially such as rotating screws, revolving belts, or drag chains, and the like. A modification may be made to the trough of conveyor 480 by installing a hatch or hinged door 410 along the bottom of the trough at a position downstream of the point of entry of wet cake 403. When the hatch is open, the wet cake may exit the trough via stream 404 as the wet cake passes over the hatch opening. Stream 404 may be introduced to mixing 470 and may be combined with at least a portion of any of the aqueous streams 242, 342, 388, 278, 378, 271, 371, or mixtures thereof to form slurry stream 405. Slurry stream 405 may be conducted to centrifuges 450 and 460 via valves 433 and 434 to form wet cakes 406 and 407. Wet cakes 406 and 407 may be combined in conveyor 480 downstream of hatch 410 and conveyed to the exit to form stream 236 or 336. The centrates from centrifuges 430, 440, 450, and 460 may be combined and exit via valve 435 to form aqueous stream 279 or 379. This configuration would allow the production plant to revert to whole stillage processing without requiring any mechanical changes to the piping or equipment. For example, if hatch door 410 and valves 431 through 435 were closed and valves 421 through 425 were opened, then whole stillage 122 may be introduced in parallel through valves 421, 422, 423, and 424 to centrifuges 430, 440, 450, and 460 and thin stillage 175 may exit valve 425 and wet cake 172 may be discharged from the end of the conveyor.

In some embodiments, wet cake separated from liquefied mash may be transferred to a dryer by means of a belt conveyor system, or it may be re-slurried and transferred by pump. The wet cake may be removed from liquefied mash by any separation device as described herein. The distance between the separation device and dryer may be significant, which could require a long conveyor. To reduce the costs of a reversible process, the separation device may be located in close proximity to the dryer. A process with this layout may also reduce the rail installation expense by co-locating the feedstock, product, and co-product rail unloading and loading facilities. In some embodiments, the separation device may be a retrofit of a whole stillage separation device in its existing location. In this case, the wet cake may be conveyed to dryers using the same transport system. Piping and valve changes may manage the reversible use of the separation device to receive either liquefied mash or whole stillage and to discharge centrate as thin mash or thin stillage, respectively. A modification may be made to conveyors to reversibly switch between parallel and series configuration of the multiple separation equipment. In an ethanol manufacture mode, the separation device for whole stillage may comprise multiple centrifuges, each operating in parallel on a portion of the stillage. The wet cake that each produces may be combined using a common conveying system. To separate wet cake from liquefied mash using the same separation equipment, the conveyors may be modified at certain locations along their length such that wet cake may be moved in segments and re-slurrying and re-centrifuging of the wet cake may take place between each segment.

In some embodiments of a reversible retrofit process, the separation device for liquefied mash may be located in close proximity to the liquefaction and fermentation areas. It may be desirable to minimize the path length of a mash stream that is rich in fermentable sugars to avoid excessive risk of contamination. Liquefied mash may enter the separation device and the resulting thin mash with a reduced level of suspended solids may be forwarded to fermentation. Reversibility may be achieved by manipulating installed manual valves that allow liquefied mash to bypass the separation device. Wet cake (undissolved solids) removed by the separation device may retain fermentable carbon substrates or other byproducts that are desirable to recover. To recover the fermentable carbon substrates or other byproducts, the wet cake may need to be re-pulped in an aqueous medium that comprises little or no fermentable carbon substrates and then be separated. The cook water that comprises mostly process condensate produced by the stillage evaporators and the side stripper column may be used to re-pulp the wet cake.

Figure 5:
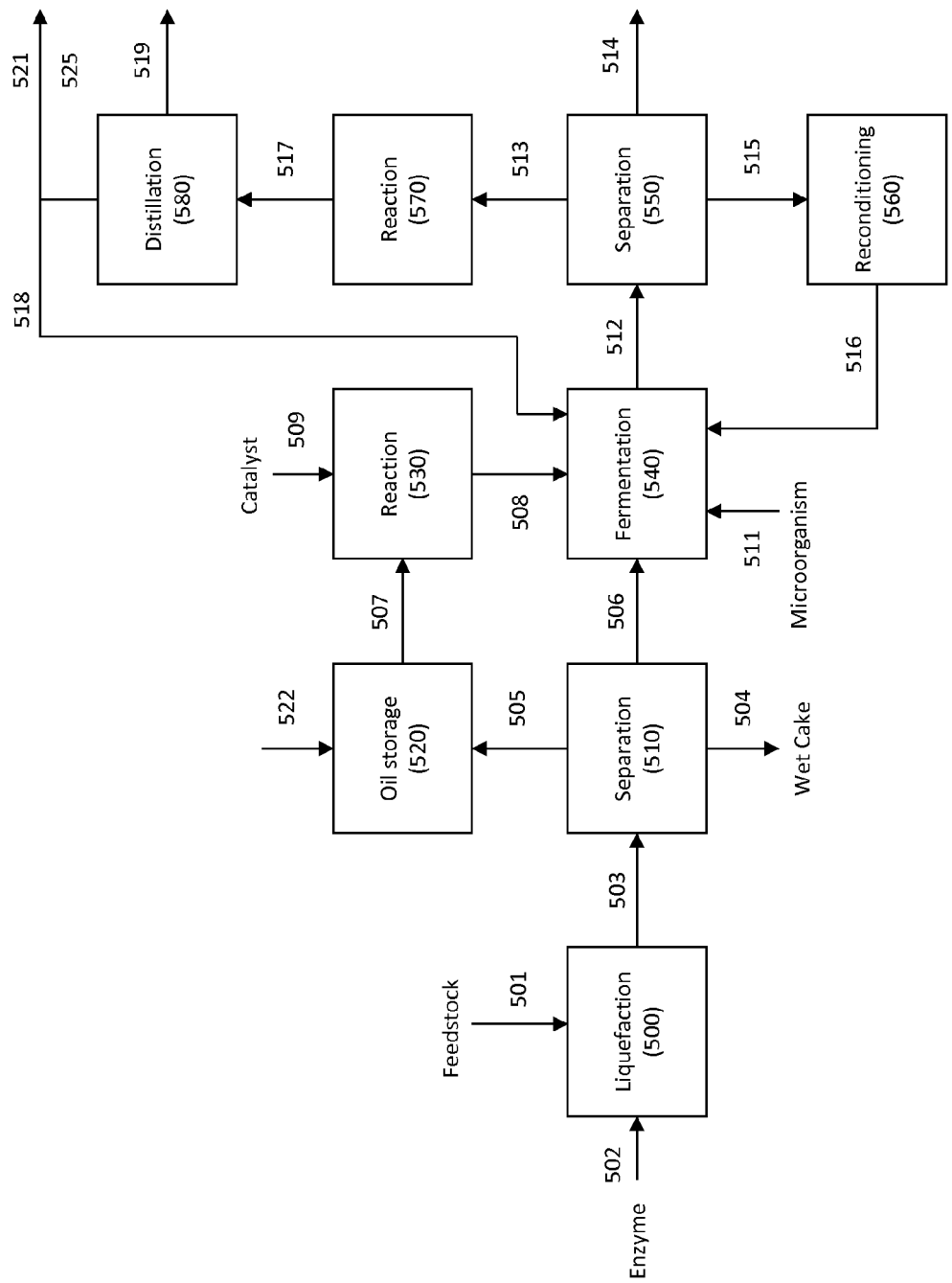
FIG. 5 illustrates an embodiment of the process and equipment that may be utilized to produce a product alcohol using a reactive liquid extraction process.

During fermentative production of butanol, the amount of butanol in the fermentation broth may be maintained below a desired concentration by removing butanol from the fermentation broth using an extractant such as fatty acids. In some embodiments, butanol removal may be achieved by esterification with carboxylic acid in the presence of a catalyst to produce butyl esters. For a description of methods and systems for extracting product alcohol by formation of alcohol esters see, for example, U.S. Patent Application Publication No. 2011/040856; the entire contents of which are herein incorporated by reference. FIG. 5 illustrates an embodiment of the processes and systems that may be utilized to produce product alcohol using a reactive liquid extraction process. Feedstock 501 and enzyme 502 enter liquefaction 500 hydrolyzing starches to sugars and forming feedstock slurry 503. Feedstock slurry 503 may be transferred to optional separation 510. Separation 510 may be any separation device capable of separating liquids and solids such as decanter bowl centrifugation, three-phase centrifugation, disk stack centrifugation, filtering centrifugation, decanter centrifugation, filtration, vacuum filtration, beltfilter, pressure filtration, filtration using a screen, screen separation, grating, porous grating, flotation, hydrocyclone, filter press, screwpress, gravity settler, vortex separator, or combinations thereof. Separation of feedstock slurry 503 produces liquid phase 506 and solid phase 504 (e.g., undissolved solids). Liquid phase 506 may be added to fermentation 540, and solid phase 504 (or "wet cake") may be further processed. For example, wet cake 504 may include starch and/or sugar, and may be washed with water to recover the starch and/or sugar. In some embodiments, oil contained in feedstock slurry 503 may optionally be separated and separated oil 505 may be transferred to oil storage unit or tank 520. In some embodiments, oil may not be separated from feedstock slurry 503 and may be transferred to fermentation 540 as a component of liquid phase 506. In some embodiments, oil from feedstock slurry 503 may be in the wet cake 504. In some embodiments, wet cake 504 may be further processed to form DDGS which can be used to produce animal feed. In some embodiments, if oil is separated from the feedstock slurry, then the wet cake produced may comprise a low fat content; and this low fat wet cake may be used to produce a low fat animal feed. In some embodiments, if oil is not separated from the feedstock slurry, then the wet cake produced may comprise a high fat content; and this high fat wet cake may be used to produce a high fat animal feed.

In some embodiments, oil from another source 522 may be charged to oil storage unit 520. In some embodiments, oil 507 from oil storage unit 520 and catalyst 509 may be transferred or added to reaction 530 to convert triglycerides from oil 507 to carboxylic acids, forming carboxylic acid/glycerol mixture 508. In some embodiments, catalyst 509 may be an enzyme such as an esterase, lipase, phospholipase, or lysophospholipase. Examples of enzymes that may be used are described in U.S. Patent Application Publication No. 2011/0312043, the entire contents of which are herein incorporated by reference.

In some embodiments, carboxylic acid/glycerol mixture 508 may be transferred to fermentation 540. In some embodiments, mixture 508 may also comprise catalyst. In some embodiments, mixture 508 may be heated to inactivate catalyst 509 prior to addition to fermentation 540. In some embodiments, if oil is present in liquid phase 506, catalyst 509 may be added directly to fermentation 540 to convert triglycerides from the oil to carboxylic acids. In some embodiments, carboxylic acid may be added directly to fermentation broth, liquid phase 506, or fermentation 540 as free fatty acid from another source. Microorganism 511 that produces product alcohol may be added to fermentation 540. In some embodiments, microorganism 511 may be genetically modified to produce product alcohol such as butanol. In some embodiments, product alcohol produced by microorganism 511 may react with carboxylic acids to produce alcohol esters and in some embodiments, the alcohol esters may be extracted from the fermentation broth. In some embodiments, butanol produced by microorganism 511 may react with carboxylic acids to produce butyl esters and in some embodiments, the butyl esters may be extracted from the fermentation broth. In some embodiments, carboxylic acids may be an extractant.

Stream 512 containing the contents of fermentation 540 may be transferred to separation 550. In some embodiments, stream 512 may comprise fermentation broth, microorganisms, product alcohol, extractant, alcohol esters, and/or additional byproducts. In some embodiments, stream 512 may be separated by separation 550 forming a stream comprising microorganism 515, aqueous phase 514, and organic phase 513. Separation 550 may be any separation device capable of separating liquids and solids as described herein including a three-phase centrifuge. In some embodiments, stream 512 may be continuously removed from fermentation 540 and conducted to separation 550. In some embodiments, aqueous phase 514 and stream 515 may be combined and returned or recycled to fermentation 540. In some embodiments, the microorganism from stream 515 may be conducted to reconditioning 560 generating reconditioned microorganism stream 516 which may be returned or recycled to fermentation 540.

In some embodiments, stream 512 from fermentation 540 may comprise a biphasic mixture and may be conducted to separation 550 to separate the biphasic mixture into ester-containing organic phase 513 and aqueous phase 514. Separation 550 may be achieved using any methods known in the art including, but not limited to, siphoning, aspiration, decantation, centrifugation, gravity settler, membrane-assisted phase splitting, hydrocyclone, and the like. Organic phase 513 may be transferred to reaction 570, where the esters (e.g., butyl esters) may be hydrolyzed by a catalyst to form a mixture 517 comprising butanol and carboxylic acid. Mixture 517 may be transferred to distillation 580 for separation and generating butanol stream 519 and carboxylic acid stream 525. A portion 518 of carboxylic acid stream 525 may be recycled to fermentation 540. Another portion 521 of carboxylic acid stream 525 may be furthered process, for example, used as an additive for an animal feed product. In some embodiments, reaction 570 and distillation 580 may be occur in a single unit, such as a reactive distillation column. In some embodiments, acyl glycerides are provided from the oil in the feedstock slurry. In some embodiments, the acyl glycerides may be catalytically hydrolyzed to carboxylic acid using catalyst as described herein.

Liquefaction 500 and fermentation 540 may be used in the production of any product alcohol. Equipment used for separation 510 may be new equipment that is utilized for production of any product alcohol or it may be bypassed during production of ethanol. Oil storage unit 520 may be used if separation 510 is in service to allow for adjusting oil content of the animal feed product or sale of oil product. Reactions 530 and 570 and distillation 580 will likely not be utilized during ethanol production and may be put in service or taken out of service. Separation 550 and reconditioning 560 may be utilized during production of any alcohol when separation 510 is in service to remove undissolved solids.

Figure 6A:
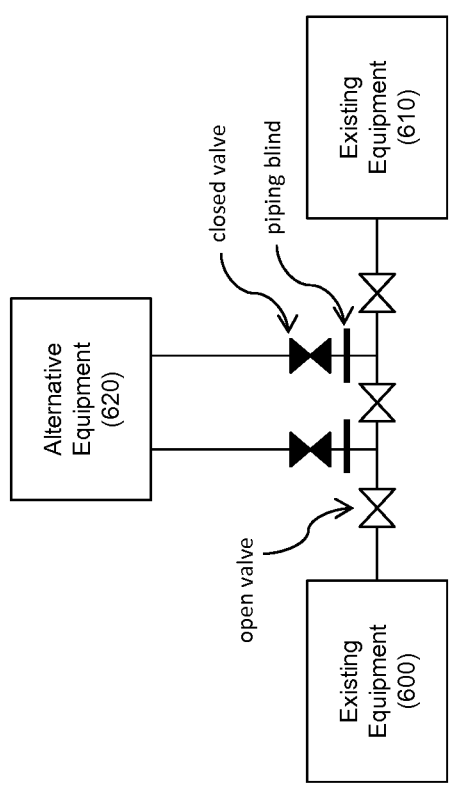
FIGS. 6A and 6B illustrate modifications of equipment of a retrofit ethanol plant.
Figure 6B:
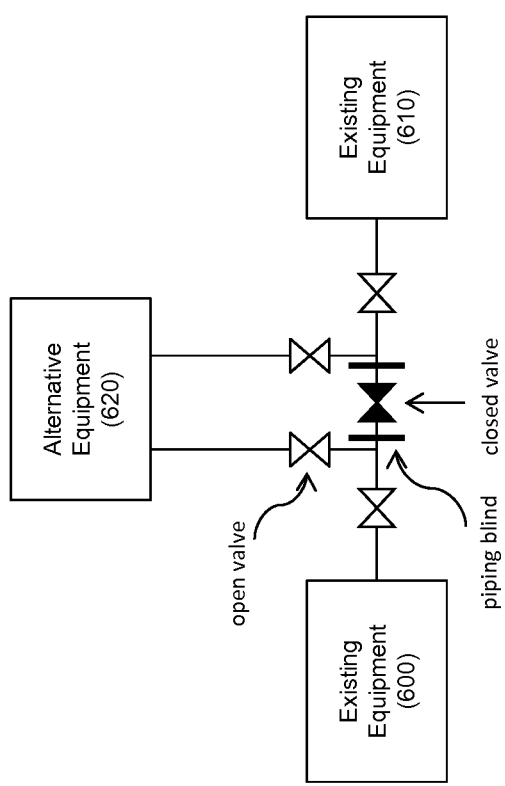

This equipment may be put in service or taken out of service by arranging piping, valves, and pipe blinds. For example, as illustrated in FIGS. 6(a) and 6(b), valves and piping blinds may be used to put equipment in service or take it out of service. Referring to FIG. 6(a), valves may be opened ("open valves") to use existing equipment 600 and existing equipment 610; and valves ("closed values") and piping blanks may be used to take alternative equipment 620 out of service. In the systems described herein, if separation of feedstock slurry is not necessary, then the equipment used for separation of feedstock slurry (e.g., alternative equipment 620) may be taken out of service by the installation of valves and piping blinds; and feedstock slurry from liquefaction (e.g., existing equipment 600) may be conducted, for example, to a fermentor (e.g., existing equipment 610) as shown in FIG. 6(a). If separation of feedstock slurry will be implemented, then the valves to the separation equipment (e.g., alternative equipment 620) may be opened ("open valve"); and valves and piping blinds may be installed to close the piping from liquefaction to the fermentor (e.g., existing equipment 610) as shown in FIG. 6(b). Also, as described herein, product alcohol may be partially removed from fermentation broth by vaporization (see, e.g., U.S. Patent Application Publication No. 2012/0035398 and U.S. Patent Application Publication No. 2012/0211348; the entire contents of each are herein incorporated by reference). Much of the equipment required for product alcohol vaporization and condensation may be installed as an addition to the fermentor cooling loop utilized in most ethanol plants.

As described herein, butanol may be recovered from fermentation broth using a number of methods including distillation (see., e.g., U.S. Patent Application Publication No. 2011/0162953; U.S. Patent Application Publication No. 2011/0162954; U.S. Patent Application Publication No. 2011/0288345; U.S. Patent Application Publication No. 2011/0288344; the entire contents of each are herein incorporated by reference). For example, butanol may be recovered from a fermentation broth using a two-column continuous distillation process. The liquid stream may be stripped in an existing beer column of a retrofit bioethanol production plant. In some embodiments, the existing beer column may be replaced with a larger diameter beer column to provide sufficient cross-sectional area for butanol stripping. The larger diameter beer column may be designed to maximize cross-sectional area productivity including, for example, operation at higher pressures. To revert to a bioethanol production plant, the larger diameter beer column may be exchanged with the original beer column. In some embodiments, the liquid stream may be preheated prior to stripping butanol. If, for example, liquid-liquid extraction is used to recover butanol, extractant may be recovered from the beer column by density-based separation including centrifugation, settling, or cycloning. The recovered extractant may be further processed by filtration and/or purification and in some embodiments, the extractant may be recycled.

Vapors from the beer column may be condensed. In some embodiments, the vapors may comprise carbon dioxide, water, and butanol. In some embodiments, the vapors may be compressed, further condensed, and vented to a scrubber for recovery of residual butanol. Condensate may be conducted to a decanter for separation into an aqueous phase and an organic phase (e.g., butanol-rich phase). The aqueous phase may be returned to the beer column or it may be used as reflux. For example, if the aqueous phase is used as reflux, a liquid stream or beer may be fed to the beer column one or more trays below the reflux.

The organic phase from the decanter may be conducted to an existing rectifier of a retrofit bioethanol production plant. In some embodiments, the organic phase may be conducted to a modified existing rectifier or a newly designed rectifier. In some embodiments, the organic phase may be preheated prior to being sent to the rectifier. Overheads from the rectifier column may be condensed and the condensate may be returned to a decanter for recovery of residual butanol. In some embodiments, the overheads may comprise butanol and water as an azeotrope composition.

In some embodiments, the equipment that may be used to retrofit an existing bioethanol production plant would include a condenser for the beer column, a decanter, and a reboiler which may be installed at the base of a rectifier. In some embodiments, the existing condenser for the rectifier may be modified to use as the condenser for the beer column.

Figure 7:
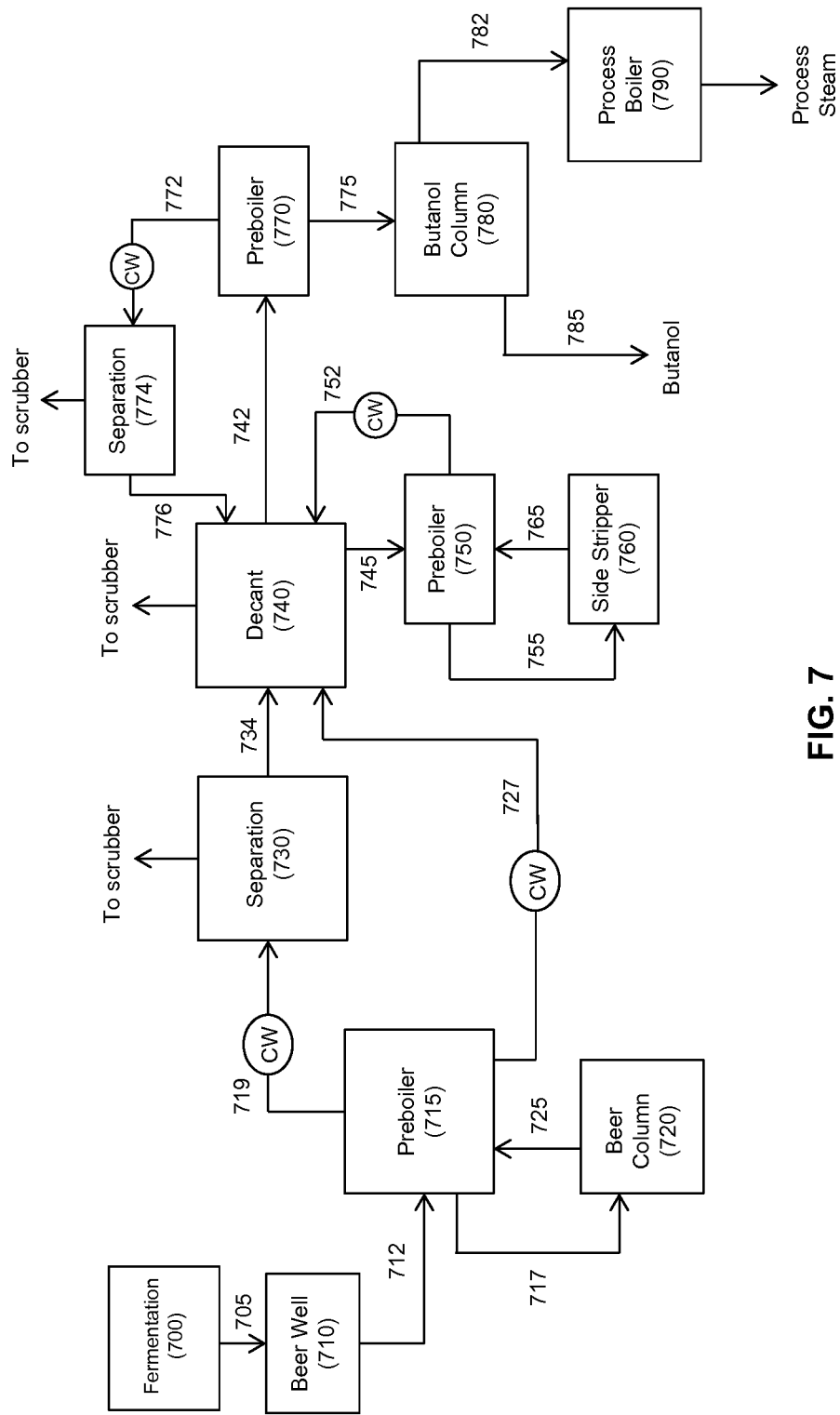
FIG. 7 illustrates a process for recovery a product alcohol using a distillation process.

In some embodiments, butanol may be recovered from a liquid stream using a three-column continuous distillation process as illustrated in FIG. 7. As an example of an embodiment of a three-column continuous distillation process, stream 705 comprising butanol may be conducted from fermentation 700 either continuously or batch-wise to beer well 710. From beer well 710, stream 712 comprising butanol may be conducted to preboiler 715 and then stream 717 (e.g., comprising less butanol than stream 712) from preboiler 715 may be conducted to beer column 720. One advantage of a preboiler is to reduce the volume of the stream conducted to a beer column and thereby reduce the amount of heat (e.g., steam) needed to strip butanol from the stream. In addition, a preboiler may remove carbon dioxide from the stream conducted to a beer column and enable more efficient energy recovery by increasing the dew point of the vapors of the beer column. In some embodiments, preboiler 715 may be a single-stage partial vaporizer or a multi-stage stripping column. In some embodiments, beer column 720 may be the existing beer column in a retrofit bioethanol production plant. In some embodiments, preboiler 715 may be at a lower pressure than beer column 720. In some embodiments, vapor stream 725 (e.g., comprising water and butanol) from beer column 720 may be condensed in preboiler 715 and further condensed by cooling water (CW) to form condensate 727. Condensate 727 may be conducted to decant 740 (or decanter or decantation unit).

In some embodiments, stream 712 may be partially flashed at a low pressure in preboiler 715 producing flash stream 719 (e.g., comprising carbon dioxide, water, and butanol). In some embodiments, about 10% to about 90% of butanol in stream 712 may be flashed in preboiler 715. In some embodiments, about 10% to about 70% or about 10% to about 50% of butanol in stream 712 may be flashed in preboiler 715. Flash stream 719 may be condensed, for example, by cooling water (CW) or other cool stream and this condensate may be conducted to separation 730 to remove carbon dioxide which may then be vented to a scrubber to recover residual butanol. Separation of carbon dioxide may be accomplished by any gas/liquid separation means including, for example, vented cyclone or settling tank. In some embodiments, carbon dioxide may be pressurized, for example, by a compressor or blower prior to venting to a scrubber. Following separation 730, stream 734 may be conducted to decant 740. In some embodiments, decant 740 may be vented to a scrubber.

In some embodiments of a retrofit without a preboiler, the feed for beer column 720 may be preheated by heat transfer from vapor of beer column 720. In some embodiments, vapor of beer column 720 may be condensed in a stagewise process and the condensate may be conducted to decantation (or decantation unit). The stagewise condensation process may be performed in a series of two or more condensers or a dephlegmator condenser.

In some embodiments, the contents of decant 740 may comprise a vapor phase, organic phase (or stream) 742 (e.g., butanol-rich phase), and aqueous phase (or stream) 745 (e.g., water-rich phase). Aqueous phase 745 from decant 740 may be conducted to preboiler 750 and stream 755 from preboiler 750 may be conducted to side stripper 760. In some embodiments, side stripper 760 may also be a lutter water column. In some embodiments, preboiler 750 may be at a lower pressure than side stripper 760. In some embodiments, preboiler 750 may be a single-stage tank or a multi-stage column. In some embodiments, preboiler 750 may be heated by condensation of vapors from side stripper 760. Vapors (e.g., comprising water and butanol) from preboiler 750 may be condensed with cooling water (CW) forming condensate 752 and condensate 752 may be conducted to decant 740. Vapor stream 765 (e.g., comprising water and butanol) from side stripper 760 may be condensed by indirect cooling in preboiler 750 and further cooled by cooling water and then conducted to decant 740. In some embodiments, side stripper 760 may be heated by injection of process steam from evaporation. In some embodiments, side stripper 760 of an existing bioethanol production plant may be modified to increase its hydraulic capacity to accommodate the hydraulic flow of stream 755. For example, side stripper 760 may be modified by repacking or modifications to the distributor or collection systems. In some embodiments, these modifications may be reversible. In some embodiments, side stripper 760 may be replaced with a butanol side column.

In some embodiments, organic phase 742 may be conducted to preboiler 770 for removal of water and/or carbon dioxide. In some embodiments, about 10% to about 90% of organic phase 742 may be vaporized to form flash stream 772 (e.g., comprising carbon dioxide, water, butanol). In some embodiments, about 10% to about 70% or about 10% to about 50% of organic phase 742 may be vaporized to form flash stream 772. In some embodiments, organic phase 742 may be indirectly heated with vapor from beer column 720, side stripper 760, vapor stream 782, or other heat source. Flash stream 772 may be condensed, for example, by cooling water (CW) or other cool stream and this condensate may be conducted to separation 774 to remove carbon dioxide which may then be vented to a scrubber to recover residual butanol. Separation of carbon dioxide may be accomplished by any gas/liquid separation means including, for example, vented cyclone or settling tank. In some embodiments, carbon dioxide may be pressurized, for example, by a compressor or blower prior to venting to a scrubber. Following separation 774, stream 776 may be conducted to decant 740. In some embodiments, decant 740 may be vented to a scrubber.

Following removal of water and/or carbon dioxide via preboiler 770, stream 775 may be conducted to butanol column 780. By partially vaporizing organic phase 742, the amount of steam required by butanol column 780 to strip water from stream 775 is reduced. In addition, by removing carbon dioxide from organic phase 742 via preboiler 770, the dew point of vapor stream 782 from butanol column 780 is increased and thus, enable a more efficient heat integration. Bottoms stream 785 which comprises butanol may be collected as product. In some embodiments, bottoms stream 785 may be cooled with cooling water or other cool streams.

In some embodiments, butanol column 780 may be heated via a reboiler which is supplied with powerhouse steam. In some embodiments, butanol column 780 may be an existing rectifier column in a retrofit bioethanol production plant, a modified rectifier column in a retrofit bioethanol production plant, or a new distillation column. For example, an existing rectifier column may be modified to include a reboiler that may be heated with powerhouse steam or re-rated to operate at supra-atmospheric pressure (e.g., addition of stiffening rings, reinforcing gussets, and the like). In some embodiments, these modifications may be reversible. In some embodiments, butanol column 780 may be a new column designed to operate at supra-atmospheric pressure. In some embodiments, butanol column 780 may be heated by indirect exchange with powerhouse steam in a reboiler. In some embodiments, butanol column 780 may operate at supra-atmospheric, atmospheric, or sub-atmospheric pressure.

In some embodiments, vapor stream 782 may be collected from butanol column 780 and may be conducted to process boiler 790 for condensation and generation of process steam. This process steam may be used to provide heat as needed in a production plant, for example, to provide heat for a beer column or side stripper. Process steam from process boiler 790 may be at supra-atmospheric, atmospheric, or sub-atmospheric pressure. In some embodiments, water supply for the process boiler 790 may be condensate from evaporators or may be bottoms from a side stripper. In some embodiments, process boiler 790 may be operated with manual blowdowns or automatic blowdowns as a means to remove impurities. In some embodiments, vapor stream 782 may be used to provide heat for one or more evaporators. In some embodiments, vapor stream 782 may be compressed prior to being conducted to process boiler 790.

In some embodiments of the processes described herein, butanol may be recovered from fermentation broth utilizing extractive fermentation. That is, fermentation broth comprising butanol may be contacted with extractant to recover butanol. In some embodiments, fermentation broth and extractant may be added to a beer column or a side stripper to recover butanol. For example, fermentation broth and extractant may be fed to the beer column or side stripper near the top of the column. In some embodiments, extractant may be separated from the bottoms streams of the beer column or the side stripper by centrifugation or decantation, and extractant may be recycled for reuse in a recovery process.

In some embodiments, to retrofit a bioethanol production plant may comprise the addition of a condenser to service both a beer column and a side stripper, a decanter, and a reboiler retrofitted to the base of a rectifier. In some embodiments, the condenser for an existing rectifier may be piped to service both a beer column and a side stripper. In some embodiments, the additional equipment may comprise valve switches, line breaks, pipe blinds, and the like to permit conversion between a biobutanol production plant and a bioethanol production plant.

Figure 8:
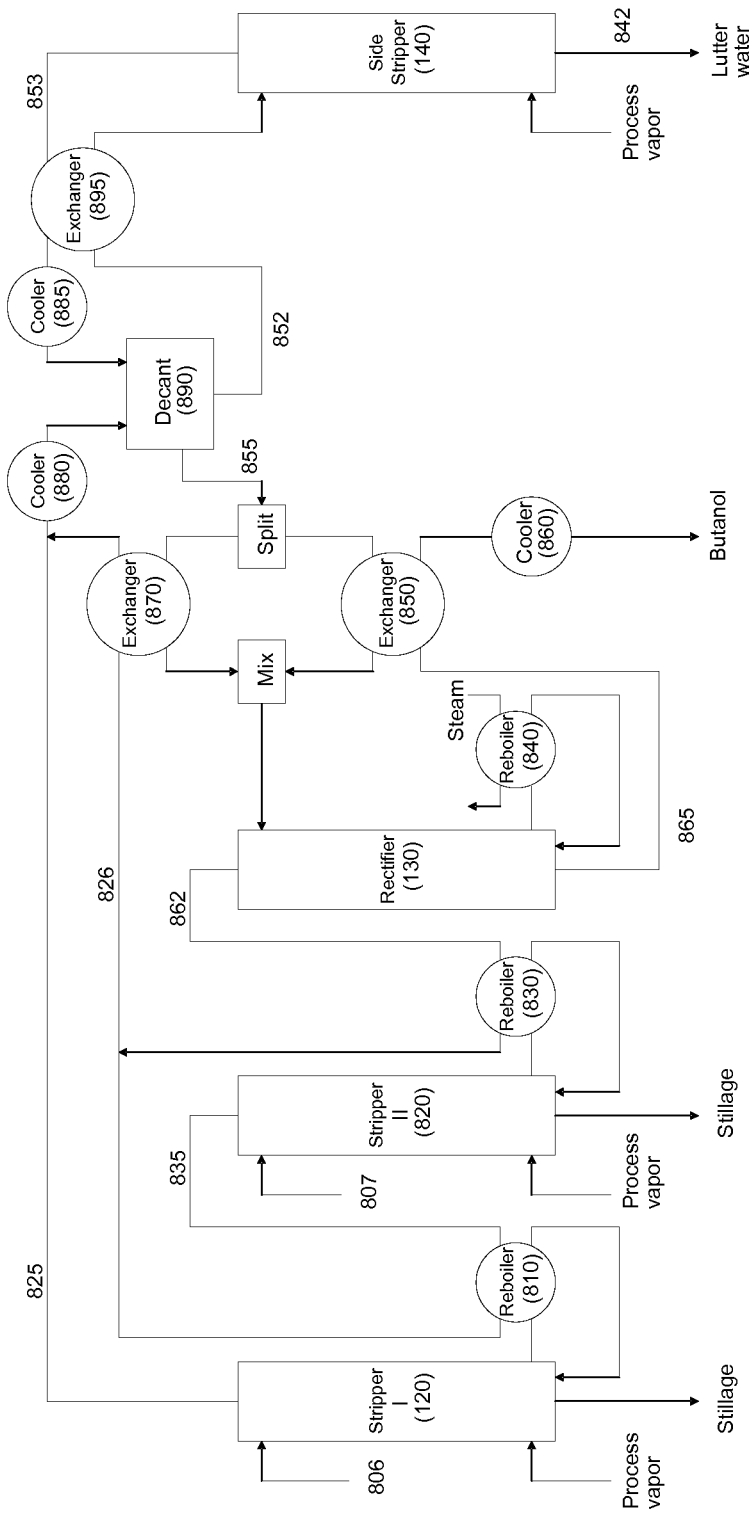
FIG. 8 illustrates another embodiment of the processes described herein.

FIG. 8 illustrates an embodiment of a process of the invention that recovers butanol from dilute aqueous and organic fermentation streams. Beer and/or extractant stream 806 may enter stripper column I (120) which may be a retrofit of the beer stripper column used in bioethanol production. Similarly, beer and/or extractant stream 807 may enter stripper column II (820) which may be a duplicate installation of the beer stripper column. Both stripper columns may be rated for full vacuum operation. In this figure, stripper column I (120) may operate close to 0.1 atm pressure and stripper column II (820) may operate close to 0.4 atm pressure. Both stripper columns may receive process vapor to aid in removing butanol from the bottoms stillage streams. Due to differences in operating pressure, vapor overhead stream 835 from stripper column II (820) may be at a higher temperature than the bottoms stillage of stripper column I (120) and may be used to transfer heat via reboiler 810. Vapor overhead stream 825 may be condensed in cooler 880 before entering decant 890 where it can phase split into aqueous stream 852 and organic stream 855. Organic stream 855 may be conducted to rectifier column 130 at a pressure close to 1.85 atm which may be retrofitted from the rectifier column of bioethanol production. The bottoms of rectifier 130 is stream 865 and may be substantially butanol. This product butanol may be partially cooled by transferring heat via heat exchanger 850 to a portion of organic stream 855. The product butanol may then be further cooled using cooler 860 for storage. The vapor overhead of rectifier 130 is stream 862 and this stream may be at a higher temperature than the bottoms of stripper column II (820) due to differences in operating pressure. Vapor overhead stream 862 may be used to transfer heat in reboiler 830 of stripper column II (820). Streams 835 and 862 after losing some heat in reboilers 810 and 830, respectively, may be combined to form stream 826 and may transfer additional heat in exchanger 870 to a portion of organic stream 955 before combining with vapor overhead stream 825. Aqueous stream 852 may be conducted to side stripper column 140 operating close to 0.4 atm which may be retrofitted from the side stripper column of bioethanol production. The vapor overhead stream 853 of side stripper column 140 may transfer some heat to aqueous stream 852 via heat exchanger 895 before being further cooled in cooler 885 and conducted to decant 890.

A retrofitted bioethanol production plant as described herein may also comprise a multi-effect evaporation system. For example, a multi-effect evaporation system may comprise three (3) train, triple effect evaporators; four (4) train, double effect evaporators; two (2) train, quadruple effect evaporators; or five (5) train, double effect evaporators. The evaporators of each effect may be of any conventional design. As an example, each evaporator may include an upper portion having a shell tube heat exchanger as known in the art and a lower pot portion. Condensate from each evaporator may be combined and recycled in the production plant. The various lines leading to the evaporators may be valved so that any one of the evaporators may be taken off-line and bypassed for maintenance and conversion.

In some embodiments, the vapor inlets of first effect evaporators may receive clean plant steam and/or reused plant steam as a heat source (or powerhouse steam). In some embodiments, effect steam may supply sufficient heat for operating a beer column, side stripper, butanol column, and/or extractant column. In some embodiments, plant steam may be used with effect steam to supply sufficient heat for operating a beer column and/or extractant column. For recovery of butanol or other product alcohols, steam from a multi-effect evaporation system may be used to supply heat to one or more distillation unit operations of the process. In some embodiments, the one or more distillation unit operations receiving heat from the multi-effect evaporation system may be maintained at a pressure below atmospheric pressure, thereby avoiding having to pressurize the steam prior to injection into the particular distillation column. Examples of multi-train, multi-effect evaporation systems are described in U.S. Patent Application Publication No. 2011/0315541 and International Patent Application No. PCT/US2012/068288; the entire contents of each are herein incorporated by reference.

Figure 9:
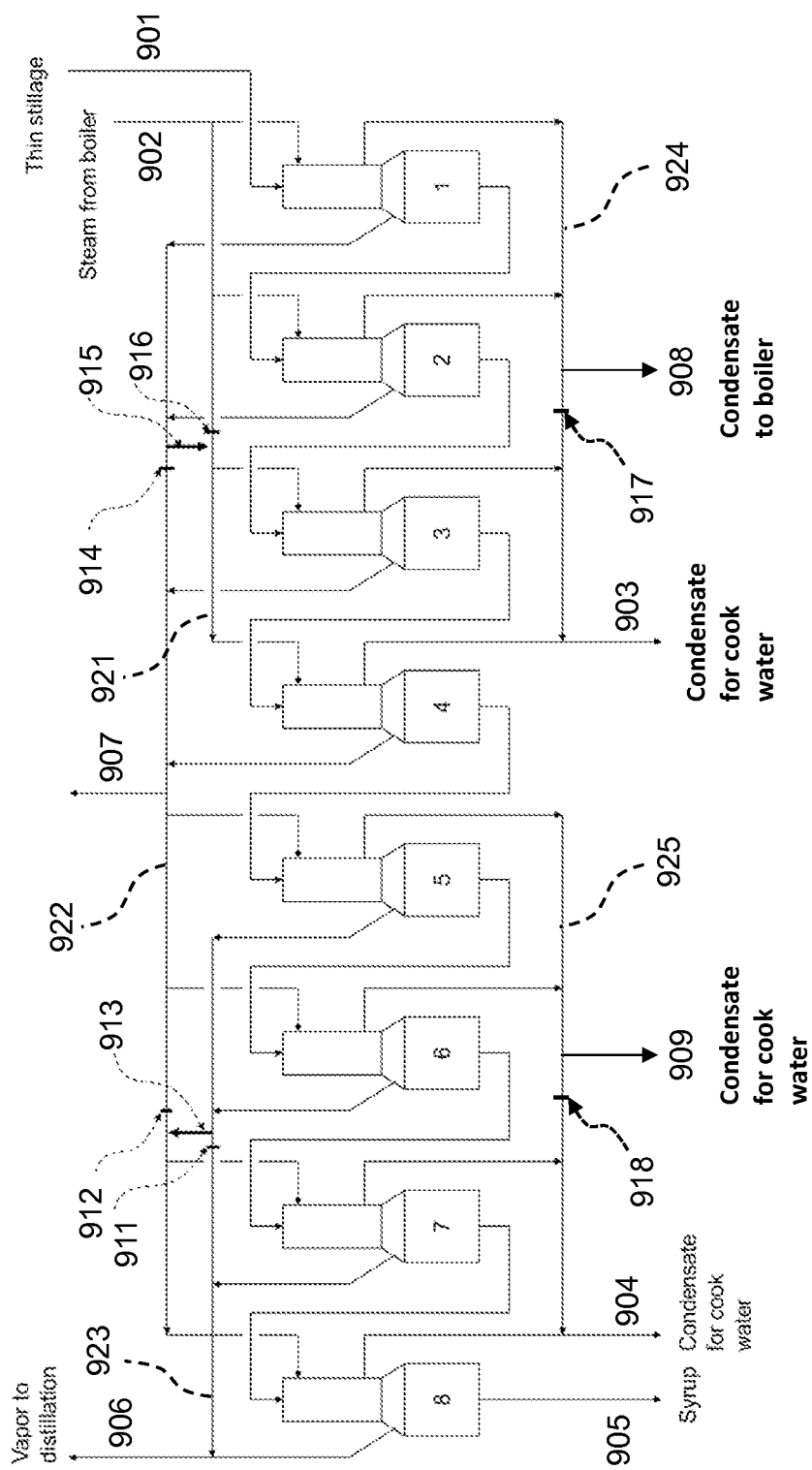
FIG. 9 illustrates an example of an evaporation system that may be utilized in a retrofit bioethanol production plant.

FIG. 9 illustrates an example of an evaporation system that includes piping changes to convert from two effects to four effects. Manifolds are represented by horizontal lines 921, 922, and 923 that have multiple feeds or multiple branches connected to them and are primarily used for conveying water vapor and water condensate. Steam supplied via 902 feeds manifold 921 that distributes portions of this steam to evaporator bodies 1, 2, 3, and 4. In some embodiments, blind 916 may be inserted in manifold 921 at a position downstream of the branch that supplies steam to body 2 but upstream of the branch that feeds body 3. Water vapor generated by bodies 1 and 2 enter a different manifold 922. Blind 914 may be inserted in this manifold at a position downstream of where water vapor from body 2 enters but upstream of where water vapor from body 3 enters. A new piping connection 915 may be inserted that originates from manifold 922 upstream of blind 914 but downstream of where water vapor from body 2 enters. Piping connection 915 may connect to manifold 921 downstream of blind 916 but upstream of the branch leading to body 3. Piping connection 915 allows water vapor from bodies 1 and 2 to be directed to evaporator bodies 3 and 4. Water vapor generated by bodies 3 and 4 may enter manifold 922 downstream of blind 914.

A portion of this combined vapor in manifold 922 may be removed as stream 907 and may be directed to a distillation column such as a beer stripping column. The remaining portion of vapor in manifold 922 may be distributed only to bodies 5 and 6 using a blind 912 installed in manifold 922 downstream of the branch leading to body 6 but upstream of the branch to body 7. Water vapor generated by bodies 5 and 6 may enter manifold 923 and blind 911 may be installed in manifold 923 downstream of where vapor from body 6 enters. A new piping connection 913 may be installed that originates from manifold 923 upstream of blind 911 but downstream of where water vapor from body 6 enters. Piping connection 913 may connect to manifold 922 downstream of blind 912 but upstream of the branch leading to body 7. Piping connection 913 allows water vapor from bodies 5 and 6 to be directed to evaporator bodies 7 and 8. Water vapor generated by bodies 7 and 8 may enter manifold 923 downstream of blind 911 and this combined vapor may be removed as stream 906 and may be directed to a distillation column such as an extractant stripping column.

The vapors are condensed and typically collected in common manifolds 924 and 925. In some embodiments, blind 917 may be installed in manifold 924 downstream of where the condensate from evaporator body 2 enters and upstream of where the condensate from evaporator body 3 enters. The condensates from bodies 1 and 2 may be removed as stream 908 and routed to a boiler for steam generation. The process condensates from bodies 3 and 4 may exit as stream 903 and may be used in the preparation of mash. Blind 918 may be installed in manifold 925 downstream of where the condensate from body 6 enters and upstream of where the condensate from body 7 enters. The condensates from bodies 5 and 6 may be removed as stream 909 and may be used in the preparation of mash. The condensates from bodies 7 and 8 may be removed as stream 904 and may be used in the preparation of mash. As an advantage of the reconfiguration shown in FIG. 9, carboxylic acids (e.g., acetic acid, isobutyric acid) that may be present in thin stillage 901 may be contained in condensate stream 903. Condensate stream 903 may be treated to remove carboxylic acids, for example, by anaerobic digestion, prior to recycling for the preparation of mash. In some embodiments, condensate streams 904 and 909 may bypass this treatment step. In the case where an anaerobic digestion unit is at an ethanol production facility, such a retrofit may be expected to improve its volumetric capacity.

In some embodiments, the pressure of operation for all evaporator bodies may be adjusted to enable four effects. For example, the pressure at which evaporation takes place in bodies 3 and 4 may be less than the pressure at which evaporation takes place in bodies 1 and 2. The pressure at which evaporation takes place in bodies 5 and 6 may be less than the pressure at which evaporation takes place in bodies 3 and 4. The pressure at which evaporation takes place in bodies 7 and 8 may be less than the pressure at which evaporation takes place in bodies 5 and 6.

As another example of an evaporation system, eight evaporators may be arranged as a two (2) train, quadruple effect configuration. In some embodiments, two evaporators may utilize powerhouse steam and in some embodiments, no evaporators utilize process steam. As described herein, whole stillage may be further processed, for example, by centrifugation to remove any undissolved solids. The remaining centrifugate may be recycled as backset or may be conducted to the evaporators for recovery of water and syrup.

The beer column may be heated using process steam from various sources throughout the production plant. For example, the beer column may be heated with process steam from second or later effect evaporators. In some embodiments, the process steam may be sufficient to allow vaporization of at least about 98% to at least about 100% butanol. In some embodiments, steam may be directly injected into the beer column. In some embodiments, heat may be recovered from condensation of vapors from the beer column and this heat may be used to heat the feeds to the distillation columns or this heat may be used for the preboiler. In some embodiments, vapors from the beer column may be condensed using heat exchangers in conjunction with the heating of other streams. In some embodiments, these vapors may be condensed via an existing condenser used in conjunction with an existing rectifier in a retrofit bioethanol production plant. For example, the existing condenser may be modified with a combination of valves, spectacle blanks, and piping segments in order to condense the vapors from the beer column.

The retrofit bioethanol production plant may include a new reboiler. This reboiler may provide powerhouse steam to an existing rectifier. In other embodiments, a reboiler may be included in a newly constructed butanol production plant and this reboiler may provide powerhouse steam to a rectifier. In some embodiments, overheads from the rectifier column may be condensed with heat recovery and this heat may be used to power one or more evaporators. In addition, bottoms from the rectifier column may be cooled by process to process heat recovery.

As described herein, corn may be used as a feedstock for the production of ethanol or butanol and may be subjected to processing, for example, wet milling. Effluents such as wastewaters from the corn milling process as well as other process wastewaters may be treated by anaerobic digestion. Treatment of these waste products by anaerobic digestion can generate value-added products such as energy, fertilizers, chemicals, and biofuels. Therefore, as a means of waste management and/or to process biodegradable waste, a retrofit bioethanol production plant or newly constructed biobutanol production plant may comprise one or more anaerobic digesters. These anaerobic digesters may be used, for example, to provide energy for the production plant. In some embodiments, an anaerobic digester may be a completely mixed anaerobic digester, an upflow anaerobic sludge blanket reactor, an anaerobic fluidized bed reactor, an expanded granular sludge bed reactor, or an aerobic filter.

As described herein, converting a bioethanol production plant to a biobutanol production plant may involve, for example, retrofitting and reconfiguring the equipment to enable fermentation and purification of butanol. By retrofitting and reconfiguring the existing equipment in a bioethanol production plant, this conversion may be allow for minimal disruption of the production plant as well as minimal use of capital. Existing equipment may be reused and repurposed and in some instances, requiring little to no modifications (e.g., modifications of internal components). For example, centrifuges are large complex pieces of rotating machinery built to precise specifications. Replacing internal components of a centrifuge can be costly and time consuming (e.g., delay in ordering replacement parts, installing new part, mobilizing equipment for replacement to be performed by an equipment supplier, and the like). Reusing the existing centrifuges without modifications to internal components would allow for minimal disruption and use of capital.

As another example, distillation columns may be designed with a certain diameter, internal trays, packing, or a combination of these elements for the purpose of ethanol purification. In addition, the column may require a certain number of equilibrium stages for ethanol purification. For a retrofit of a distillation column, the same multi-stage separation with existing column internals may be repurposed to purify butanol.

Furthermore, equipment is generally not designed for dual purposes. During construction of bioethanol facilities, there may have been little or no anticipation that these facilities could be converted to produce other alcohols such as butanol. Therefore, it may not be expected that equipment such as distillation columns and centrifuges designed for ethanol production may be repurposed for butanol production. In addition, it may not be expected that such equipment could be repurposed without making modifications. Equipment modification would most likely cause a shutdown of production and time delays as well as added costs for modifications and operating costs, and loss of income. By repurposing existing equipment, there would most likely be a minimal disruption of production and minimal capital cost. For example, modifications for repurposing existing equipment may be piping and valve installation which costs may be modest as compared to replacing the existing equipment with new equipment. In addition, to minimize loss of operational flexibility, the conversion to a biobutanol plant may be reversible.

While not wishing to be bound by theory, it is believed that the methods and processes described herein are useful in conjunction with any alcohol producing microorganism, particularly recombinant microorganisms which produce alcohol.

Recombinant microorganisms which produce alcohol are also known in the art (e.g., Ohta, et al., Appl. Environ. Microbiol. 57:893-900, 1991; Underwood, et al., Appl. Environ. Microbiol. 68:1071-1081, 2002; Shen and Liao, Metab. Eng. 10:312-320, 2008; Hahnai, et al., Appl. Environ. Microbiol. 73:7814-7818, 2007; U.S. Pat. No. 5,514,583; U.S. Pat. No. 5,712,133; PCT Application Publication No. WO 1995/028476; Feldmann, et al., Appl. Microbiol. Biotechnol. 38: 354-361, 1992; Zhang, et al., Science 267: 240-243, 1995; U.S. Patent Application Publication No. 2007/0031918 A1; U.S. Pat. No. 7,223,575; U.S. Pat. No. 7,741,119; U.S. Patent Application Publication No. 2009/0203099 A1; U.S. Patent Application Publication No. 2009/0246846 A1; and PCT Application Publication No. WO 2010/075241; the entire contents of each are herein incorporated by reference).

As an example, the metabolic pathways of microorganisms may be genetically modified to produce a product alcohol (e.g., butanol). These pathways may also be modified to reduce or eliminate undesired metabolites, and thereby improve yield of the product alcohol. The production of butanol by a microorganism is disclosed, for example, in U.S. Patent Application Publication No. 2007/0092957; U.S. Patent Application Publication No. 2007/0259410; U.S. Patent Application Publication No. 2007/0292927; U.S. Patent Application Publication No. 2008/0182308; U.S. Patent Application Publication No. 2008/0274525; U.S. Patent Application Publication No. 2009/0305363; and U.S. Patent Application Publication No. 2009/0305370; the entire contents of each are herein incorporated by reference. In some embodiments, microorganisms may comprise a butanol biosynthetic pathway or a biosynthetic pathway for a butanol isomer such as 1-butanol, 2-butanol, or isobutanol. In some embodiments, the microorganism may be bacteria, cyanobacteria, filamentous fungi, or yeasts. Suitable microorganisms capable of producing product alcohol via a biosynthetic pathway include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Zygosaccharomyces, Debaryomyces, Candida, Brettanomyces, Pachysolen, Hansenula, Issatchenkia, Trichosporon, Yamadazyma*, or *Saccharomyces*. In some embodiments, recombinant microorganisms may be selected from the group consisting of *Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis, Candida sonorensis, Candida methanosorbosa, Kluyveromyces lactis, Kluyveromyces marxianus, Kluyveromyces thermotolerans, Issatchenkia orientalis, Debaryomyces hansenii*, and *Saccharomyces cerevisiae*. In some embodiments, the recombinant microorganism is yeast. In some embodiments, the recombinant microorganism is crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Saccharomyces uvarum, Saccharomyces castelli, Saccharomyces kluyveri, Zygosaccharomyces rouxii, Zygosaccharomyces bailli*, and *Candida glabrata*.

While various embodiments of the present invention have been described herein, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The following non-limiting examples will further illustrate the invention. It should be understood that, while the following examples involve corn as feedstock, other biomass sources such as cane may be used for feedstock without departing from the present invention. Moreover, while the following examples involve ethanol and butanol, other alcohols may be produced without departing from the present invention.

The processes described herein may be demonstrated using computational modeling such as Aspen modeling (see, e.g., U.S. Pat. No. 7,666,282). For example, the commercial modeling software Aspen Plus® (Aspen Technology, Inc., Burlington, Mass.) may be used in conjunction with physical property databases such as DIPPR, available from American Institute of Chemical Engineers, Inc. (New York, N.Y.) to develop an Aspen model for an integrated butanol fermentation, purification, and water management process. This process modeling can perform many fundamental engineering calculations, for example, mass and energy balances, vapor/liquid equilibrium, and reaction rate computations. In order to generate an Aspen model, information input may include, for example, experimental data, water content and composition of feedstock, temperature for mash cooking and flashing, saccharification conditions (e.g., enzyme feed, starch conversion, temperature, pressure), fermentation conditions (e.g., microorganism feed, glucose conversion, temperature, pressure), degassing conditions, solvent columns, pre-flash columns, condensers, evaporators, centrifuges, etc.

Example 1

Into a large mixing tank via a mixing conveyor, 53.5 tonnes/hr of dry ground corn is slurried into 123.6 tonnes/hr of mash including combined recycled cook water, backset (38% of total liquids), ammonia, and enzyme and heated to 85° C. The mash is then transferred through a hydroheater along with injected steam, subsequently flashed, and then liquefied with additional enzyme in another tank to produce 178.2 tonnes/hr of liquefied mash. The liquefied mash is cooled by heat exchange with a portion of post-fermentation material and subsequently cooling water before being combined with an isobutanol-producing microorganism and 138.4 tonnes/hr of oleyl alcohol in a batch-sequenced arrangement of fermentors. Starch is converted to isobutanol while venting on average 17.4 tonnes/hr of $CO_2$-rich off-gas. Multi-phase material is discharged from the fermentors to a beer well for any additional degassing and then transferred to an existing beer column at an average rate of 299.2 tonnes/hr after first picking up heat from both liquefied mash and recycled extractant via parallel heat exchange. The beer column is operated under vacuum near 0.5 atm absolute pressure (similar to during ethanol manufacture) using 36.3 tonnes/hr of direct injected water vapor sourced from the last effect of an evaporation train. The column has the equivalent of 15 equilibrium vapor-liquid contacting stages and the fermentation discharge material is introduced on the 3rd stage from the top. An average flow of 52.1 tonnes/hr of vapor comprised of 51.6 wt % isobutanol, 46.6 wt % water, and 1.8 wt % $CO_2$ is stripped out of the top of the column and condensed into a vented isobutanol decanter that combines the vapor condensate from all distillation columns. Condensed decanted iBuOH-rich organic layer (15.0 tonnes/hr) is returned to the top stage of the column for reflux. The bottom outlet material, constituting 298.4 tonnes/hr of whole stillage and heterogeneously mixed extractant, is processed through three-phase centrifuges to yield 17.5 tonnes/hr of wet distillers grains (34.4 wt % dry solids), 142.5 tonnes/hr of thin stillage, and 138.4 tonnes/hr of a lighter density organic extractant phase that is cooled for reuse in a subsequent fermentation by exchanging heat with a portion of fermentation discharge material. A remaining portion of 35.0 tonnes/hr iBuOH-rich organic layer is directed from the isobutanol decanter to the top stage of an existing rectifier column. This column has the equivalent of 10 equilibrium stages and is equipped with a newly installed reboiler that will enable delivery of 28.3 GJ/hr duty using steam. Consequently, a top vapor outlet of 20.3 tonnes/hr comprised of 67.2 wt % isobutanol, 32.3 wt % water, and 0.5 wt % $CO_2$ is produced and condensed into the isobutanol decanter. Substantially pure isobutanol (14.7 tonnes/hr) is produced from the bottom. The water-rich aqueous layer from the isobutanol decanter is transferred at a rate of 27.7 tonnes/hr to an existing side stripper column. This column has the equivalent of 10 equilibrium stages and is operated using 6.7 tonnes/hr of water vapor sourced from flashing the hydroheated mash. A top vapor outlet of 63.2 tonnes/hr comprised of 58.7 wt % isobutanol, 40.7 wt % water, and 0.6 wt % $CO_2$ is produced and condensed into the isobutanol decanter. Substantially pure water (28.1 tonnes/hr) is produced from the bottom and recycled back as cook water.

Example 2

Figure 10A:
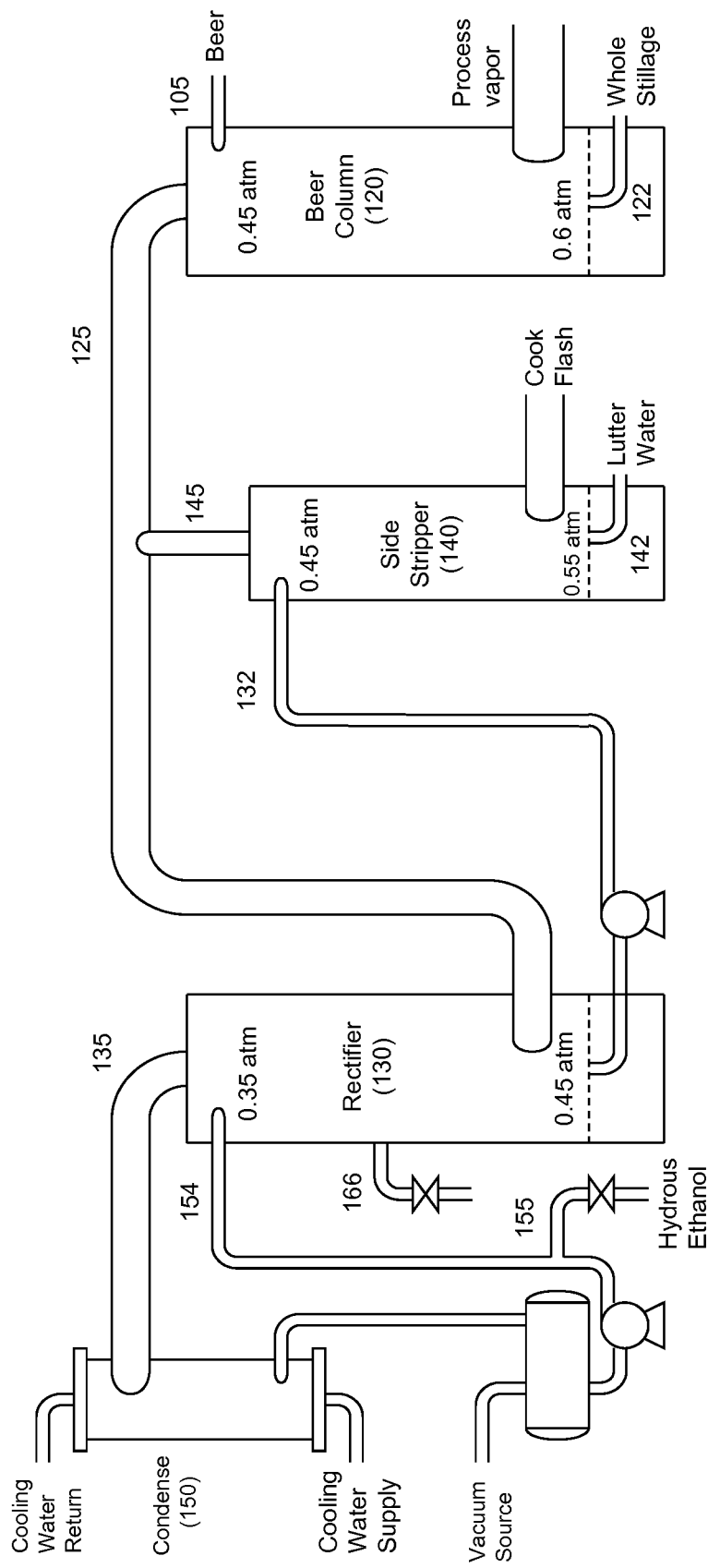
FIGS. 10A to 10C illustrate the retrofit of the distillation system of a bioethanol plant.
Figure 10B:
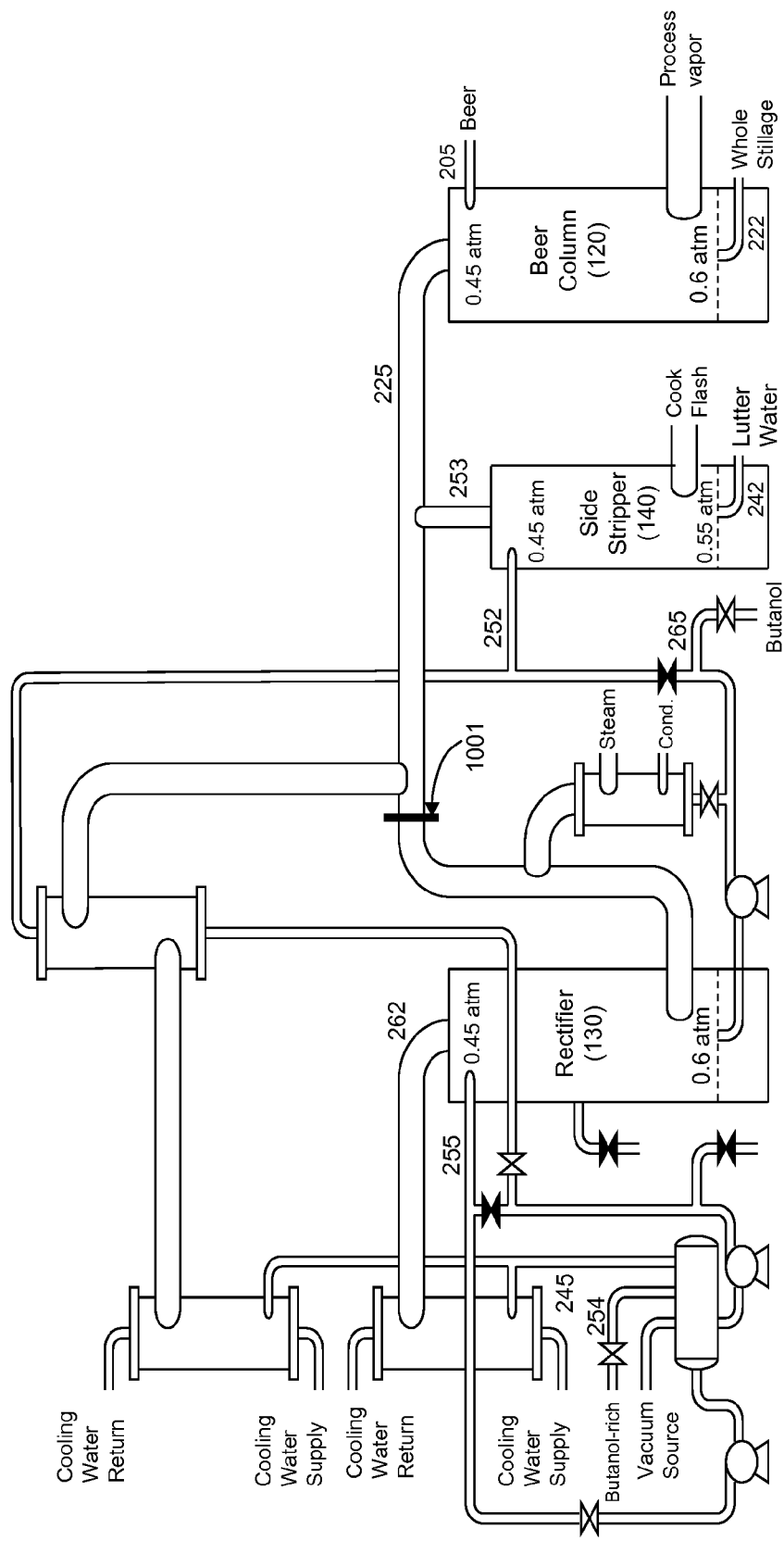
Figure 10C:
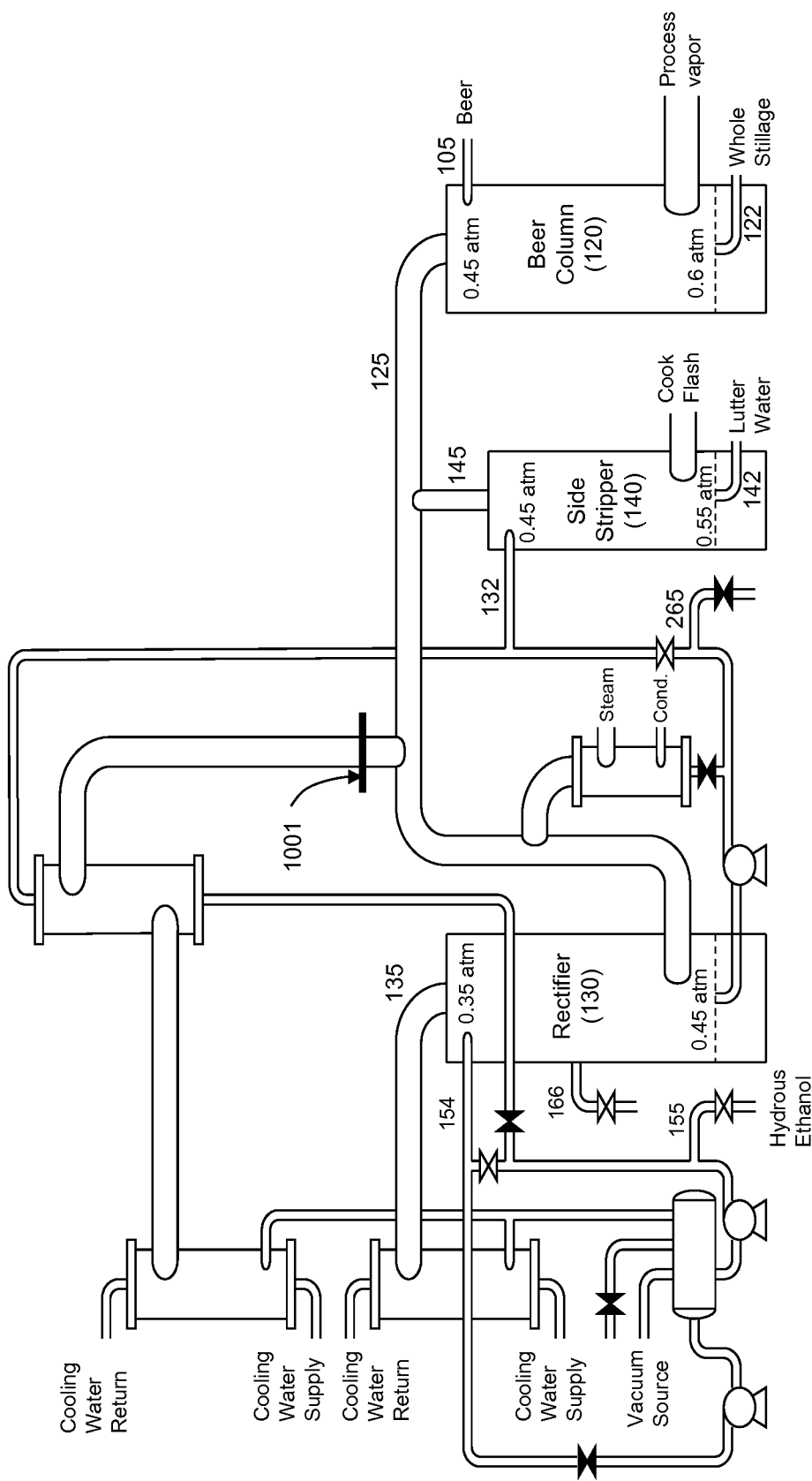

Referring to FIGS. 10A to 10C, FIG. 10A illustrates a bioethanol production facility and FIG. 10B illustrates a retrofit of the bioethanol production facility converting the facility to a biobutanol production facility by adding valves, blinds, piping connections, and heat exchangers. For example, a reboiler is added to the rectifier column and additional cooling capacity is added to the beer column and the side stripper. In addition, blind 1001 is added to redirect overhead vapor streams 225 and 253 to the new cooling capacity. Valves (open valves are indicated in white and closed valves are indicated in black) shown in FIG. 10B are installed to redirect stream flows for butanol production. No modifications were made to the existing equipment. FIG. 10C illustrates reversion to a bioethanol production facility by opening the closed valves, closing the open valves, and relocating blind 1001.

A simulation of the bioethanol production facility, depicted in FIGS. 1 and 10A, operating 352 days/yr was performed. Dry ground corn was fed at a rate of 18 MM bushels/yr to produce 50 MM gal/yr ethanol. The distillation operation is illustrated in FIG. 10A. A beer stream 105 is discharged from fermentation at an average flow of 620 gpm (gallons per minute) comprising a titer of 128 g/liter ethanol. Other dissolved components include 12.8 g/liter glycerol, 22.7 g/liter proteins, and 10.6 g/liter salts. The beer was heat exchanged using liquefied mash up to 75° C. and then fed to the top of beer column 120. A process vapor stream sourced from the evaporation train was simultaneously fed into the bottom of beer column 120 at a rate of about 27,000 kg/hr. The beer column was sized for 12 equilibrium stages with a diameter of 10 feet, the side stripper column was sized for 10 equilibrium stages with a diameter of 4.5 feet and the rectifier column was sized for 10 equilibrium stages with a diameter of 12 feet. The mass balance for bioethanol production facility as illustrated in FIG. 10A is shown in Table 1. The units for water, ethanol, glycerol protein, salts, and solids are kg/hr.

TABLE 1

| Stream | Process Vapor | Cook Flash | 105 | 122 | 125 | 132 | 142 | 145 | 166 | 155 |
|---|---|---|---|---|---|---|---|---|---|---|
| T, °C. | 95 | 88 | 75 | 86 | 72.4 | 72.5 | 84 | 75 | 35 | 42 |
| P, atm | 0.8 | 0.6 | 0.45 | 0.6 | 0.45 | 0.45 | 0.55 | 0.45 | 1 | 0.35 |
| $H_2O$ | 26769 | 5150 | 115500 | 123332 | 18937 | 22896 | 24066 | 3981 | 1952 | 43 |
| Ethanol | | | | 18000 | 0.25 | 17999 | 1908 | 0.1 | 1908 | 1048 | 18939 |
| Glycerol | | | 1800 | 1800 | | | | | | |
| Protein | | | 3200 | 3200 | | | | | | |
| Salts | | | 1500 | 1500 | | | | | | |
| Solids | | | 3500 | 3500 | | | | | | |

A simulation of the biobutanol production facility that was retrofitted from a bioethanol production facility, depicted in FIG. 10B, operating 352 days/yr was performed. Dry ground corn was fed at a rate of 18 MM bushels/yr to produce 36 MM gal/yr isobutanol. The distillation operation is illustrated in FIG. 10B. A beer stream 205 is discharged from fermentation at an average flow of 610 gpm comprising a titer of 10.65 g/liter isobutanol. Other dissolved components include 17.0 g/liter glycerol, 19.5 g/liter proteins, and 9.6 g/liter salts. The beer was heat exchanged using liquefied mash up to 75° C. and then fed to the top of beer column 120. A process vapor stream sourced from the evaporation train was simultaneously fed into the bottom of beer column 120 at a rate of about 8,000 kg/hr. The beer column was sized for 12 equilibrium stages with a diameter of at least 6 feet, the side stripper column was sized for 10 equilibrium stages with a diameter of 4.5 feet and the rectifier column was sized for 10 equilibrium stages with a diameter of 12 feet. The mass balance for biobutanol production facility as illustrated in FIG. 10B is shown in Table 2. The units for water, butanol, glycerol protein, salts, and solids are kg/hr.

TABLE 2

| Stream | Process Vapor | Cook Flash | 205 | 222 | 225 | 252 | 242 | 253 | 254 | 262 | 265 |
|---|---|---|---|---|---|---|---|---|---|---|---|
| T, °C. | 94 | 86 | 75 | 86 | 77.6 | 65 | 84 | 76.4 | 35 | 77 | 98.3 |
| P, atm | 0.8 | 0.6 | 0.45 | 0.6 | 0.45 | 0.6 | 0.55 | 0.45 | 1 | 0.45 | 0.7 |
| $H_2O$ | 8205 | 5405 | 132000 | 135025 | 5179 | 22100 | 25196 | 4311 | 8032 | 8082 | 0 |
| Butanol | | | 1500 | 0.5 | 1499.5 | 1984 | 0.1 | 2056 | 35780 | 21978 | 13802 |
| Glycerol | | | 2400 | 2400 | | | | | | | |
| Protein | | | 2750 | 2750 | | | | | | | |
| Salts | | | 1350 | 1350 | | | | | | | |
| Solids | | | 3500 | 3500 | | | | | | | |

This example demonstrates that distillation columns designed for ethanol purification in a bioethanol production facility can be repurposed without modification for butanol purification in a retrofitted bioethanol production facility.

What is claimed is:

1. A method for improving the product profile of an ethanol production plant comprising modifying the plant to produce one or more biofuel products other than ethanol wherein modifying the plant comprises
   adding a mixing device and a separation system to an external cooling loop of a fermentor, adding one or more separation units,
   separating a feedstock slurry prior to fermentation to form streams: (i) an aqueous solution comprising fermentable sugars, (ii) a wet cake comprising undissolved solids, and (iii) an oil stream,
   adding one or more extractant columns and/or extractant separation units,
   repurposing an ethanol beer column for distillation of an alcohol other than ethanol, and reconfiguring an evaporation train,
   wherein the modifications allow the plant to be reverted to ethanol production.

2. The method of claim 1, further comprising adding one or more condensation units and/or adding one or more decantation units.

3. A method for improving the product profile of an ethanol production plant comprising modifying the plant to produce one or more biofuel products other than ethanol wherein modifying the plant comprises
   adding a mixing device and a separation system to an external cooling loop of a fermentor,
   adding one or more separation units,
   separating a feedstock slurry prior to fermentation to form streams: (i) an aqueous solution comprising fermentable sugars, (ii) a wet cake comprising undissolved solids, and (iii) an oil stream,
   adding one or more flash units and/or condensation units,
   repurposing an ethanol beer column for distillation of an alcohol other than ethanol, and
   reconfiguring an evaporation train,
   wherein the modifications allow the plant to be reverted to ethanol production.

4. The method of claim 3, further comprising adding one or more preflash units and/or compressor units.

5. The method of claim 1, further comprising adding one or more hydrolyzers.

6. The method of claim 1, wherein the one or more biofuel products comprises butanol.

7. The method of claim 1, wherein the one or more biofuel products comprises butanol and fusel oils.

8. The method of claim 1, wherein the one or more biofuel product comprises butanol and oil.

9. The method of claim 1, wherein the one or more separation units is selected from decanter bowl centrifugation, three-phase centrifugation, disk stack centrifugation, filtering centrifugation, decanter centrifugation, filtration, vacuum filtration, beltfilter, pressure filtration, filtration using a screen, screen separation, grating, porous grating, flotation, hydrocyclone, filter press, screwpress, gravity settler, vortex separator, and combinations thereof.

10. The method of claim 1, wherein the one or more extraction separation units is selected from hydrocyclone, centrifuge, inline vortex separator, decanter, filter, siphon, mixer-settler, gravity settler, and combinations thereof.

11. The method of claim 1, wherein the one or more extraction columns comprises a rectification section.

12. The method of claim 1, wherein the evaporation train is configured as a four train, double effect evaporation system, a three train, triple effect evaporation system, or a two train, quadruple effect evaporation system.

13. The method of claim 1, further comprising adding a methanator.

14. The method of claim 1, further comprising adding solids washing equipment comprising one or more centrifuges and a conveyor, wherein the wet cake is further processed by the solids washing equipment.

15. The method of claim 3, wherein the one or more separation units is selected from decanter bowl centrifugation, three-phase centrifugation, disk stack centrifugation, filtering centrifugation, decanter centrifugation, filtration, vacuum filtration, beltfilter, pressure filtration, filtration using a screen, screen separation, grating, porous grating, flotation, hydrocyclone, filter press, screwpress, gravity settler, vortex separator, and combinations thereof.

16. The method of claim 3, further comprising adding one or more condensation units.

17. The method of claim 3, wherein the evaporation train is configured as a four train, double effect evaporation system, a three train, triple effect evaporation system, or a two train, quadruple effect evaporation system.

18. The method of claim 3, further comprising adding a methanator.

19. The method of claim 3, further comprising adding solids washing equipment comprising one or more centrifuges and a conveyor, wherein the wet cake is further processed by the solids washing equipment.

20. The method of claim 3, wherein the one or more biofuel products comprises butanol.

21. The method of claim 1, wherein the mixing device is an inline mixer or piping tee.

22. The method of claim 1, wherein the separation system is hydrocyclone, centrifuge, inline vortex separator, decanter, or filter.

23. The method of claim 3, wherein the mixing device is an inline mixer or piping tee.

24. The method of claim 3, wherein the separation system is hydrocyclone, centrifuge, inline vortex separator, decanter, or filter.

* * * * *